United States Patent
DeRosa et al.

(10) Patent No.: US 11,433,144 B2
(45) Date of Patent: *Sep. 6, 2022

(54) BIODEGRADABLE LIPIDS FOR DELIVERY OF NUCLEIC ACIDS

(71) Applicant: Translate Bio, Inc., Lexington, MA (US)

(72) Inventors: Frank DeRosa, Chelmsford, MA (US); Michael Heartlein, Boxborough, MA (US)

(73) Assignee: Translate Bio, Inc., Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/141,744

(22) Filed: Jan. 5, 2021

(65) Prior Publication Data

US 2021/0369866 A1 Dec. 2, 2021

Related U.S. Application Data

(60) Continuation of application No. 16/692,846, filed on Nov. 22, 2019, now Pat. No. 10,912,844, which is a continuation of application No. 16/002,878, filed on Jun. 7, 2018, now Pat. No. 10,493,166, which is a division of application No. 15/314,818, filed as application No. PCT/US2015/033173 on May 29, 2015, now Pat. No. 10,022,455.

(60) Provisional application No. 62/005,266, filed on May 30, 2014.

(51) Int. Cl.
| | |
|---|---|
| *C07D 319/12* | (2006.01) |
| *A61K 48/00* | (2006.01) |
| *C12N 15/11* | (2006.01) |
| *A61K 9/127* | (2006.01) |
| *A61K 38/18* | (2006.01) |
| *A61K 38/48* | (2006.01) |

(52) U.S. Cl.
CPC ........ *A61K 48/0033* (2013.01); *A61K 9/1272* (2013.01); *A61K 38/1816* (2013.01); *A61K 38/4846* (2013.01); *A61K 48/005* (2013.01); *A61K 48/0025* (2013.01); *A61K 48/0041* (2013.01); *C07D 319/12* (2013.01); *C12N 15/111* (2013.01); *C12Y 304/21022* (2013.01); *C12N 2310/11* (2013.01); *C12N 2310/14* (2013.01); *C12N 2310/141* (2013.01); *C12N 2320/32* (2013.01)

(58) Field of Classification Search
CPC .................................................. C07D 319/12
See application file for complete search history.

(56) References Cited

U.S. PATENT DOCUMENTS

| | | | |
|---|---|---|---|
| 2,647,121 A | 7/1953 | Jacoby |
| 2,717,909 A | 9/1955 | Kosmin |
| 2,819,718 A | 1/1958 | Goldman |
| 2,844,629 A | 7/1958 | William et al. |
| 3,096,560 A | 7/1963 | Liebig |
| 3,535,289 A | 10/1970 | Yoshihara et al. |
| 3,614,954 A | 10/1971 | Mirowski et al. |
| 3,614,955 A | 10/1971 | Mirowski |
| 3,656,185 A | 4/1972 | Carpentier |
| 3,805,301 A | 4/1974 | Liebig |
| 3,945,052 A | 3/1976 | Liebig |
| 3,995,623 A | 12/1976 | Blake et al. |
| 4,013,507 A | 3/1977 | Rembaum |
| 4,022,833 A | 5/1977 | Diana et al. |
| 4,072,146 A | 2/1978 | Howes |
| 4,096,860 A | 6/1978 | McLaughlin |
| 4,099,528 A | 7/1978 | Sorenson et al. |
| 4,106,129 A | 8/1978 | Carpentier et al. |

(Continued)

FOREIGN PATENT DOCUMENTS

| | | |
|---|---|---|
| CA | 2518132 A1 | 3/2006 |
| CA | 2 769 408 | 2/2011 |

(Continued)

OTHER PUBLICATIONS

U.S. Appl. No. 61/494,714, filed Jun. 8, 2011, Guild.
U.S. Appl. No. 16/002,889, filed Jun. 7, 2018, DeRosa et al.
U.S. Appl. No. 16/002,897, filed Jun. 7, 2018, DeRosa et al.
U.S. Appl. No. 16/002,903, filed Jun. 7, 2018, DeRosa et al.
U.S. Appl. No. 61/494,745.

(Continued)

*Primary Examiner* — D Margaret M Seaman
(74) *Attorney, Agent, or Firm* — Proskauer Rose LLP; Fangli Chen

(57) ABSTRACT

The present invention provides, in part, a biodegradable compound of formula I, and sub-formulas thereof:Formula (I) or a pharmaceutically acceptable salt thereof, where each X independently is O or S, each Y independently is O or S, and each $R^1$ independently is defined herein; and a liposome composition comprising the cationic lipid of formula I or a sub-formula thereof, and methods of delivering agents, such as nucleic acids including mRNA, in vivo, by administering to a subject the liposome comprising the cationic lipid of formula I or a sub-formula thereof, where the agent is encapsulated within the liposome.

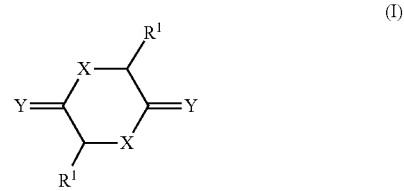

(I)

27 Claims, 1 Drawing Sheet
Specification includes a Sequence Listing.

(56) References Cited

U.S. PATENT DOCUMENTS

| | | |
|---|---|---|
| 4,134,402 A | 1/1979 | Mahurkar |
| 4,140,126 A | 2/1979 | Choudhury |
| 4,180,068 A | 12/1979 | Jacobsen et al. |
| 4,182,833 A | 1/1980 | Hicks |
| 4,227,533 A | 10/1980 | Godfrey |
| 4,284,459 A | 8/1981 | Patel et al. |
| 4,308,085 A | 12/1981 | Horhold et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,373,071 A | 2/1983 | Itakura |
| 4,375,817 A | 3/1983 | Engle et al. |
| 4,385,631 A | 5/1983 | Uthmann |
| 4,401,472 A | 8/1983 | Gerber |
| 4,401,796 A | 8/1983 | Itakura |
| 4,406,656 A | 9/1983 | Hattler et al. |
| 4,458,066 A | 7/1984 | Caruthers et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,737,323 A | 4/1988 | Martin et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,873,370 A | 10/1989 | Chiu |
| 4,878,908 A | 11/1989 | Martin et al. |
| 4,892,540 A | 1/1990 | Vallana |
| 4,897,355 A | 1/1990 | Eppstein et al. |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,102,872 A | 4/1992 | Singh et al. |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,153,319 A | 10/1992 | Caruthers et al. |
| 5,171,678 A | 12/1992 | Behr et al. |
| 5,176,661 A | 1/1993 | Evard et al. |
| 5,200,395 A | 4/1993 | Eto et al. |
| 5,261,419 A | 11/1993 | Osypka |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,326,887 A | 7/1994 | Di Cosimo et al. |
| 5,330,768 A | 7/1994 | Park et al. |
| 5,334,761 A | 8/1994 | Gebeyehu et al. |
| 5,352,461 A | 10/1994 | Feldstein et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,607,385 A | 3/1997 | Francischelli et al. |
| 5,609,624 A | 3/1997 | Kalis |
| 5,614,548 A | 3/1997 | Piantadosi et al. |
| 5,626,869 A | 5/1997 | Nygvist et al. |
| 5,631,018 A | 5/1997 | Zalipsky et al. |
| 5,693,088 A | 12/1997 | Lazarus |
| 5,697,953 A | 12/1997 | Kroll et al. |
| 5,700,437 A | 12/1997 | Fujii et al. |
| 5,700,642 A | 12/1997 | Monforte et al. |
| 5,705,188 A | 1/1998 | Junichi et al. |
| 5,705,385 A | 1/1998 | Bally et al. |
| 5,736,573 A | 4/1998 | Galat |
| 5,744,335 A | 4/1998 | Wolff et al. |
| 5,772,694 A | 6/1998 | Bokros et al. |
| 5,776,165 A | 7/1998 | Ripart |
| 5,776,747 A | 7/1998 | Schinstine et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,965,434 A | 10/1999 | Wolff et al. |
| 5,976,567 A | 11/1999 | Wheeler |
| 5,976,569 A | 11/1999 | Milstein |
| 5,981,501 A | 11/1999 | Wheeler et al. |
| 6,034,056 A | 3/2000 | Dutta |
| 6,055,454 A | 4/2000 | Heemels |
| 6,067,471 A | 5/2000 | Warren |
| 6,071,497 A | 6/2000 | Steiner et al. |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,152,955 A | 11/2000 | KenKnight et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,271,209 B1 | 8/2001 | Smith et al. |
| 6,299,604 B1 | 10/2001 | Ragheb et al. |
| 6,331,381 B1 | 12/2001 | Chaudhari et al. |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,444,226 B1 | 9/2002 | Steiner et al. |
| 6,534,484 B1 | 3/2003 | Wheeler et al. |
| 6,696,424 B1 | 2/2004 | Wheeler |
| 6,756,055 B2 | 6/2004 | McDonald et al. |
| 6,800,767 B2 | 10/2004 | Van Gansberghe et al. |
| 6,815,432 B2 | 11/2004 | Wheeler et al. |
| 6,821,530 B2 | 11/2004 | Koob et al. |
| 6,887,665 B2 | 5/2005 | Trulson et al. |
| 6,998,115 B2 | 2/2006 | Langer et al. |
| 7,022,214 B2 | 4/2006 | Olech |
| 7,084,303 B2 | 8/2006 | Watanabe et al. |
| 7,422,902 B1 | 9/2008 | Wheeler et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,820,676 B2 | 10/2010 | Leone-Bay et al. |
| 7,901,708 B2 | 3/2011 | MacLachlan et al. |
| 7,972,435 B2 | 7/2011 | Bury et al. |
| 8,071,082 B2 | 12/2011 | Zugates et al. |
| 8,093,367 B2 | 1/2012 | Kore et al. |
| 8,101,741 B2 | 1/2012 | MacLachlan et al. |
| 8,188,263 B2 | 5/2012 | MacLachlan et al. |
| RE43,612 E | 8/2012 | Anderson et al. |
| 8,236,943 B2 | 8/2012 | Lee et al. |
| 8,278,036 B2 | 10/2012 | Kariko et al. |
| 8,287,849 B2 | 10/2012 | Langer et al. |
| 8,304,529 B2 | 11/2012 | Kore et al. |
| 8,323,698 B2 | 12/2012 | Gu et al. |
| 8,329,070 B2 | 12/2012 | MacLachlan et al. |
| 8,399,686 B2 | 3/2013 | Markland et al. |
| 8,450,298 B2 | 5/2013 | Mahon et al. |
| 8,513,403 B2 | 8/2013 | MacLachlan et al. |
| 8,557,231 B2 | 10/2013 | Langer et al. |
| 8,562,966 B2 | 10/2013 | Zugates et al. |
| 8,569,256 B2 | 10/2013 | Heyes et al. |
| 8,710,200 B2 | 4/2014 | Schrum et al. |
| 8,808,681 B2 | 8/2014 | Anderson et al. |

(56) References Cited

U.S. PATENT DOCUMENTS

| | | |
|---|---|---|
| 8,822,663 B2 | 9/2014 | Schrum et al. |
| 8,853,377 B2 | 11/2014 | Guild et al. |
| 8,877,223 B2 | 11/2014 | Vange et al. |
| 8,883,202 B2 | 11/2014 | Manoharan et al. |
| 8,936,942 B2 | 1/2015 | Heyes et al. |
| 8,969,353 B2 | 3/2015 | Mahon et al. |
| 8,980,864 B2 | 3/2015 | Hoge et al. |
| 8,999,351 B2 | 4/2015 | Manoharan et al. |
| 8,999,950 B2 | 4/2015 | MacLachlan et al. |
| 9,006,487 B2 | 4/2015 | Anderson et al. |
| 9,011,832 B2 | 4/2015 | Arhancet et al. |
| 9,018,187 B2 | 4/2015 | Heyes et al. |
| 9,051,567 B2 | 6/2015 | Fitzgerald et al. |
| 9,061,059 B2 | 6/2015 | Chakraborty et al. |
| 9,074,208 B2 | 7/2015 | MacLachlan et al. |
| 9,089,604 B2 | 7/2015 | Chakraborty et al. |
| 9,095,552 B2 | 8/2015 | Chakraborty et al. |
| 9,101,666 B2 | 8/2015 | Langer et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,193,827 B2 | 11/2015 | Ma et al. |
| 9,220,755 B2 | 12/2015 | Chakraborty et al. |
| 9,220,792 B2 | 12/2015 | Chakraborty et al. |
| 9,227,197 B2 | 1/2016 | Kim |
| 9,233,141 B2 | 1/2016 | Chakraborty et al. |
| 9,238,716 B2 | 1/2016 | Dahlman et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,308,281 B2 | 4/2016 | Guild et al. |
| 9,315,472 B2 | 4/2016 | Dong et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,603,800 B2 | 3/2017 | Fahmy et al. |
| 10,022,455 B2 * | 7/2018 | Derosa ................ A61K 9/1272 |
| 10,286,082 B2 | 5/2019 | DeRosa et al. |
| 10,286,083 B2 | 5/2019 | DeRosa et al. |
| 10,293,057 B2 | 5/2019 | DeRosa et al. |
| 10,493,166 B2 * | 12/2019 | DeRosa ................ A61K 48/005 |
| 10,912,844 B2 * | 2/2021 | DeRosa ................ C12N 15/111 |
| 2002/0022721 A1 | 2/2002 | Trulson et al. |
| 2002/0094528 A1 | 7/2002 | Salafsky |
| 2002/0192651 A1 | 12/2002 | Wheeler et al. |
| 2002/0192721 A1 | 12/2002 | Rizzuto et al. |
| 2002/0193622 A1 | 12/2002 | Watanabe et al. |
| 2003/0082154 A1 | 5/2003 | Leamon |
| 2003/0181410 A1 | 9/2003 | Wheeler et al. |
| 2003/0215395 A1 | 11/2003 | Yu et al. |
| 2004/0142025 A1 | 7/2004 | MacLachlan et al. |
| 2004/0181077 A1 | 9/2004 | Raymond et al. |
| 2004/0235982 A1 | 11/2004 | Rabasco et al. |
| 2005/0059005 A1 | 3/2005 | Tuschl et al. |
| 2005/0069590 A1 | 3/2005 | Buehler et al. |
| 2005/0143332 A1 | 6/2005 | Monahan et al. |
| 2005/0148786 A1 | 7/2005 | Ikeda et al. |
| 2005/0244961 A1 | 11/2005 | Short et al. |
| 2006/0008910 A1 | 1/2006 | MacLachlan et al. |
| 2006/0069225 A1 | 3/2006 | Wintermantel et al. |
| 2006/0083780 A1 | 4/2006 | Heyes et al. |
| 2006/0099269 A1 | 5/2006 | Cheatham et al. |
| 2006/0223939 A1 | 10/2006 | Lange et al. |
| 2006/0228404 A1 | 10/2006 | Anderson et al. |
| 2007/0059373 A1 | 3/2007 | Oberg |
| 2007/0135372 A1 | 6/2007 | MacLachlan et al. |
| 2007/0142461 A1 | 6/2007 | Baker et al. |
| 2007/0185128 A1 | 8/2007 | Conde-Frieboes et al. |
| 2007/0196503 A1 | 8/2007 | Wilson et al. |
| 2007/0275923 A1 | 11/2007 | Chen et al. |
| 2008/0145338 A1 | 6/2008 | Anderson et al. |
| 2008/0242626 A1 | 10/2008 | Zugates et al. |
| 2009/0023673 A1 | 1/2009 | Manoharan et al. |
| 2009/0221684 A1 | 9/2009 | Grinstaff et al. |
| 2009/0263407 A1 | 10/2009 | Dande et al. |
| 2009/0270481 A1 | 10/2009 | MacLachlan et al. |
| 2010/0036084 A1 | 2/2010 | Langer et al. |
| 2010/0041152 A1 | 2/2010 | Wheeler et al. |
| 2010/0178699 A1 | 7/2010 | Gao et al. |
| 2010/0240072 A1 | 9/2010 | Wester et al. |
| 2010/0331234 A1 | 12/2010 | Mahon et al. |
| 2011/0009641 A1 | 1/2011 | Anderson et al. |
| 2011/0092739 A1 | 4/2011 | Chen et al. |
| 2011/0158935 A1 | 6/2011 | Kraft |
| 2011/0200582 A1 | 8/2011 | Baryza et al. |
| 2011/0256175 A1 | 10/2011 | Hope et al. |
| 2011/0293703 A1 | 12/2011 | Mahon et al. |
| 2011/0311583 A1 | 12/2011 | Manoharan et al. |
| 2012/0009222 A1 | 1/2012 | Nguyen et al. |
| 2012/0065252 A1 | 3/2012 | Schrum et al. |
| 2012/0065358 A1 | 3/2012 | Langer et al. |
| 2012/0128760 A1 | 5/2012 | Manoharan et al. |
| 2012/0142756 A1 | 6/2012 | Guild et al. |
| 2012/0195936 A1 | 8/2012 | Rudolph et al. |
| 2012/0196923 A1 | 8/2012 | Rege et al. |
| 2012/0202871 A1 | 8/2012 | Heyes et al. |
| 2012/0214959 A1 | 8/2012 | Lee et al. |
| 2012/0237975 A1 | 9/2012 | Schrum et al. |
| 2012/0251560 A1 | 10/2012 | Dahlman et al. |
| 2012/0251618 A1 | 10/2012 | Schrum et al. |
| 2012/0328668 A1 | 12/2012 | MacLachlan et al. |
| 2013/0158021 A1 | 6/2013 | Dong et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0302401 A1 | 11/2013 | Ma et al. |
| 2013/0331464 A1 | 12/2013 | Moller et al. |
| 2014/0010861 A1 | 1/2014 | Bancel et al. |
| 2014/0044772 A1 | 2/2014 | MacLachlan et al. |
| 2014/0094399 A1 | 4/2014 | Langer et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161830 A1 | 6/2014 | Anderson et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294937 A1 | 10/2014 | MacLachlan et al. |
| 2014/0329884 A1 | 11/2014 | Dong et al. |

(56) References Cited

U.S. PATENT DOCUMENTS

| | | |
|---|---|---|
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0203439 A1 | 7/2015 | Mahon et al. |
| 2015/0265708 A1 | 9/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2015/0376144 A1 | 12/2015 | DeRosa et al. |
| 2016/0009657 A1 | 1/2016 | Anderson et al. |
| 2016/0022821 A1 | 1/2016 | Langer et al. |
| 2016/0095924 A1 | 4/2016 | Hope et al. |
| 2016/0114011 A1 | 4/2016 | Bancel et al. |
| 2016/0114042 A1 | 4/2016 | Anderson et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0137785 A1 | 5/2016 | Ma et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0213785 A1 | 7/2016 | Monoharan et al. |
| 2016/0237108 A1 | 8/2016 | Fraley et al. |
| 2016/0237134 A1 | 8/2016 | Hoge et al. |
| 2017/0342205 A1 | 11/2017 | Ratner et al. |

FOREIGN PATENT DOCUMENTS

| | | |
|---|---|---|
| CA | 2807 552 | 9/2012 |
| CN | 1399561 | 2/2003 |
| CN | 101506196 | 8/2009 |
| CN | 100569877 C | 12/2009 |
| CN | 101863544 A | 10/2010 |
| DE | 24 30 998 A1 | 1/1975 |
| DE | 25 20 814 A1 | 11/1976 |
| DE | 3701625 A1 | 8/1988 |
| DE | 3728917 A1 | 3/1989 |
| EP | 0 211 305 A2 | 2/1987 |
| EP | 6 73 637 A1 | 9/1995 |
| EP | 0959092 A1 | 11/1999 |
| EP | 1 277 829 A2 | 1/2003 |
| EP | 2045251 A1 | 4/2009 |
| EP | 1519 714 | 10/2010 |
| EP | 2338520 A1 | 6/2011 |
| EP | 2449 106 | 5/2012 |
| EP | 2532649 A1 | 12/2012 |
| EP | 2338 478 | 6/2013 |
| EP | 2823 809 | 1/2015 |
| FR | 1 378 382 A | 11/1964 |
| FR | 2 235 112 A1 | 1/1975 |
| GB | 1072118 A | 6/1967 |
| GB | 1602085 A | 11/1981 |
| JP | H07-053535 | 2/1955 |
| JP | S48-022365 | 3/1973 |
| JP | S49-127908 | 12/1974 |
| JP | S51-023537 | 2/1976 |
| JP | 51-125144 | 11/1976 |
| JP | S52-010847 | 1/1977 |
| JP | S63125144 A | 5/1988 |
| JP | 63-154788 | 6/1988 |
| JP | H06-200073 A | 7/1994 |
| JP | H06-211978 A | 8/1994 |
| JP | H09-505593 A | 6/1997 |
| JP | H10-197978 A | 7/1998 |
| JP | 11-005786 A | 1/1999 |
| JP | 11-080142 | 3/1999 |
| JP | 2001-523215 | 11/2001 |
| JP | 2002-167368 A | 6/2002 |
| JP | 2003-519199 | 6/2003 |
| JP | 4-108173 B2 | 6/2008 |
| JP | 2008-247749 A | 10/2008 |
| JP | 50-24216 B2 | 9/2012 |
| JP | 2014-001357 A | 1/2014 |
| JP | 2014-172827 | 9/2014 |
| WO | WO-1993/18229 A1 | 9/1993 |
| WO | WO-1993/18754 A1 | 9/1993 |
| WO | WO-1995/11004 A1 | 4/1995 |
| WO | WO-1995/14651 A1 | 6/1995 |
| WO | WO-1996/26179 A1 | 8/1996 |
| WO | WO-1996/36314 | 11/1996 |
| WO | WO-1997/23457 | 7/1997 |
| WO | WO-1998/16202 A2 | 4/1998 |
| WO | WO-2000/03044 | 1/2000 |
| WO | WO-2000/64484 A2 | 11/2000 |
| WO | WO-2001/05375 A1 | 1/2001 |
| WO | WO-2002/00870 A2 | 1/2002 |
| WO | WO-2002/22709 A1 | 3/2002 |
| WO | WO-2002/31025 A2 | 4/2002 |
| WO | WO-2003/040288 | 5/2003 |
| WO | WO-2003/070735 A2 | 8/2003 |
| WO | WO-2004/043588 A2 | 5/2004 |
| WO | WO-2004/048345 A2 | 6/2004 |
| WO | WO-2004/106411 A2 | 12/2004 |
| WO | WO-2005/026372 | 3/2005 |
| WO | WO-2005/028619 A2 | 3/2005 |
| WO | WO-2005/077882 A1 | 8/2005 |
| WO | WO-2005/121348 A1 | 12/2005 |
| WO | WO-2006/065266 A2 | 6/2006 |
| WO | WO-2006/082088 A1 | 8/2006 |
| WO | WO-2006/105043 A2 | 10/2006 |
| WO | WO-2009/127060 | 10/2006 |
| WO | WO-2006/138380 A2 | 12/2006 |
| WO | WO-2007/012979 | 2/2007 |
| WO | WO-2007/031091 A2 | 3/2007 |
| WO | WO-2007/096662 A2 | 8/2007 |
| WO | WO-2007/143659 A2 | 12/2007 |
| WO | WO-2008/011561 A2 | 1/2008 |
| WO | WO-2008/031157 A1 | 3/2008 |
| WO | WO-2008/113364 A2 | 9/2008 |
| WO | WO-2009/046220 A2 | 4/2009 |
| WO | WO-2009/127230 A1 | 10/2009 |
| WO | WO-2010/037408 A1 | 4/2010 |
| WO | WO-2010/042877 A1 | 4/2010 |
| WO | WO-2010/045512 A2 | 4/2010 |
| WO | WO-2010/053572 A2 | 5/2010 |
| WO | WO-2010/099387 A1 | 9/2010 |
| WO | WO-2010/114789 A1 | 10/2010 |
| WO | WO-2010/129709 A1 | 11/2010 |
| WO | WO-2011/012316 A2 | 2/2011 |
| WO | WO-2011/012746 A2 | 2/2011 |
| WO | WO-2011/039144 A1 | 4/2011 |
| WO | WO-2011/068810 A1 | 6/2011 |
| WO | WO-2011/141705 A1 | 11/2011 |
| WO | WO-2012/019168 | 2/2012 |
| WO | WO-2012/027675 A2 | 3/2012 |
| WO | WO-2012/133737 A1 | 10/2012 |
| WO | WO-2012/135025 A2 | 10/2012 |
| WO | WO-2012/135805 | 10/2012 |
| WO | WO-2012/170889 A1 | 12/2012 |
| WO | WO-2012/170930 A1 | 12/2012 |
| WO | WO-2013/039857 | 3/2013 |
| WO | WO-2013/039861 | 3/2013 |
| WO | WO-2013/063468 A1 | 5/2013 |
| WO | WO-2013/090186 | 6/2013 |
| WO | WO-2013/101690 | 7/2013 |
| WO | WO-2013/126803 | 8/2013 |
| WO | WO-2013/130161 A1 | 9/2013 |
| WO | WO-2013/151663 A1 | 10/2013 |
| WO | WO-2013/151664 A1 | 10/2013 |

(56) References Cited

FOREIGN PATENT DOCUMENTS

| WO | WO-2013/151666 A2 | 10/2013 |
|---|---|---|
| WO | WO-2013/151667 A1 | 10/2013 |
| WO | WO-2013/151668 A2 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2014/028487 A1 | 2/2014 |
| WO | WO-2014/113089 A2 | 7/2014 |
| WO | WO-2014/144039 | 9/2014 |
| WO | WO-2014/144711 | 9/2014 |
| WO | WO-2014/144767 | 9/2014 |
| WO | WO-2014/152027 | 9/2014 |
| WO | WO-2014/152030 | 9/2014 |
| WO | WO-2014/152031 | 9/2014 |
| WO | WO-2014/152211 | 9/2014 |
| WO | WO-2014/152540 | 9/2014 |
| WO | WO-2014/158795 | 10/2014 |
| WO | WO-2014/159813 | 10/2014 |
| WO | WO-2014/179562 A1 | 11/2014 |
| WO | WO-2014/210356 A1 | 12/2014 |
| WO | WO-2015/006747 A2 | 1/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/058069 A1 | 4/2015 |
| WO | WO-2015/184256 A2 | 12/2015 |
| WO | WO-2015/011633 | 1/2016 |
| WO | WO-2016/054421 | 4/2016 |
| WO | WO-2016/071857 | 5/2016 |
| WO | WO-2016/077123 | 5/2016 |
| WO | WO-2016/077125 | 5/2016 |
| WO | WO-2016/118724 | 7/2016 |
| WO | WO-2016/118725 | 7/2016 |
| WO | WO-2019/207060 | 10/2019 |

OTHER PUBLICATIONS

U.S. Appl. No. 61/494,881.
U.S. Appl. No. 61/494,882.
Adami, R.C. et al., An amino acid-based amphoteric liposomal delivery system for systemic administration of siRNA. Molecular Therapy 19(6):1141-1151 (2011).
Akinc et al., Parallel synthesis and biophysical characterization of a degradable polymer library for gene delivery. J Am Chem Soc. May 7, 2003;125(18):5316-23.
Akinc, A. et al., A combinatorial library of lipid-like materials for delivery of RNAi therapeutics. Nature Biotechnology 26(5):561-569 (2008).
Akinc, A. et al., Development of lipidoid-siRNA formulations for systemic delivery to the liver. Molecular Therapy 17(5):872-879 (2009).
Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, 3(5), (2016).
Anderson, D.G. et al., Structure/property studies of polymeric gene delivery using a library of poly(beta-amino esters). Molecular Therapy 11(3):426-434 (2005).
Anderson, J. Biological Responses to Materials. Annual Review of Materials Research 31:81-110 (2001).
Anderson, W. French, Human gene therapy, Nature, 392, 25-30 (1998).
Asokan et al., Cytosolic delivery of macromolecules. 3. Synthesis and characterization of acid-sensitive bis-detergents. Bioconjug Chem. Nov.-Dec. 2004;15(6):1166-73.
Bajaj, A. et al., Synthesis and gene transfection efficacies of PEI-cholesterol-based lipopolymers. Bioconjugate Chemistry 19(8):1640-516511 (2008).
Behr, J.P. et al., Efficient gene transfer into mammalian primary endocrine cells with lipopolyamine-coated DNA, Proceedings of the National Academy of Sciences USA, 86(18):6982-6986 (1989).

Bloomfield, VA, Quasi-elastic light scattering applications in biochemistry and biology, Annual Review of Biophysics and Bioengineering, 10:421-450 (1981).
Bourque et al., Hydroformylation Reactions Using Recyclable Rhodium-Complexed Dendrimers on Silica. J Am Chem Soc. 2000;122(5):956-957.
Boussif, O. et al., A versatile vector for gene and oligonucleotide transfer into cells in culture and in vivo: polyethylenimine. Proceedings of the National Academy of Sciences of the USA. 92(16):7297-7301 (1995).
Braun, C.S. et al., Structure/function relationships of polyamidoamine/DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the USA. 104(36):14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).
Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3)731-741 (2007).
Budker, V. et al., Protein/Amphipathic Polyamine Complexes Enable Highly Efficient Transfection with Minimal Toxicity, BioTechniques, 23:139-147 (1997).
Burnett, J.C. et al., Current progress of siRNA/shRNA therapeutics in clinical trials. Biotechnology Journal 6(9):1130-1146 (2011).
Byk, G. et al., Synthesis, activity, and structure-activity relationship studies of novel cationic lipids for DNA transfer. Journal of Medical Chemistry 41(2):224-235 (1998).
Caplen, N.J. et al., In vitro liposome-mediated DNA transfection of epithelial cell lines using the cationic liposome DC-Chol/DOPE, Gene Therapy, 2:603-613 (1995).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).
Chiang et al., Synthesis, characterization and properties of novel self-extinguishing organic-inorganic nanocomposites containing nitrogen, silicon and phosphorus via sol-gel method. Composite Science and Technology. 2008;68(14):2849-57.
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Cotton, M. et al., Receptor-mediated transport of DNA into eukaryotic cells. Methods in Enzymology 217 (H):618-644 (1993).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysica Acta 1489(1):31-44. Review (1999).
Crystal, R.G. Transfer of genes to humans: early lessons and obstacles to success. Science 270(5235):404-410. Review (1995).
Cullis et al., "Lipid Nanoparticle systems for enabling gene therapies", Molecular Therapy, vol. 25(7), 1467-1475, (2017).

(56) References Cited

OTHER PUBLICATIONS

Damen, M. et al., Delivery of DNA and siRNA by novel gemini-like amphiphilic peptides. Journal of Controlled Release 145(1):33-39 (2010).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Decher, G. Fuzzy Nanoassemblies: Toward Layered Polymeric Multicomposites. Science 277: 1232-1237 (1997).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N",N'"-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M. and Huang, L., Liposome and polylysine mediated gene therapy. New Journal of Chemistry 21:113-124 (1997).
Discher, B.M. et al., Polymersomes: tough vesicles made from diblock copolymers. Science 284(5417):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).
Elbashir, S.M. et al., RNA interference is mediated by 21- and 22-nucleotide RNAs. Genes & Development 15: 188-200 (2001).
Ewert, K. et al., Cationic lipid-DNA complexes for gene therapy: understanding the relationship between complex structure and gene delivery pathways at the molecular level. Current Medicinal Chemistry 11(2): 133-149 (2004).
Extended European Search Report corresponding to European Patent Application No. 15799261.1 (dated Mar. 9, 2018).
Fechter, P. and Brownlee, G.G., Recognition of mRNA cap structures by viral and cellular proteins, Journal of General Virology, 86(Pt 5):1239-1249 (2005).
Felgner, P.L. et al., Lipofection: a highly efficient, lipid-mediated DNA-transfection procedure, Proceedings of the National Academy of Sciences USA, 84(21):7413-7417 (1987).
Fenske, D.B. and Cullis, P., Liposomal nanomedicines. Expert Opinion on Drug Delivery 5(1):25-44 (2008).
Ferruti, P.F. and Barbucci, R. , Linear amino polymers: Synthesis, protonation and complex formation. Advances in Polymer Science 58:55-92 (1984).
Ferruti, P.F. et al., A novel modification of poly(l-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391 (6669):806-811 (1998).
Fourneau et al., Two new series of local anesthetics derived from piperazine. Bulletin de la Societe Chimique de France. 1930;47:1003-16. French.
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).
Gao, X. and Huang, L., A novel cationic liposome reagent for efficient transfection of mammalian cells, Biochemical and Biophysical Research Communications, 179(1):280-285(1991).
Giuliani et al., Beyond natural antimicrobial peptides: multimeric peptides and other peptidomimetic approaches. Cell Mol Life Sci. Jul. 2011;68(13):2255-66. doi: 10.1007/S00018-0I 1-0717-3. Epub May 20, 2011.
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA, 10(9):1479-1487 (2004).
Grudzien-Nogalska, E. et al., Phosphorothioate cap analogs stabilize mRNA and increase translational efficiency in mammalian cells, RNA, 13(10):1745-1755 (2007).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Guan et al., "Nanotechnologies in delivery of mRNA therapeutics using nonviral vector-based delivery systems", Gene Therapy, vol. 24, 133-143 (2017).
Gupta, U. et al., A review of in vitro-in vivo investigations on dendrimers: the novel nanoscopic drug carriers. Nanomedicine: Nanotechnology, Biology, and Medicine 2(2):66-73 (2006).
Gust, T.C. et al., RNA-containing adenovirus/polyethylenimine transfer complexes effectively transduce dendritic cells and induce antigen-specific T cell responses, The Journal of Gene Medicine, 6(4): 464-470 (2004).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Hayashi, Yoshio et al., "Analysis of Amide Bond Formation with an $\alpha$-Hydroxy-$\beta$-amino Acid Derivative, 3-Amino-2-hydroxy-4-phenylbutanoic Acid, as an Acyl Component: Byproduction of Homobislactone", J. Org. Chem., 66(16): 5537-5544 (2001).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Heyes, J. et al., Cationic lipid saturation influences intracellular delivery of encapsulated nucleic acids, Journal of Controlled Release, 107(2):276-287 (2005).
Hill, I.R.C. et al., In vitro cytotoxicity of poly(amidoamine)s: relevance to DNA delivery. Biochimica et Biophysica Acta 1427: 161-174 (1999).
Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hofland, H.E.J et al., Formation of stable cationic lipid/DNA complexes for gene transfer. Proceedings of the National Academy of Sciences of the USA 93 (14): 7305-7309 (1996).
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Howard, K.A. Delivery of RNA interference therapeutics using polycation-based nanoparticles. Advanced Drug Delivery Reviews 61: 710-720 (2009).
Hsu et al., Diethanolamine (DEA) degradation under gas-treating conditions. Industrial and Engineering Chemistry Product Research and Development. 1985;24(4):630-35.
Huang, Z. et al., Thiocholesterol-Based Lipids for Ordered Assembly of Bioresponsive Gene Carriers, Molecular Therapy, 11(3):409-417 (2005).
Ichimaru et al., Synthesis and characterization of new piperazine-type inhibitors for mitochondrial NADH-ubiquinone oxidoreductase (complex I). Biochemistry. Oct. 7, 2008;47(40):10816-26.

(56) References Cited

OTHER PUBLICATIONS

Ikeda et al., Role of micafungin in the antifungal armamentarium. Curr Med Chem. 2007;14(11):1263-75.

Incani, V. et al., Lipid and hydrophobic modification of cationic carriers on route to superior gene vectors. Soft Matter 6: 2124-2138 (2010).

Jemielity, J. et al., Novel "anti-reverse" cap analogs with superior translational properties, RNA, 9(9):1108-1122 (2003).

Jiang, G. et al., Hyaluronic acid-polyethyleneimine conjugate for target specific intracellular delivery of siRNA. Biopolymers 89 (7): 635-642 (2008).

Jiang, M. et al., Electrochemically controlled release of lipid/DNA complexes: a new tool for synthetic gene delivery system. Electrochemistry Communications (6): 576-582 (2004).

Jiang, S. and Cao, Z., Ultralow-fouling, functionalizable, and hydrolyzable zwitterionic materials and their derivatives for biological applications. Advanced Materials 22(9):920-932 (2010).

Jolck, R.I. et al., Solid-phase synthesis of PEGylated lipopeptides using click chemistry. Bioconjugate Chemistry 21 (5):807-810 (2010).

Jon, S et al., Degradable poly(amino alcohol esters) as potential DNA vectors with low cytotoxicity. Biomacromolecules 4(6):1759-1762 (2003).

Juliano et al., Biological barriers to therapy with antisense and siRNA oligonucleotides. Mol Pharm. May-Jun. 2009;6(3):686-95. doi: 10.1021/mp900093r.

Kabanov, A.V. and Kabanov, V.A., DNA complexes with polycations for the delivery of genetic material into cells. Bioconjugate Chemistry 6(1): 7-20 (1995).

Kamath, S. et al., Surface chemistry influences implant-mediated host tissue responses. Journal of Biomedical Materials Research A 86(3):617-626 (2007).

Kanetani et al., Synthesis, and physicochemical and antimicrobial properties of 3-(3-alkyl-1-piperazinyl)-1-propanesulfonic acids and some related compounds. Nippon Kagaku Kaishi.1983(12):1783-91.

Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).

Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).

Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).

Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).

Klibanov, A.L. et al., Amphipathic polyethylenglycols effectively prolong the circulation time of lipsosomes, FEBS Letters, 268(1):235-237 (1990).

Kozak, M. An analysis of 5'-noncoding sequences from 699 vertebrate messenger RNAs, Nucleic Acid Research, 15(20):8125-8148 (1987).

Lasic, D.D. et al., Gelation of liposome interior. A novel method for drug encapsulation, FEBS Letters, 312(2-3):255-258 (1992).

Lee, S. et al., Stability and cellular uptake of polymerized siRNA (poly-siRNA)/polyethylenimine (PEI) complexes for efficient gene silencing. Journal of Controlled Release 141: 339-346 (2010).

Lee et al., "Programming Human Dendritic Cells with mRNA", Methods in Molecular Biology, vol. 969, 111-125 (2013).

Leuschner et al., Therapeutic siRNA silencing in inflammatory monocytes in mice. Nat Biotechnol. Oct. 9, 2011;29(11):1005-10. doi: 10.1038/nbt.1989.

Li, S. et al., In vivo gene transfer via intravenous administration of cationic lipid-protamine-DNA (LPD) complexes, Gene Therapy, 4:891-900 (1997).

Li, W. et al., Lipid-based Nanoparticles for Nucleic Acid Delivery, Pharmaceutical Research, 24(3):438-449 (2007).

Lim, Y. et al., A self-destroying polycationic polymer: biodegradable poly(4-hydroxy-I-proline ester). Journal of American Chemical Society 121: 5633-5639 (1999).

Love, K.T. et al., Lipid-like materials for low-dose in vivo gene silencing, Proceedings of the National Academy of Sciences USA, 107(5):1864-1869 (2010).

Lubke, T. et al., Proteomics of the Lysosome, Biochimica et Biophysica Acta, 1793(4):625-635 (2009).

Lukyanov, A.N. and Torchilin, V.P., Micelles from lipid derivatives of water-soluble polymers as delivery systems for poorly soluble drugs. Advanced Drug Delivery Reviews 56: 1273-1289 (2004).

Luo, D. and Saltzman, M., Synthetic DNA delivery systems. Nature Biotechnology 18: 33-37. Review (2000).

Lynn, D.M. et al., Accelerated discovery of synthetic transfection vectors: parallel synthesis and screening of a degradable polymer library. Journal of American Chemical Society 123 (33): 8155-8156 (2001).

Lynn, D.M. et al., Degradable Poly($\beta$-amino esters): Synthesis, Characterization, and Self-Assembly with Plasmid DNA. Journal of American Chemical Society 122(44): 10761-10768 (2000).

Lynn, D.M. et al., pH-Responsive Polymer Microspheres: Rapid Release of Encapsulated Material within the Range of Intracellular pH. Angewandte Chemie International Edition 40(9): 1707-1710 (2001).

Ma, M. et al., Development of Cationic Polymer Coatings to Regulate Foreign Body Responses. Advanced Healthcare Materials 23: H189-H194. Reviews (2011).

Margus, H. et al., Cell-penetrating peptides as versatile vehicles for oligonucleotide delivery. Molecular Therapy 20 (3): 525-533 (2012).

Martell, A.E. and Chaberek, S., The Preparation and the Properties of Some N,N'-Disubstituted-ethylenediaminedipropionic Acids. Journal of the American Chemical Society 72:5357-5361 (1950).

Mathiowitz, E. and Langer, R., Polyanhydride microspheres as drug carriers I. Hot-melt microencapsulation. Journal of Controlled Release 5: 13-22 (1987).

Mathiowitz, E. et al., Novel microcapsules for delivery systems. Reactive Polymers 6: 275-283 (1987).

Mathiowitz, E. et al., Polyanhydride microspheres as drug carriers II. Microencapsulation by solvent removal. Journal of Applied Polymer Sciences 35: 755-774 (1988).

Mendelsohn, J.D. et al., Rational design of cytophilic and cytophobic polyelectrolyte multilayer thin films. Biomacromolecules 4(1): 96-106 (2003).

Meng et al., "A new developing class of gene delivery: messenger RNA-based therapeutics", Biomaterials Science, vol. 5, 2381-2392, (2017).

Miller, A. Cationic Liposomes for Gene Therapy. Angewandte Chemie International Edition 37: 1768-1785 (1998).

Mintzer et al., Nonviral vectors for gene delivery. Chem Rev. Feb. 2009;109(2):259-302.

Morrissey, D. et al., Potent and persistent in vivo anti-HBV activity of chemically modified siRNAs, Nature Biotechnology, 23(8):1002-1007 (2005).

Moure et al., Chem. Eur. J. (2001) 17:7927-7939.

Narang, A.S. et al., Cationic lipids with increased DNA binding affinity for nonviral gene transfer in dividing and nondividing cells. Bioconjugate Chemistry 16(1): 156-168 (2005).

Navarro, G. et al., Phospholipid-polyethylenimine conjugate-based micelle-like nanoparticles for siRNA delivery. Drug Delivery and Translational Research 1: 25-33 (2011).

Neamnark, A. et al., Aliphatic lipid substitution on 2 kDa polyethylenimine improves plasmid delivery and transgene expression. Molecular Pharmaceutics 6(6): 1798-1815 (2009).

Ng, J. et al., LincRNAs join the pluripotency alliance, Nature Genetics, 42:1035-1036 (2010).

Nguyen, D.N. et al., A novel high-throughput cell-based method for integrated quantification of type I interferons and in vitro screening

(56) References Cited

OTHER PUBLICATIONS of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nori, A. et al., Tat-conjugated synthetic macromolecules facilitate cytoplasmic drug delivery to human ovarian carcinoma cells, Bioconj. Chem., 14(1): 44-50 (2003).
Parrish, D.A. and Mathias, L.J., Five- and six-membered ring opening of pyroglutamic diketopiperazine. Journal of Organic Chemistry 67(6): 1820-1826 (2002).
Peer et al., Nanocarriers as an emerging platform for cancer therapy. Nat Nanotechnol. Dec. 2007;2(12):751-60. doi: 10.1038/nnano.2007.387.
Peppas, N.A. et al., Hydrogels in Biology and Medicine: From Molecular Principles to Bionanotechnology. Advanced Materials 18:1345-1360 (2006).
Philipp, A. et al., Hydrophobically modified oligoethylenimines as highly efficient transfection agents for siRNA delivery. Bioconjugate Chemistry 20(11): 2055-2061 (2009).
Pons, M. et al., Liposomes obtained by the ethanol injection method, International Journal of Pharmacology, 95:51-56 (1993).
Prata, C.A. et al., Lipophilic peptides for gene delivery. Bioconjugate Chemistry 19(2): 418-420 (2008).
Putnam, D. Polymers for gene delivery across length scales. Nature Materials 5: 439-451 (2006).
Putnam, D. and Langer, R., Poly(4-hydroxy-I-proline ester): Low-Temperature Polycondensation and Plasmid DNA Complexation. Macromolecules 32(11): 3658-3662 (1999).
Ratner, B.D. and Bryant, S., Biomaterials: where we have been and where we are going. Annual Review of Biomedical Engineering 6: 41-75 (2004).
Rogers et al., Biochemistry (1964), 3(12), 1850-5.
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31:183-201 (2001).
Scheel et al., Therapeutic anti-tumor immunity triggered by injections of immunostimulating single-stranded RNA. Eur J Immunol. Oct. 2006;36(10):2807-16.
Schöberl, Alfons et al., "Über die Dehydratisierung von Thioglykolsäure, deren Kondensationspolymere und über Dithioglykolid", Justus Liebigs Ann. Chem., 595: 101-130 (1995).
Semple,S.C. et al., Rational Design of Cationic Lipids for siRNA Delivery, Nature Biotechnology, 28(2):172-176 (2010).
Sen et al., Surfactin: biosynthesis, genetics and potential applications. Adv Exp Med Biol. 2010;672:316-23.
Shchori E., Poly(secondary Amine)s from Diacrylates and Diamines. Journal of Polymer Science 21 (6):413-15 (1983).
Sherwood, R.F. Advanced drug delivery reviews: enzyme prodrug therapy, Adv. Drug Del. Rev., 22: 269-288 (1996).
Siegwart, D.J. et al., Combinatorial synthesis of chemically diverse core-shell nanoparticles for intracellular delivery. Proceedings of the National Academy of the Sciences of the USA 108(32):12996-123001 (2011).
Stern, L. et al., A novel antitumor prodrug platform designed to be cleaved by the endoprotease legumain, Bioconj. Chem., 20: 500-510 (2009).
STN-CAS database Registry No. 1067642-37-8. Entered STN-CAS database on Oct. 29, 2008.
Swali et al., Solid-Phase Dendrimer Synthesis and the Generation of Super-High-Loading Resin Beads for Combinatorial Chemistry. J Org Chem Am Chem Soc. 1997;62:4902-03.
Szoka, F. and Papahadjopoulos, D., Comparative properties and methods of preparation of lipid vesicles (liposomes). Annual Review of Biophysics Bioengineering 9: 467-508 (1980).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Thiel et al., Therapeutic applications of DNA and RNA aptamers. Oligonucleotides. Sep. 2009;19(3):209-22. doi: 10.1089/oli.2009.0199.
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsvetkov, D.E. et al., Neoglycoconjugates based on dendrimeric poly(aminoamides). Russian Journal of Bioorganic Chemistry 28(6): 470-486 (2002).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).
Van De Wetering, P. et al., Structure-activity relationships of water-soluble cationic methacrylate/methacrylamide polymers for nonviral gene delivery. Bioconjugate Chemistry 10(4): 589-597 (1999).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Viega et al., "Cell specific delivery of modified mRNA expressing therapeutic proteins to leukocytes", Nature Communications, 1-6, (2018).
Von Harpe et al., Characterization of commercially available and synthesized polyethylenimines for gene delivery. Journal of Controlled Release 69(2):309-322 (2000).
Walde, P. et al., Preparation of Vesicles (Liposomes). Encyclopedia of Nanoscience and Nanotechnology. Nalwa, ed. American Scientific Publishers, Los Angeles 9:43-79 (2004).
Weinstein et al., RNAi nanomedicines: challenges and opportunities within the immune system. Nanotechnology. Jun. 11, 2010;21(23):232001. doi: 10.1088/0957-4484/21/23/232001. Epub May 13, 2010.
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al., Reducible cationic lipids for gene transfer, Biochem. J., 356:747-756 (2001).
White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10,11-epoxyundecanoicacid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).

(56) References Cited

OTHER PUBLICATIONS

Wu, J. et al., Cationic lipid polymerization as a novel approach for constructing new DNA delivery agents. Bioconjugate Chemistry 12(2): 251-257 (2001).

Yokoe, H. and Meyer, T., Spatial Dynamics of GFP-tagged proteins investigated by local fluorescence enhancement, Nature Biotechnology, 14(10):1252-1256 (1996).

Yoneda et al., A cell-penetrating peptidic GRP78 ligand for tumor cell-specific prodrug therapy, Bioorg. Med. Chern. Lett., 18(5): 1632-1636 (2008).

Yoshioka, Y. and Calvert, P., Epoxy-based Electroactive Polymer Gels. Experimental Mechanics 42(4): 404-408 (2002).

Zagridullin, P.H. et al., Monobasic amines. II. Cycloalkylation and hydroxyalkylation of cyclic and acyclic di- and polyamines. Journal of Organic Chemistry26(1):184-88. Russian (1990).

Zamora et al., RNA interference therapy in lung transplant patients infected with respiratory syncytial virus. Am J Respir Crit Care Med. Feb. 15, 2011;183(4):531-8. doi: 10.1164/rccm.201003-04220C. Epub Sep. 17, 2010.

Zaugg, H.E. et al., 3-Carboxy-2,5-piperazinedione and Derivatives. Journal of American Chemical Society 78(11):2626-2631 (1956).

Zauner, W. et al., Polylysine-based transfection systems utilizing receptor-mediated delivery. Advanced Drug Delivery Reviews 30(1-3):97-113(1998).

Zintchenko, A. et al., Simple modifications of branched PEI lead to highly efficient siRNA carriers with low toxicity. Bioconjugate Chemistry 19(7):1448-1455 (2008).

International Search Report for PCT/US2015/033173, dated Nov. 12, 2015.

\* cited by examiner

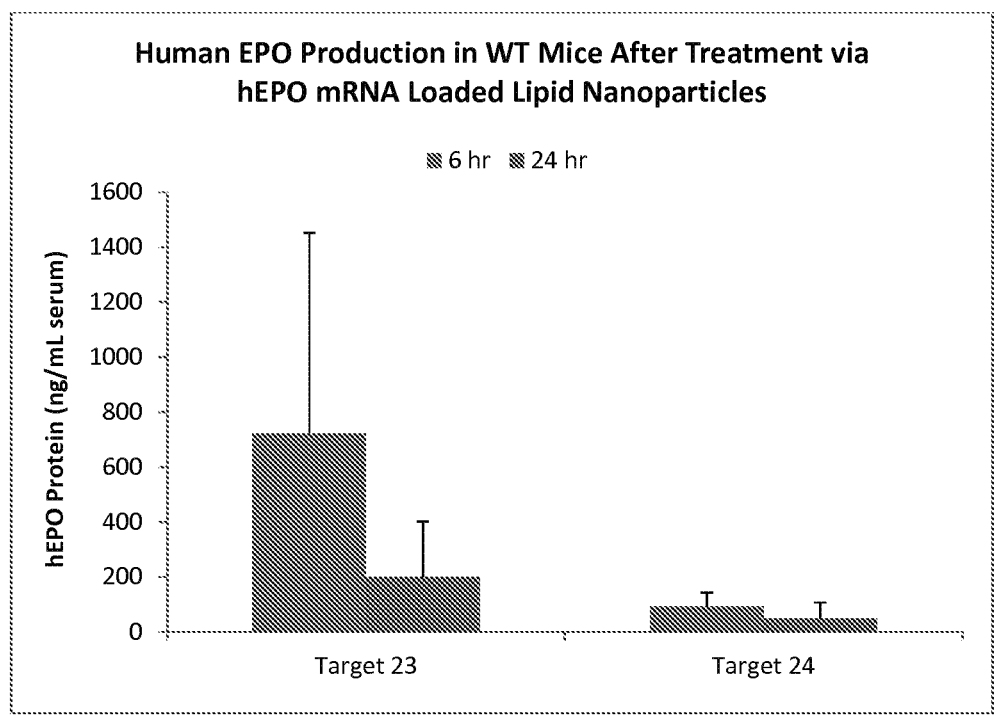

SEQUENCE LISTING

<160> NUMBER OF SEQ ID NOS: 4

<210> SEQ ID NO 1
<211> LENGTH: 1898
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1794)..(1794)
<223> OTHER INFORMATION: May or may not be present

<400> SEQUENCE: 1
ggacagaucg ccuggagacg ccauccacgc uguuuugacc uccauagaag acaccgggac      60

```
cgauccagcc uccgcggccg ggaacggugc auuggaacgc ggauuccccg ugccaagagu    120
gacucaccgu ccuugacacg auggaagaug ccaaaaacau uaagaagggc ccagcgccau    180
ucuacccacu cgaagacggg accgccggcg agcagcugca caaagccaug aagcgcuacg    240
cccuggugcc cggcaccauc gccuuuaccg acgcacauau cgagguggac auuaccuacg    300
ccgaguacuu cgagaugagc guucggcugg cagaagcuau gaagcgcuau gggcugaaua    360
caaaccaucg gaucguggug ugcagcgaga auagcuugca guucuucaug cccguguugg    420
gugcccuguu caucggugug gcuguggccc cagcuaacga caucuacaac gagcgcgagc    480
ugcugaacag caugggcauc agccagccca ccgucguauu cgugagcaag aaagggcugc    540
aaaagauccu caacgugcaa aagaagcuac cgaucauaca aaagaucauc aucauggaua    600
gcaagaccga cuaccagggc uuccaaagca uguacaccuu cgugacuccc cauuugccac    660
ccggcuucaa cgaguacgac uucgugcccg agagcuucga ccgggacaaa accaucgccc    720
ugaucaugaa caguagugcc aguaccggau ugcccaaggg cguagcccua ccgcaccgca    780
ccgcuugugu ccgauucagu caugcccgcg accccaucuu cggcaaccag aucaucccg    840 acaccgcuau cccagcgug gugccauuuc accggcuu cggcauguuc accacgcugg    900
gcuacuugau cugcggcuuu cgggucgugc ucauguaccg cuucgaggag gagcuauucu    960
ugcgcagcuu gcaagacuau aagauucaau cugcccugcu ggugcccaca cuauuuagcu   1020
ucuucgcuaa gagcacucuc aucgacaagu acgaccuaag caacuugcac gagaucgcca   1080
gcggcggggc ccgcucagc aaggagguag gugaggccgu ggccaaacgc uuccaccuac   1140
caggcauccg ccagggcuac ggccugacag aaacaaccag cgccauucug aucaccccg    1200 aaggggacga caagccuggc gcaguaggca aggugugcc cuucuucgag gcuaaggugg   1260
uggacuugga caccgguaag acacugggug ugaaccagcg cggcgagcug ugcguccgug   1320
gccccaugau caugagcggc uacguuaaca ccccgaggc uacaaacgcu cucaucgaca   1380
aggacggcug gcugcacagc ggcgacaucg ccuacuggga cgaggacgag cacuucuuca   1440
ucguggaccg gcugaagagc cugaucaaau acaagggcua ccaguagcc ccagccgaac   1500 uggagagcau ccugcugcaa caccccaaca ucuucgacgc cggggucgcc ggccugcccg   1560
acgacgaugc cggcgagcug cccgccgcag ucgucgugcu ggaacacggu aaaaccauga   1620
ccgagaagga gaucguggac uaugugccga gccagguuaa accgccaag aagcugcgcg   1680 guggugugu guucguggac gaggugccua aggacugac cggcaaguug gacgcccgca   1740
agauccgcga gauucucauu aaggccaaga agggcggcaa gaucgccgug uacgggugg   1800 cauccccgug accccucccc agugccucuc cuggcccugg aaguugccac uccagugccc   1860
accagccuug uccaauaaaa auuaaguugc aucaagcu                           1898
```

<210> SEQ ID NO 2
<211> LENGTH: 140
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 2

```
ggacagaucg ccuggagacg ccauccacgc uguuugacc uccauagaag acaccgggac      60
cgauccagcc uccgcggccg ggaacggugc auuggaacgc ggauuccccg ugccaagagu    120
gacucaccgu ccuugacacg                                                140
```

```
<210> SEQ ID NO 3
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
cggguggcau cccugugacc ccuccccagu gccucuccug gcccuggaag uugccacucc      60
agugcccacc agccuugucc uaauaaaauu aaguugcauc aagcu                    105

<210> SEQ ID NO 4
<211> LENGTH: 104
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4 gggguggcauc ccugugaccc cuccccagug ccucuccugg cccuggaagu ugccacucca    60
gugcccacca gccuuguccu aauaaaauua aguugcauca agcu                    104
```

BIODEGRADABLE LIPIDS FOR DELIVERY OF NUCLEIC ACIDS

CROSS-REFERENCE TO RELATED APPLICATIONS

This application is a continuation application of U.S. application Ser. No. 16/692,846, filed Nov. 22, 2019, which is a continuation of U.S. application Ser. No. 16/002,878, filed Jun. 7, 2018, which is a divisional of U.S. application Ser. No. 15/314,818, filed Nov. 29, 2016, which is the U.S. National Stage of International Application No. PCT/US2015/033173, filed May 29, 2015, which claims priority under 35 U.S.C § 119(e) to U.S. Provisional Application No. 62/005,266, filed on May 30, 2014, the disclosures of which are incorporated herein by reference in their entirety.

BACKGROUND

The delivery of agents, such as nucleic acids, has been explored extensively as a potential therapeutic option for certain disease states. In particular, RNA interference (RNAi) has been the subject of significant research and clinical development. Lately, messenger RNA (mRNA) therapy has become an increasingly important option for treatment of various diseases, in particular, for those associated with deficiency of one or more proteins.

SUMMARY OF THE INVENTION

The present invention provides, among other things, a novel class of lipid compounds for improved in vivo delivery of therapeutic agents, such as nucleic acids. In particular, the compounds provided by the present invention are biodegradable in nature and are particularly useful for delivery of mRNA and other nucleic acids for therapeutic uses. It is contemplated that the compounds provided herein are capable of highly effective in vivo delivery while maintaining favorable toxicity profile due to the biodegradable nature.

In one aspect, the present invention provides a compound (i.e., cationic lipid) of formula I:

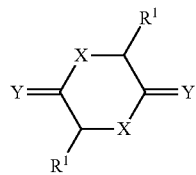

or a pharmaceutically acceptable salt thereof,
wherein:
each X independently is O or S;
each Y independently is O or S; and
each $R^1$ independently is defined herein.

In some embodiments, the compound of formula I is of formula II:

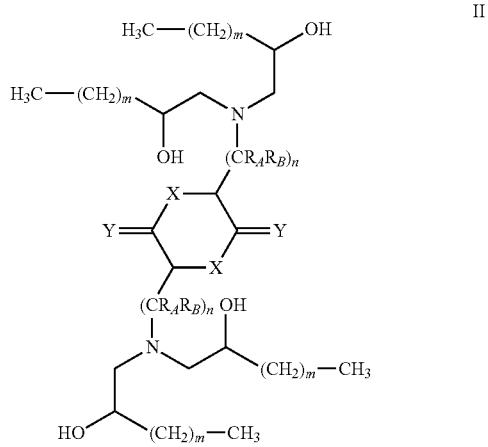

or a pharmaceutically acceptable salt thereof,
wherein:
each X independently is O or S;
each Y independently is O or S;
each m independently is 0 to 20;
each n independently is 1 to 6;
each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen, and
each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen.

In some embodiments, the compound has a structure of formula III (i.e., Target 23 or T23):

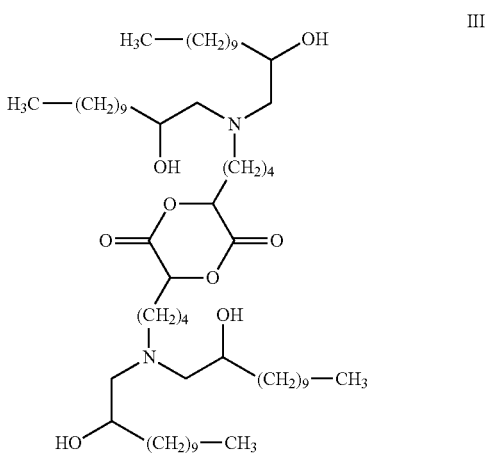

or a pharmaceutically acceptable salt thereof.

In some embodiments, a compound of formula II is a compound of formula IV (i.e., Target 24 or T24):

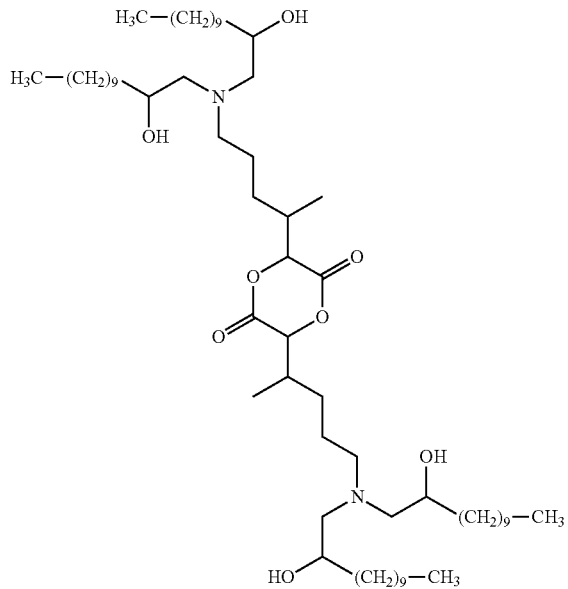

or a pharmaceutically acceptable salt thereof.

In some embodiments, a compound of formula II is a compound of formula V:

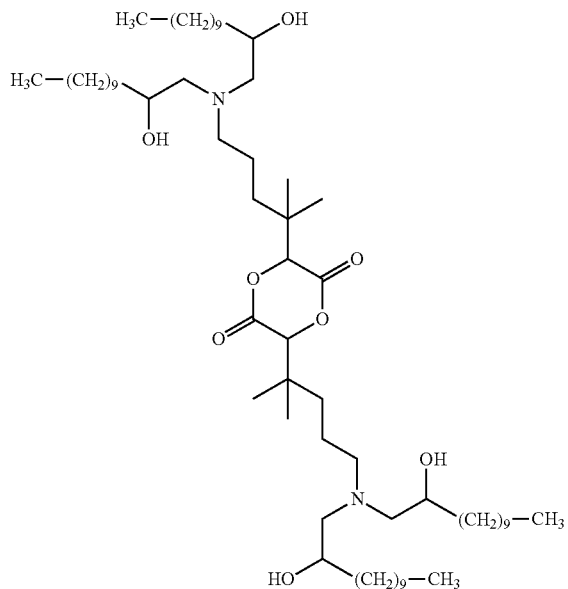

or a pharmaceutically acceptable salt thereof.

In another aspect, the invention provides a composition, such as a lipid nanoparticle (e.g., liposome), comprising one or more of the compounds (i.e., cationic lipids) of formula I, formula II, formula III, formula IV, formula V or a sub-formula thereof.

In some embodiments, a suitable composition of the present invention is a liposome. In some embodiments, a suitable liposome comprises one or more cationic lipids of formula I, formula II, formula III, formula IV, formula V or a sub-formula thereof. In particular embodiments, a suitable liposome comprises a cationic lipid of formula III. In particular embodiments, a suitable liposome comprises a cationic lipid of formula IV. In particular embodiments, a suitable liposome comprises a cationic lipid of formula V.

In some embodiments, a suitable liposome further comprises one or more non-cationic lipids, one or more cholesterol-based lipids and/or one or more PEG-modified lipids. In some embodiments, the one or more non-cationic lipids are selected from distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoylphosphatidyl-ethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, a suitable liposome further comprises one or more cholesterol-based lipids. In some embodiments, the one or more cholesterol-based lipids are selected from cholesterol, PEGylated cholesterol and DC-Chol (N,N-dimethyl-N-ethylcarboxamidocholesterol), 1,4-bis(3-N-oleylamino-propyl)piperazine.

In some embodiments, a suitable liposome further comprises one or more PEG-modified lipids. In some embodiments, the one or more PEG-modified lipids comprise a poly(ethylene) glycol chain of up to 5 kDa in length covalently attached to a lipid with alkyl chain(s) of $C_6$-$C_{20}$ length. In some embodiments, a PEG-modified lipid is a derivatized ceramide such as N-Octanoyl-Sphingosine-1-[Succinyl(Methoxy Polyethylene Glycol)-2000]. In some embodiments, a PEG-modified or PEGylated lipid is PEGylated cholesterol or Dimyristoylglycerol (DMG)-PEG-2K.

In some embodiments, a suitable liposome comprises the compound of Formula III, DOPE, cholesterol and DMG-PEG2K.

In some embodiments, a suitable liposome has a size of or less than about 500 nm, 450 nm, 400 nm, 350 nm, 300 nm, 250 nm, 200 nm, 150 nm, 125 nm, 110 nm, 100 nm, 95 nm, 90 nm, 85 nm, 80 nm, 75 nm, 70 nm, 65 nm, 60 nm, 55 nm, or 50 nm.

In some embodiments, a liposome according to the present invention comprises an mRNA encoding a protein encapsulated therein.

In yet another aspect, the present invention provides methods of delivering a therapeutic agent, such as a nucleic acid (e.g., DNA, siRNA, mRNA, microRNA) using a composition (e.g., liposome) described herein. In still another aspect, the present invention provides methods of treating a disease or disorder including administering to subject in need of treatment a composition (e.g., liposome) comprising a therapeutic agent, such as a nucleic acid (e.g., DNA, siRNA, mRNA, microRNA).

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes

BRIEF DESCRIPTION OF THE DRAWING

Illustrated in FIG. 1 are human EPO levels in wild type mouse sera after treatment via hEPO mRNA loaded LNPs. Treatment after 6 hours is shown in the bars at right. Treatment after 24 hours is shown in the bars at left.

DEFINITIONS

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Chemical Definitions

Definitions of specific functional groups and chemical terms are described in more detail below. The chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry,* 5th Edition, John Wiley & Sons, Inc., New York, 2001; Larock, *Comprehensive Organic Transformations,* VCH Publishers, Inc., New York, 1989; and Carruthers, *Some Modern Methods of Organic Synthesis,* 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high performance liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally contemplates compounds as individual isomers substantially free of other isomers, and alternatively, as mixtures of various isomers.

When a range of values is listed, it is intended to encompass each value and sub-range within the range. For example "C1-6 alkyl" is intended to encompass, C1, C2, C3, C4, C5, C6, C1-6, C1-5, C1-4, C1-3, C1-2, C2-6, C2-5, C2-4, C2-3, C3-6, C3-5, C3-4, C4-6, C4-5, and C5-6 alkyl.

As used herein, "alkyl" refers to a radical of a straight-chain or branched saturated hydrocarbon group having from 1 to 50 carbon atoms ("C1-50 alkyl"). In some embodiments, an alkyl group has 1 to 40 carbon atoms ("C1-40 alkyl"). In some embodiments, an alkyl group has 1 to 30 carbon atoms ("C1-30 alkyl"). In some embodiments, an alkyl group has 1 to 20 carbon atoms ("C1-20 alkyl"). In some embodiments, an alkyl group has 1 to 10 carbon atoms ("C1-10 alkyl"). In some embodiments, an alkyl group has 1 to 9 carbon atoms ("C1-9 alkyl"). In some embodiments, an alkyl group has 1 to 8 carbon atoms ("C1-8 alkyl"). In some embodiments, an alkyl group has 1 to 7 carbon atoms ("C1-7 alkyl"). In some embodiments, an alkyl group has 1 to 6 carbon atoms ("C1-6 alkyl"). In some embodiments, an alkyl group has 1 to 5 carbon atoms ("C1-5 alkyl"). In some embodiments, an alkyl group has 1 to 4 carbon atoms ("C1-4 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). In some embodiments, an alkyl group has 2 to 6 carbon atoms ("C2-6 alkyl"). Examples of C1-6 alkyl groups include, without limitation, methyl (C1), ethyl (C2), n-propyl (C3), isopropyl (C3), n-butyl (C4), tert-butyl (C4), sec-butyl (C4), iso-butyl (C4), n-pentyl (C5), 3-pentanyl (C5), amyl (C5), neopentyl (C5), 3-methyl-2-butanyl (C5), tertiary amyl (C5), and n-hexyl (C6). Additional examples of alkyl groups include n-heptyl (C7), n-octyl (C8) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted C1-50 alkyl. In certain embodiments, the alkyl group is a substituted C1-50 alkyl.

As used herein, "heteroalkyl" refers to an alkyl group as defined herein which further includes at least one heteroatom (e.g., 1 to 25, e.g., 1, 2, 3, or 4 heteroatoms) selected from oxygen, sulfur, nitrogen, boron, silicon, and phosphorus within (i.e., inserted between adjacent carbon atoms of) and/or placed at one or more terminal position (s) of the parent chain. In certain embodiments, a heteroalkyl group refers to a saturated group having from 1 to 50 carbon atoms and 1 or more heteroatoms within the parent chain ("heteroC1-50 alkyl"). In certain embodiments, a heteroalkyl group refers to a saturated group having from 1 to 40 carbon atoms and 1 or more heteroatoms within the parent chain ("heteroC1-40 alkyl"). In certain embodiments, a heteroalkyl group refers to a saturated group having from 1 to 30 carbon atoms and 1 or more heteroatoms within the parent chain ("heteroC1-30 alkyl"). In certain embodiments, a heteroalkyl group refers to a saturated group having from 1 to 20 carbon atoms and 1 or more heteroatoms within the parent chain ("heteroC1-20 alkyl"). In certain embodiments, a heteroalkyl group refers to a saturated group having from 1 to 10 carbon atoms and 1 or more heteroatoms within the parent chain ("heteroC1-10 alkyl"). In some embodiments, a heteroalkyl group is a saturated group having 1 to 9 carbon atoms and 1 or more heteroatoms within the parent chain ("heteroC1-9 alkyl"). In some embodiments, a heteroalkyl group is a saturated group having 1 to 8 carbon atoms and 1 or more heteroatoms within the parent chain ("heteroC1-8 alkyl"). In some embodiments, a heteroalkyl group is a saturated group having 1 to 7 carbon atoms and 1 or more heteroatoms within the parent chain ("heteroC1-7 alkyl"). In some embodiments, a heteroalkyl group is a saturated group having 1 to 6 carbon atoms and 1 or more heteroatoms within the parent chain ("heteroC1-6 alkyl"). In some embodiments, a heteroalkyl group is a saturated group having 1 to 5 carbon atoms and 1 or 2 heteroatoms within the parent chain ("heteroC1-5 alkyl"). In some embodiments, a heteroalkyl group is a saturated group having 1 to 4 carbon atoms and 1 or 2 heteroatoms within the parent chain ("heteroC1-4 alkyl"). In some embodiments, a heteroalkyl group is a saturated group having 1 to 3 carbon atoms and 1 heteroatom within the parent chain ("heteroC1-3 alkyl"). In some embodiments, a heteroalkyl group is a saturated group having 1 to 2 carbon atoms and 1 heteroatom within the parent chain ("heteroC1-2 alkyl"). In some embodiments, a heteroalkyl group is a saturated group having 1 carbon atom and 1 heteroatom ("heteroC1 alkyl"). In some embodiments, a heteroalkyl group is a saturated group having 2 to 6 carbon atoms and 1 or 2 heteroatoms within the parent chain ("heteroC2-6 alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC1-50 alkyl. In certain embodiments, the heteroalkyl group is a substituted heteroC1-50 alkyl.

As used herein, "alkenyl" refers to a radical of a straight-chain or branched hydrocarbon group having from 2 to 50 carbon atoms and one or more carbon-carbon double bonds (e.g., 1, 2, 3, or 4 double bonds) ("C2-50 alkenyl"). In some embodiments, an alkenyl group has 2 to 40 carbon atoms ("C2-40 alkenyl"). In some embodiments, an alkenyl group has 2 to 30 carbon atoms ("C2-30 alkenyl"). In some embodiments, an alkenyl group has 2 to 20 carbon atoms ("C2-20 alkenyl"). In some embodiments, an alkenyl group has 2 to 10 carbon atoms ("C2-10 alkenyl"). In some embodiments, an alkenyl group has 2 to 9 carbon atoms ("C2-9 alkenyl"). In some embodiments, an alkenyl group has 2 to 8 carbon atoms ("C2-8 alkenyl"). In some embodiments, an alkenyl group has 2 to 7 carbon atoms ("C2-7 alkenyl"). In some embodiments, an alkenyl group has 2 to 6 carbon atoms ("C2-6 alkenyl"). In some embodiments, an alkenyl group has 2 to 5 carbon atoms ("C2-5 alkenyl"). In some embodiments, an alkenyl group has 2 to 4 carbon atoms ("C2-4 alkenyl"). In some embodiments, an alkenyl group has 2 to 3 carbon atoms ("C2-3 alkenyl"). In some embodiments, an alkenyl group has 2 carbon atoms ("C2 alkenyl"). The one or more carbon-carbon double bonds can be internal (such as in 2-butenyl) or terminal (such as in 1-butenyl). Examples of C2-4 alkenyl groups include, without limitation, ethenyl (C2), 1-propenyl (C3), 2-propenyl (C3), 1-butenyl (C4), 2-butenyl (C4), butadienyl (C4), and the like. Examples of C2-6 alkenyl groups include the aforementioned C2-4 alkenyl groups as well as pentenyl (C5), pentadienyl (C5), hexenyl (C6), and the like. Additional examples of alkenyl include heptenyl (C7), octenyl (C8), octatrienyl (C8), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C2-50 alkenyl. In certain embodiments, the alkenyl group is a substituted C2-50 alkenyl.

As used herein, "heteroalkenyl" refers to an alkenyl group as defined herein which further includes at least one heteroatom (e.g., 1 to 25, e.g., 1, 2, 3, or 4 heteroatoms) selected from oxygen, sulfur, nitrogen, boron, silicon, and phosphorus within (i.e., inserted between adjacent carbon atoms of) and/or placed at one or more terminal position(s) of the parent chain. In certain embodiments, a heteroalkenyl group refers to a group having from 2 to 50 carbon atoms, at least one double bond, and 1 or more heteroatoms within the parent chain ("heteroC2-50 alkenyl"). In certain embodiments, a heteroalkenyl group refers to a group having from 2 to 40 carbon atoms, at least one double bond, and 1 or more heteroatoms within the parent chain ("heteroC2-40 alkenyl"). In certain embodiments, a heteroalkenyl group refers to a group having from 2 to 30 carbon atoms, at least one double bond, and 1 or more heteroatoms within the parent chain ("heteroC2-30 alkenyl"). In certain embodiments, a heteroalkenyl group refers to a group having from 2 to 20 carbon atoms, at least one double bond, and 1 or more heteroatoms within the parent chain ("heteroC2-20 alkenyl"). In certain embodiments, a heteroalkenyl group refers to a group having from 2 to 10 carbon atoms, at least one double bond, and 1 or more heteroatoms within the parent chain ("heteroC2-10 alkenyl"). In some embodiments, a heteroalkenyl group has 2 to 9 carbon atoms at least one double bond, and 1 or more heteroatoms within the parent chain ("heteroC2-9 alkenyl"). In some embodiments, a heteroalkenyl group has 2 to 8 carbon atoms, at least one double bond, and 1 or more heteroatoms within the parent chain ("heteroC2-8 alkenyl"). In some embodiments, a heteroalkenyl group has 2 to 7 carbon atoms, at least one double bond, and 1 or more heteroatoms within the parent chain ("heteroC2-7 alkenyl"). In some embodiments, a heteroalkenyl group has 2 to 6 carbon atoms, at least one double bond, and 1 or more heteroatoms within the parent chain ("heteroC2-6 alkenyl"). In some embodiments, a heteroalkenyl group has 2 to 5 carbon atoms, at least one double bond, and 1 or 2 heteroatoms within the parent chain ("heteroC2-5 alkenyl"). In some embodiments, a heteroalkenyl group has 2 to 4 carbon atoms. at least one double bond, and for 2 heteroatoms within the parent chain ("heteroC2-4 alkenyl"). In some embodiments, a heteroalkenyl group has 2 to 3 carbon atoms, at least one double bond, and 1 heteroatom within the parent chain ("heteroC2-3 alkenyl"). In some embodiments, a heteroalkenyl group has 2 to 6 carbon atoms, at least one double, bond, and 1 or 2 heteroatoms within the parent chain ("heteroC2-6 alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC2-50 alkenyl. In certain embodiments, the heteroalkenyl group is a substituted heteroC2-50 alkenyl.

As used herein, "alkynyl" refers to a radical of a straight-chain or branched hydrocarbon group having from 2 to 50 carbon atoms and one or more carbon-carbon triple bonds (e.g., 1, 2, 3, or 4 triple bonds) and optionally one or more double bonds (e.g., 1, 2, 3, or 4 double bonds) ("C2-50 alkynyl"). An alkynyl group that has one or more triple bonds and one or more double bonds is also referred to as an "ene-yne". In some embodiments, an alkynyl group has 2 to 40 carbon atoms ("C2-40 alkynyl"). In some embodiments, an alkynyl group has 2 to 30 carbon atoms ("C2-30 alkynyl"). In some embodiments, an alkynyl group has 2 to 20 carbon atoms ("C2-20 alkynyl"). In some embodiments, an alkynyl group has 2 to 10 carbon atoms ("C2-10 alkynyl"). In some embodiments, an alkynyl group has 2 to 9 carbon atoms ("C2-9 alkynyl"). In some embodiments, an alkynyl group has 2 to 8 carbon atoms ("C2-8 alkynyl"). In some embodiments, an alkynyl group has 2 to 7 carbon atoms ("C2-7 alkynyl"). In some embodiments, an alkynyl group has 2 to 6 carbon atoms ("C2-6 alkynyl"). In some embodiments, an alkynyl group has 2 to 5 carbon atoms ("C2-5 alkynyl"). In some embodiments, an alkynyl group has 2 to 4 carbon atoms ("C2-4 alkynyl"). In some embodiments, an alkynyl group has 2 to 3 carbon atoms ("C2-3 alkynyl"). In some embodiments, an alkynyl group has 2 carbon atoms ("C2 alkynyl"). The one or more carbon-carbon triple bonds can be internal (such as in 2-butynyl) or terminal (such as in 1-butynyl). Examples of $C_{2-4}$ alkynyl groups include, without limitation, ethynyl (C2), 1-propynyl (C3), 2-propynyl (C3), 1-butynyl (C4), 2-butynyl (C4), and the like. Examples of C2-6 alkenyl groups include the aforementioned C2-4 alkynyl groups as well as pentynyl (C5), hexynyl (C6), and the like. Additional examples of alkynyl include heptynyl (C7), octynyl (C8), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C2-50 alkynyl. In certain embodiments, the alkynyl group is a substituted C2-50 alkynyl.

As used herein, "heteroalkynyl" refers to an alkynyl group as defined herein which further includes at least one heteroatom (e.g., 1 to 25, e.g., 1, 2, 3, or 4 heteroatoms) selected from oxygen, sulfur, nitrogen, boron, silicon, and phosphorus within (i.e., inserted between adjacent carbon atoms of) and/or placed at one or more terminal position(s) of the parent chain. In certain embodiments, a heteroalkynyl group refers to a group having from 2 to 50 carbon atoms, at least one triple bond, and 1 or more heteroatoms within the parent chain ("heteroC2-50 alkynyl"). In certain embodiments, a heteroalkynyl group refers to a group having from 2 to 40 carbon atoms, at least one triple bond, and 1 or more heteroatoms within the parent chain ("heteroC2-40 alkynyl"). In certain embodiments, a heteroalkynyl group refers to a group having from 2 to 30 carbon atoms, at least one triple bond, and 1 or more heteroatoms within the parent chain ("heteroC2-30 alkynyl"). In certain embodiments, a heteroalkynyl group refers to a group having from 2 to 20 carbon atoms, at least one triple bond, and 1 or more heteroatoms within the parent chain ("heteroC2-20 alkynyl"). In certain embodiments, a heteroalkynyl group refers to a group having from 2 to 10 carbon atoms, at least one triple bond, and 1 or more heteroatoms within the parent chain ("heteroC2-10 alkynyl"). In some embodiments, a heteroalkynyl group has 2 to 9 carbon atoms, at least one triple bond, and 1 or more heteroatoms within the parent chain ("heteroC2-9 alkynyl"). In some embodiments, a heteroalkynyl group has 2 to 8 carbon atoms, at least one triple bond, and 1 or more heteroatoms within the parent chain ("heteroC2-8 alkynyl"). In some embodiments, a heteroalkynyl group has 2 to 7 carbon atoms, at least one triple bond, and 1 or more heteroatoms within the parent chain ("heteroC2-7 alkynyl"). In some embodiments, a heteroalkynyl group has 2 to 6 carbon atoms, at least one triple bond, and 1 or more heteroatoms within the parent chain ("heteroC2-6 alkynyl"). In some embodiments, a heteroalkynyl group has 2 to 5 carbon atoms, at least one triple bond, and 1 or 2 heteroatoms within the parent chain ("heteroC2-5 alkynyl"). In some embodiments, a heteroalkynyl group has 2 to 4 carbon atoms, at least one triple bond, and for 2 heteroatoms within the parent chain ("heteroC2-4 alkynyl"). In some embodiments, a heteroalkynyl group has 2 to 3 carbon atoms, at least one triple bond, and 1 heteroatom within the parent chain ("heteroC2-3 alkynyl"). In some embodiments, a heteroalkynyl group has 2 to 6 carbon atoms, at least one triple bond. and 1 or 2 heteroatoms within the parent chain ("heteroC2-6 alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC2-50 alkynyl. In certain embodiments, the heteroalkynyl group is a substituted heteroC2-50 alkynyl.

As used herein, "carbocyclyl" or "carbocyclic" refers to a radical of a non-aromatic cyclic hydrocarbon group having from 3 to 10 ring carbon atoms ("C3-10 carbocyclyl") and zero heteroatoms in the non-aromatic ring system. In some embodiments, a carbocyclyl group has 3 to 8 ring carbon atoms ("C3-8 carbocyclyl"). In some embodiments, a carbocyclyl group has 3 to 7 ring carbon atoms ("C3-7 carbocyclyl"). In some embodiments, a carbocyclyl group has 3 to 6 ring carbon atoms ("C3-6 carbocyclyl"). In some embodiments, a carbocyclyl group has 4 to 6 ring carbon atoms ("C4-6 carbocyclyl"). In some embodiments, a carbocyclyl group has 5 to 6 ring carbon atoms ("C5-6 carbocyclyl"). In some embodiments, a carbocyclyl group has 5 to 10 ring carbon atoms ("C5-10 carbocyclyl"). Exemplary $C_{3-6}$ carbocyclyl groups include, without limitation, cyclopropyl (C3), cyclopropenyl (C3), cyclobutyl (C4), cyclobutenyl (C4), cyclopentyl (C5), cyclopentenyl (C5), cyclohexyl (C6), cyclohexenyl (C6), cyclohexadienyl (C6), and the like. Exemplary C3-8 carbocyclyl groups include, without limitation, the aforementioned C3-6 carbocyclyl groups as well as cycloheptyl (C7), cycloheptenyl (C7), cycloheptadienyl (C7), cycloheptatrienyl (C7), cyclooctyl (C8), cyclooctenyl (C8), bicyclo[2.2.1]heptanyl (C7), bicyclo[2.2.2]octanyl (C8), and the like. Exemplary C3-10 carbocyclyl groups include, without limitation, the aforementioned C3-8 carbocyclyl groups as well as cyclononyl (C9), cyclononenyl (C9), cyclodecyl (C10), cyclodecenyl (C10), octahydro-1H-indenyl (C9), decahydronaphthalenyl (C10), spiro[4.5]decanyl (C10), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" or "carbocyclic" is referred to as a "cycloalkyl", i.e., a monocyclic, saturated carbocyclyl group having from 3 to 10 ring carbon atoms ("C3-10 cycloalkyl"). In some embodiments, a cycloalkyl group has 3 to 8 ring carbon atoms ("C3-8 cycloalkyl"). In some embodiments, a cycloalkyl group has 3 to 6 ring carbon atoms ("C3-6, cycloalkyl"). In some embodiments, a cycloalkyl group has 4 to 6 ring carbon atoms ("C4-6 cycloalkyl"). In some embodiments, a cycloalkyl group has 5 to 6 ring carbon atoms ("C5-6 cycloalkyl"). In some embodiments, a cycloalkyl group has 5 to 10 ring carbon atoms ("C5-10 cycloalkyl"). Examples of C5-6 cycloalkyl groups include cyclopentyl (C5) and cyclohexyl (C5). Examples of C3-6 cycloalkyl groups include the aforementioned C5-6 cycloalkyl groups as well as cyclopropyl (C3) and cyclobutyl (C4). Examples of C3-8 cycloalkyl groups include the aforementioned C3-6 cycloalkyl groups as well as cycloheptyl (C7) and cyclooctyl (C8). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C3-10 cycloalkyl. In certain embodiments, the cycloalkyl group is a substituted C3-10 cycloalkyl.

As used herein, "heterocyclyl" or "heterocyclic" refers to a radical of a 3- to 14-membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")). and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-10 membered heterocyclyl"). In some embodiments, a heterocyclyl group is a 5-8 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-8 membered heterocyclyl"). In some embodiments, a heterocyclyl group is a 5-6 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-6 membered heterocyclyl"). In some embodiments, the 5-6 membered heterocyclyl has 1 or more (e.g., 1, 2, or 3) ring heteroatoms selected from oxygen, sulfur, nitrogen, boron, silicon, and phosphorus. In some embodiments, the 5-6 membered heterocyclyl has 1 or 2 ring heteroatoms selected from oxygen, sulfur, nitrogen, boron, silicon, and phosphorus. In some embodiments, the 5-6 membered heterocyclyl has 1 ring heteroatom selected from oxygen, sulfur, nitrogen, boron, silicon, and phosphorus.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation. tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C6-14 aryl"). In some embodiments, an aryl group has 6 ring carbon atoms ("C6 aryl"; e.g., phenyl). In some embodiments, an aryl group has 10 ring carbon atoms ("C10 aryl"; e.g., naphthyl such as 1-naphthyl and 2-naphthyl). In some embodiments, an aryl group has 14 ring carbon atoms ("C14 aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted C6-14 aryl. In certain embodiments, the aryl group is a substituted C6-14 aryl.

As used herein, "heteroaryl" refers to a radical of a 5-14 membered monocyclic or polycyclic (e.g., bicyclic or tricyclic) 4n+2 aromatic ring system (e.g., having 6, 10, or 14 π electrons shared in a cyclic array) having ring carbon atoms and 1 or more (e.g., 1, 2, 3, or 4 ring heteroatoms) ring heteroatoms provided in the aromatic ring system, wherein each heteroatom is independently selected from oxygen, sulfur, nitrogen, boron, silicon, and phosphorus ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-10 membered heteroaryl"). In some embodiments, a heteroaryl group is a 5-8 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-8 membered heteroaryl"). In some embodiments, a heteroaryl group is a 5-6 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-6 membered heteroaryl"). In some embodiments, the 5-6 membered heteroaryl has 1 or more (e.g., 1, 2, or 3) ring heteroatoms selected from oxygen, sulfur, nitrogen, boron, silicon, and phosphorus. In some embodiments, the 5-6 membered heteroaryl has 1 or 2 ring heteroatoms selected from oxygen, sulfur, nitrogen, boron, silicon, and phosphorus. In some embodiments, the 5-6 membered heteroaryl has 1 ring heteroatom selected from oxygen, sulfur, nitrogen, boron, silicon, and phosphorus. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation. pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or. 'unsubstituted" heteroalkynyl. "substituted" or "unsubstituted" carbocyclyl. "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO2, —N3, —SO2H, —SO3H, —OH, —ORaa, —ON(Rbb)2, —N(Rbb)2, —N(Rbb)3+X−, —N(ORcc)Rbb, —SeH, —SeRaa, —SH, —SRaa, —SSRcc, —C(=O)Raa, —CO2H, —CHO, —C(ORcc)2, —CO2Raa, —OC(=O)Raa, —OCO2Raa, —C(=O)N(Rbb)2, —OC(=O)N(Rbb)2, —NRbbC(=O)Raa, —NRbbCO2Raa, —NRbbC(=O)N(Rbb)2, —C(=NRbb)Raa, —C(=NRbb)ORaa, —OC(=NRbb)Raa, —OC(=NRbb)ORaa, —C(=NRbb)N(Rbb)2, —OC(=NRbb)N(Rbb)2, —NRbbC(=NRbb)N(Rbb)2, —C(=O)NRbbSO2Raa, —NRbbSO2Raa, —SO2N(Rbb)2, —SO2Raa, —SO2ORaa, —OSO2Raa, —S(=O)Raa, —OS(=O)Raa, —Si(Raa)3-OSi(Raa)3-C(=S)N(Rbb)2, —C(=O)SRaa, —C(=S)SRaa, —SC(=S)SRaa, —SC(=O)SRaa, —OC(=O)SRaa, —SC(=O)ORaa, —SC(=O)Raa, —P(=O)2Raa, —OP(=O)2Raa, —P(=O)(Raa)2, —OP(=O)(Raa)2, —OP(=O)(ORcc)2, —P(=O)2N(Rbb)2, —OP(=O)2N(Rbb)2, —P(=O)(NRbb)2, —OP(=O)(NRbb)2, —NRbbP(=O)(ORcc)2, —NRbbP(=O)(NRbb)2, —P(Rcc)2, —P(Rcc)3, —OP(Rcc)2, —OP(Rcc)3, —B(Raa)2, —B(ORcc)2, —BRaa(ORcc), C1-50 alkyl, C2-50 alkenyl, C2-50 alkynyl, C3-14 carbocyclyl, 3-14 membered heterocyclyl, C6-14 aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 Rdd groups;

or two geminal hydrogens on a carbon atom are replaced with the group =O, =S, =NN(Rbb)2, =NNRbbC(=O)Raa, =NNRbbC(=O)ORaa, =NNRbbS(=O)2Raa, =NRbb, or =NORcc;

each instance of Raa is, independently, selected from C1-50 alkyl, C2-50 alkenyl, C2-50 alkynyl, C3-10 carbocyclyl, 3-14 membered heterocyclyl, C6-14 aryl, and 5-14 membered heteroaryl, or two Raa groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rbb is, independently, selected from hydrogen, —OH, —ORaa, —N(Rcc)2, —CN, —C(=O)Raa, —C(=O)N(Rcc)2, —CO2Raa, —SO2Raa, —C(=NRcc)ORaa, —C(=NRcc)N(Rcc)2, —SO2N(Rcc)2, —SO2Rcc, —SO2ORcc, —SORaa, —C(=S)N(Rcc)2, —C(=O)SRcc, —C(=S)SRcc, —P(=O)2Raa, —P(=O)(Raa)2, —P(=O)2N(Rcc)2, —P(=O)(NRcc)2, C1-50 alkyl, C2-50 alkenyl, C2-50 alkynyl, C3-10 carbocyclyl, 3-14 membered heterocyclyl, C6-14 aryl, and 5-14 membered heteroaryl, or two Rbb groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rcc is, independently, selected from hydrogen, C1-50 alkyl, C2-50 alkenyl, C2-50 alkynyl, C3-10 carbocyclyl, 3-14 membered heterocyclyl, C6-14 aryl, and 5-14 membered heteroaryl, or two Rcc groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rdd is, independently, selected from halogen, —CN, —NO2, —N3, —SO2H, —SO3H, —OH, —ORee, —ON(Rff)2, —N(Rff)2, —N(Rff)3+X−, —N(ORee)Rff, —SH, —SRee, —SSRee, —C(=O)Ree, —CO2H, —CO2Ree, —OC(=O)Ree, —OCO2Ree, —C(=O)N(Rff)2, —OC(=O)N(Rff)2, —NRffC(=O)Ree, —NRffCO2Ree, —NRffC(=O)N(Rff)2, —C(=NRff)ORee, —OC(=NRff)Ree, —OC(=NRff)ORee, —C(=NRff)N(Rff)2, —OC(=NRff)N(Rff)2, —NRffC(=NRff)N(Rff)2, —NRffSO2Ree, —SO2N(Rff)2, —SO2Ree, —SO2ORee, —OSO2Ree, —S(=O)Ree, —Si(Ree)3, —OSi(Ree)3, —C(=S)N(Rff)2, —C(=O)SRee, —C(=S)SRee, —SC(=S)SRee, —P(=O)2Ree, —P(=O)(Ree)2, —OP(=O)(Ree)2, —OP(=O)(ORee)2, C1-50 alkyl, C2-50 alkenyl, C2-50 alkynyl, C3-10 carbocyclyl, 3-10 membered heterocyclyl, C6-10 aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 Rgg groups, or two geminal Rdd substituents can be joined to form =O or =S;

each instance of Ree is, independently, selected from C1-50 alkyl, C2-50 alkenyl, C2-50 alkynyl, C3-10 carbocyclyl, C6-10 aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 Rgg groups;

each instance of Rff is, independently, selected from hydrogen, C1-50 alkyl, C2-50 alkenyl, C2-50 alkynyl, C3-10 carbocyclyl, 3-10 membered heterocyclyl, C6-10 aryl and 5-10 membered heteroaryl, or two Rff groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rgg groups; and each instance of Rgg is, independently, halogen, —CN, —NO2, —N3, —SO2H, —SO3H, —OH, —OC1-50 alkyl, —ON(C1-50 alkyl)2, —N(C1-50 alkyl)2, —N(C1-50 alkyl)3+X−, —NH(C1-50 alkyl)2+X−, —NH2(C1-50 alkyl)+X−, —NH3+X−, —N(OC1-50 alkyl)(C1-50 alkyl), —N(OH)(C1-50 alkyl), —NH(OH), —SH, —SC1-50 alkyl, —SS(C1-50 alkyl), —C(=O)(C1-50 alkyl), —CO2H, —CO2(C1-50 alkyl), —OC(=O)(C1-50 alkyl), —OCO2(C1-50 alkyl), —C(=O)NH2, —C(=O)N(C1-50 alkyl)2, —OC(=O)NH(C1-50 alkyl), —NHC(=O)(C1-50 alkyl), —N(C1-50 alkyl)C(=O)(C1-50 alkyl), —NHCO2(C1-50 alkyl), —NHC(=O)N(C1-50 alkyl)2, —NHC(=O)NH(C1-50 alkyl), —NHC(=O)NH2, —C(=NH)O(C1-50 alkyl), —OC(=NH)(C1-50 alkyl), —OC(=NH)OC1-50 alkyl, —C(=NH)N(C1-50 alkyl)2, —C(=NH)NH(C1-50 alkyl), —C(=NH)NH2, —OC(=NH)N(C1-50alkyl)2, —OC(NH)NH(C1-50 alkyl), —OC(NH)NH2, —NHC(NH)N(C1-50 alkyl)2, —NHC(=NH)NH2, —NHSO2 (C1-50 alkyl), —SO2N(C1-50 alkyl)2, —SO2NH(C1-50 alkyl), —SO2NH2, —SO2C1-50 alkyl, —SO2OC1-50 alkyl, —OSO2C1-6 alkyl, —SOC1-6 alkyl, —Si(C1-50 alkyl)3, —OSi(C1-6 alkyl)3-C(=S)N(C1-50 alkyl)2, C(=S)NH(C1-50 alkyl), C(=S)NH2, —C(=O)S(C1-6 alkyl), —C(=S)SC1-6 alkyl, —SC(=S)SC1-6 alkyl, —P(=O)2(C1-50 alkyl), —P(=O)(C1-50 alkyl)2, —OP(=O)(C1-50 alkyl)2, —OP(=O)(OC1-50 alkyl)2, C1-50 alkyl, C2-50 alkenyl, C2-50 alkynyl, C3-10 carbocyclyl, C6-10 aryl, 3-10 membered heterocyclyl, 5-10 membered heteroaryl; or two geminal Rgg substituents can be joined to form =O or =S; wherein X− is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quaternary amine in order to maintain electronic neutrality. Exemplary counterions include halide ions (e.g., F—, Cl—, Br—, I—), NO3-, ClO4-, OH—, H2PO4-, HSO4-, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —ORaa, —N(Rcc)2, —CN, —C(=O)Raa, —C(=O)N(Rcc)2, —CO2Raa, —SO2Raa, —C(=NRbb) Raa, —C(=NRcc)ORaa, —C(=NRcc)N(Rcc)2, —SO2N (Rcc)2, —SO2Rcc, —SO2ORcc, —SORaa, —C(=S)N (Rcc)2, —C(=O)SRcc, —C(=S)SRcc, —P(=O)2Raa, —P(=O)(Raa)2, —P(=O)2N(Rcc)2, —P(=O)(NRcc)2, C1-50 alkyl, C2-50 alkenyl, C2-50 alkynyl, C3-10 carbocyclyl, 3-14 membered heterocyclyl, C6-14 aryl, and 5-14 membered heteroaryl, or two Rcc groups, together with the N atom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups, and wherein Raa, Rbb, Rcc and Rdd are as defined above.

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —ORaa, —N(Rcc)2, —CN, —C(=O)Raa, —C(=O)N(Rcc)2, —CO2Raa, —SO2Raa, —C(=NRbb) Raa, —C(=NRcc)ORaa, —C(=NRcc)N(Rcc)2, —SO2N (Rcc)2, —SO2Rcc, —SO2ORcc, —SORaa, —C(=S)N (Rcc)2, —C(=O)SRcc, —C(=S)SRcc, —P(=O)2Raa, —P(=O)(Raa)2, —P(=O)2N(Rcc)2, —P(=O)(NRcc)2, C1-10 alkyl, C1-10 perhaloalkyl, C2-10 alkenyl, C2-10 alkynyl, C3-10 carbocyclyl, 3-14 membered heterocyclyl, C6-14 aryl, and 5-14 membered heteroaryl, or two Rcc groups, together with the nitrogen atom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups, and wherein Raa, Rbb, Rcc and Rdd are as defined above.

In certain embodiments, the substituent present on a nitrogen atom is a nitrogen protecting group (also referred to as an amino protecting group). Nitrogen protecting groups include, but are not limited to, —OH, —ORaa, —N(Rcc)2, —C(=O)Raa, —C(=O)N(Rcc)2, —CO2Raa, —SO2Raa, —C(=NRcc)Raa, —C(=NRcc)ORaa, —C(=NRcc)N (Rcc)2, —SO2N(Rcc)2, —SO2Rcc, —SO2ORcc, —SORaa, —C(=S)N(Rcc)2, —C(=O)SRcc, —C(=S) SRcc, C1-10 alkyl (e.g., aralkyl, heteroaralkyl), C2-10 alkenyl, C2-10 alkynyl, C3-10 carbocyclyl, 3-14 membered heterocyclyl, C6-14 aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4 or 5 Rdd groups, and wherein Raa, Rbb, Rcc and Rdd are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(=O)Raa) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)ORaa) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)] methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl) methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(═O)2Raa) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —Raa, —N(Rbb)2, —C(═O)SRaa, —C(═O)Raa, —CO2Raa, —C(═O)N(Rbb)2, —C(═NRbb)Raa, —C(═NRbb)ORaa, —C(═NRbb)N(Rbb)2, —S(═O)Raa, —SO2Raa, Si(Raa)3, —P(Rcc)2, —P(Rcc)3, —P(═O)2Raa, —P(═O)(Raa)2, —P(═O)(ORcc)2, —P(═O)2N(Rbb)2, and —P(═O)(NRbb)2, wherein Raa, Rbb, and Rcc are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —Raa, —N(Rbb)2, —C(=O)SRaa, —C(=O)Raa, —CO2Raa, C(=O)N(Rbb)2, —C(=NRbb) Raa, —C(=NRbb)ORaa, —C(=NRbb)N(Rbb)2, —S(=O)Raa, —SO2Raa, —Si(Raa)3, —P(Rcc)2, —P(Rcc)3, —P(=O)2Raa, —P(=O)(Raa)2, —P(=O)(ORcc)2, —P(=O)2N(Rbb)2, and —P(=O)(NRbb)2, wherein Raa, Rbb, and Rcc are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

As used herein, a "leaving group" is an art-understood term referring to a molecular fragment that departs with a pair of electrons in heterolytic bond cleavage, wherein the molecular fragment is an anion or neutral molecule. See, for example, Smith, March's Advanced Organic Chemistry 6th ed. (501-502). Exemplary leaving groups include, but are not limited to, halo (e.g., chloro, bromo, iodo) and sulfonyl substituted hydroxyl groups (e.g., tosyl, mesyl, besyl).

Additional Definitions

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Expression: As used herein, "expression" of a nucleic acid sequence refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalent, are used inter-changeably.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA such as mRNA, siRNA, microRNA, as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polymer: As used herein, a "polymer" refers to a compound comprised of at least 3 (e.g., at least 10, 20, 30, 40, 50, 60, 70, 80, 90, 100, etc.) repeating covalently bound structural units.

Salt: As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate. digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, non-toxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

DETAILED DESCRIPTION

The present invention provides, among other things, a novel class of biodegradable lipid compounds for improved in vivo delivery of therapeutic agents, such as nucleic acids. In particular, a biodegradable compound described herein may be used to as a cationic lipid, together with other non-cationic lipids, to formulate a lipid based nanoparticle (e.g., liposome) for encapsulating therapeutic agents, such as nucleic acids (e.g., DNA, siRNA, mRNA, microRNA) for therapeutic use.

Biodegradable Compounds

In some embodiments, a biodegradable compound according to the invention has a structure of formula I:

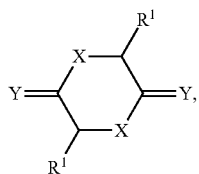

or a pharmaceutically acceptable salt thereof,
wherein:

each instance of X is independently O or S;

each instance of Y is independently O or S;

each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, —$OR^{A1}$, —$N(R^{A1})_2$, —$SR^{A1}$, or a group of formula (iv):

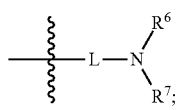

L is an optionally substituted; alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof, and each of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii);

Formulae (i), (ii), and (iii) are:

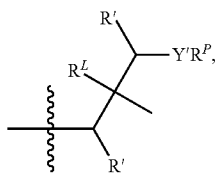

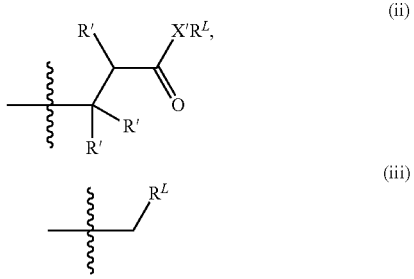

each instance of R' is independently hydrogen or optionally substituted alkyl;

X' is O or S, or $NR^X$;

$R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

Y' is O, S, or $NR^Y$;

$R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom;

$R^L$ is optionally substituted $C_{1-50}$ alkyl, optionally substituted $C_{2-50}$ alkenyl, optionally substituted $C_{2-50}$ alkynyl, optionally substituted hetero$C_{1-50}$ alkyl, optionally substituted hetero$C_{2-50}$ alkenyl, optionally substituted hetero$C_{2-50}$ alkynyl, or a polymer;

and each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{A1}$ groups, together with the nitrogen atom to which they are attached, are joined to form an optionally substituted heterocyclic or optionally substituted heteroaryl ring.

In certain embodiments, a group of formula (i) represents a group of formula (i-a) or a group of formula (i-b):

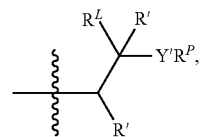

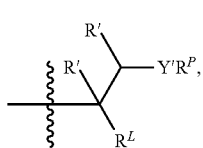

(i-b)

wherein each variable is independently as defined above and described herein. In some embodiments, a group of formula (i) is a group of formula (i-a). In some embodiments, a group of formula (i) is a group of formula (i-b).

In some embodiments, at least one instance of $R^1$ is a group of formula (iv). In some embodiments, at least one instance of $R^1$ is a group of formula (iv), wherein at least one of $R^6$ and $R^7$ is a group of formula (i), (ii) or (iii). In some embodiments, at least one instance of $R^1$ is a group of formula (iv), wherein each of $R^6$ and $R^7$ is independently a group of formula (i), (ii) or (iii).

In some embodiments, each $R^1$ is independently a group of formula (iv). In some embodiments, each $R^1$ is independently a group of formula (iv), wherein at least one of $R^6$ and $R^7$ is a group of formula (i), (ii) or (iii). In some embodiments, each $R^1$ is independently a group of formula (iv), wherein each of $R^6$ and $R^7$ is independently a group of formula (i), (ii) or (iii). In some embodiments, each $R^1$ is independently a group of formula (iv), wherein each of $R^6$ and $R^7$ is independently a group of formula (i). In some embodiments, each $R^1$ is independently a group of formula (iv), wherein each of $R^6$ and $R^7$ is independently a group of formula (ii). In some embodiments, each $R^1$ is independently a group of formula (iv), wherein each of $R^6$ and $R^7$ is independently a group of formula (iii). In some embodiments, each $R^1$ is independently a group of formula (iv), wherein each of $R^6$ and $R^7$ is independently a group of formula (i-a). In some embodiments, each $R^1$ is independently a group of formula (iv), wherein each of $R^6$ and $R^7$ is independently a group of formula (i-b).

In some embodiments, each instance of R' is hydrogen.

In some embodiments, L is an optionally substituted alkylene.

In some embodiments, a group of formula (iv) is of formula

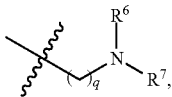

wherein q is an integer between 1 and 50, inclusive, and each of $R^6$ and $R^7$ is independently as defined above and described herein.

In certain embodiments, at least one instance of Q is O. In certain embodiments, each instance of Q is O. In certain embodiments, at least one instance of Q is S. In certain embodiments, each instance of Q is S.

In some embodiments, $R^Q$ is hydrogen. In some embodiments, $R^Q$ is optionally substituted alkyl. In some embodiments, $R^Q$ is optionally substituted alkenyl. In some embodiments, $R^Q$ is optionally substituted alkynyl. In some embodiments, $R^Q$ is carbocyclyl. In some embodiments, $R^Q$ is optionally substituted heterocyclyl. In some embodiments, $R^Q$ is optionally substituted aryl. In some embodiments, $R^Q$ is optionally substituted heteroaryl. In some embodiments, $R^Q$ is a nitrogen protecting group. In some embodiments, $R^Q$ is a group of formula (i), (ii) or (iii). In some embodiments, $R^Q$ is a group of formula (i). In some embodiments, $R^Q$ is a group of formula (ii). In some embodiments, $R^Q$ is a group of formula (iii).

As generally defined above, each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, —$OR^{41}$, —$N(R^{41})_2$, or —$SR^{41}$, or a group of formula (iv), wherein each of $R^{41}$ and formula (iv) is independently as defined above and described herein.

In some embodiments, one $R^1$ is not hydrogen. In some embodiments, both of $R^1$ are not hydrogen.

In certain embodiments, $R^1$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^1$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $R^1$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl. In certain embodiments, at least one instance of $R^1$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl.

In certain embodiments, $R^1$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl. In certain embodiments, at least one instance of $R^1$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl.

In certain embodiments, $R^1$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl. In certain embodiments, at least one instance of $R^1$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl.

In certain embodiments, $R^1$ is optionally substituted carbocyclyl, e.g., optionally substituted $C_{3-10}$ carbocyclyl, optionally substituted $C_{5-8}$ carbocyclyl, optionally substituted $C_{5-6}$ carbocyclyl, optionally substituted $C_5$ carbocyclyl, or optionally substituted $C_6$ carbocyclyl. In certain embodiments, at least one instance of $R^1$ is optionally substituted carbocyclyl, e.g., optionally substituted $C_{3-10}$ carbocyclyl, optionally substituted $C_{5-8}$ carbocyclyl, optionally substituted $C_{5-6}$ carbocyclyl, optionally substituted $C_5$ carbocyclyl, or optionally substituted $C_6$ carbocyclyl.

In some embodiments, $R^1$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5-membered heterocyclyl, or optionally substituted 6-membered heterocyclyl. In certain embodiments, at least one instance of $R^1$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5-membered heterocyclyl, or optionally substituted 6-membered heterocyclyl.

In some embodiments, $R^1$ is optionally substituted aryl. In some embodiments, $R^1$ is optionally substituted phenyl. In some embodiments, $R^1$ is phenyl. In some embodiments, $R^1$ is substituted phenyl. In certain embodiments, at least one instance of $R^1$ is optionally substituted aryl, e.g., optionally substituted phenyl.

In some embodiments, $R^1$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl. In certain embodiments, at least one instance of $R^1$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl.

In some embodiments, $R^1$ is halogen. In some embodiments, $R^1$ is —F. In some embodiments, $R^1$ is —Cl. In some embodiments, $R^1$ is —Br. In some embodiments, $R^1$ is —I.

In some embodiments, $R^1$ is —$OR^{A1}$, wherein R is as defined above and described herein. In some embodiments, $R^1$ is —$N(R^{A1})_2$, wherein each $R^{A1}$ is independently as defined above and described herein. In some embodiments, $R^1$ is —$SR^{A1}$, wherein R is as defined above and described herein.

In some embodiments, an $R^1$ alkyl, alkenyl, alkynyl, carbocyclyl, heterocyclyl, aryl, or heteroaryl group may be substituted. In some embodiments, an $R^1$ alkyl, alkenyl, alkynyl, carbocyclyl, heterocyclyl, aryl, or heteroaryl group may be substituted with an optionally substituted amino group. In some embodiments, an $R^1$ alkyl, alkenyl, alkynyl, carbocyclyl, heterocyclyl, aryl, or heteroaryl group may be substituted with an optionally substituted hydroxyl group. In some embodiments, an $R^1$ alkyl, alkenyl, alkynyl, carbocyclyl, heterocyclyl, aryl, or heteroaryl group may be substituted with an optionally substituted thiol group. In any of the above embodiments, an $R^1$ alkyl, alkenyl, alkynyl, carbocyclyl, heterocyclyl, aryl, or heteroaryl group may be substituted, for example, with an optionally substituted amino group (e.g., —$NR^6R^7$), an optionally substituted hydroxyl group (e.g., —$OR^6$), an optionally substituted thiol group (e.g., —$SR^6$), or with a group of formula (i), (ii), or (iii), wherein each instance of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or a group of formula (i), (ii), or (iii).

In some embodiments, $R^1$ is an optionally substituted natural amino acid side chain. In some embodiments, $R^1$ is a natural amino acid side chain. In some embodiments, $R^1$ is an optionally substituted unnatural amino acid side chain. In some embodiments, $R^1$ is an unnatural amino acid side chain.

In certain embodiments, each instance of $R^1$ is the same. In certain embodiments, at least one $R^1$ group is different. In certain embodiments, each $R^1$ group is different.

In certain embodiments, $R^1$ is an alkyl, alkenyl, alkynyl, carbocyclyl, heterocyclyl, aryl, or heteroaryl group substituted with an amino group of the formula —$NR^6R^7$.

In certain embodiments, $R^1$ is a group of formula (iv):

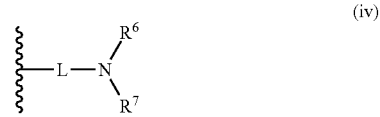

wherein:
L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof; and
each of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii):

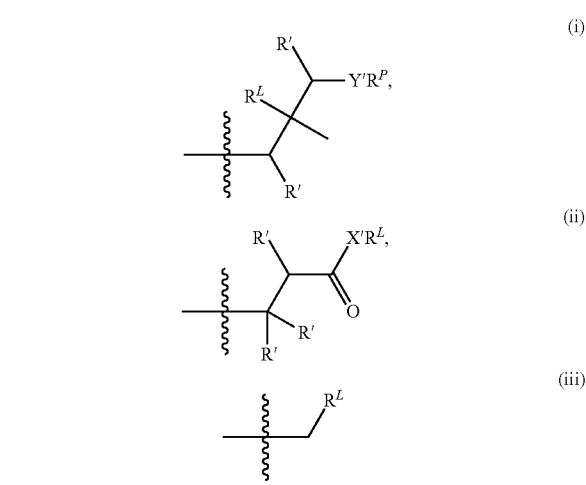

wherein each of R', Y', $R^P$, $R^L$ and X' is independently as defined above and described herein.

In some embodiments, at least one instance of $R^1$ is an alkyl, alkenyl, alkynyl, carbocyclyl, heterocyclyl, aryl, or heteroaryl group substituted with an amino group of the formula —$NR^6R^7$. In some embodiments, at least one instance of $R^1$ is a group of formula (iv). In some embodiments, at least one instance of $R^1$ is a group of formula (iv), wherein at least one instance of $R^6$ and $R^7$ is a group of the formula (i), (ii) or (iii). In some embodiments, at least one instance of $R^1$ is a group of formula (iv), wherein each instance of $R^6$ and $R^7$ is a group of the formula (i), (ii) or (iii). In some embodiments, at least one instance of $R^1$ is a group of formula (iv), wherein each instance of $R^6$ and $R^7$ is a group of the formula (i). In some embodiments, at least one instance of $R^1$ is a group of formula (iv), wherein each instance of $R^6$ and $R^7$ is a group of the formula (ii). In some embodiments, at least one instance of $R^1$ is a group of formula (iv), wherein each instance of $R^6$ and $R^7$ is a group of the formula (iii).

In some embodiments, each instance of $R^1$ is a group of formula (iv). In some embodiments, each instance of $R^1$ is a group of formula (iv), wherein each instance of $R^6$ and $R^7$ is a group of the formula (i), (ii) or (iii). In some embodiments, each instance of $R^1$ is a group of formula (iv), wherein each instance of $R^6$ and $R^7$ is a group of the formula (i), (ii) or (iii). In some embodiments, each instance of $R^1$ is a group of formula (iv), wherein each instance of $R^6$ and $R^7$ is a group of the formula (i). In some embodiments, each instance of $R^1$ is a group of formula (iv), wherein each instance of $R^6$ and $R^7$ is a group of the formula (ii). In some embodiments, each instance of $R^1$ is a group of formula (iv), wherein each instance of $R^6$ and $R^7$ is a group of the formula (iii).

In certain embodiments, at least two instances of $R^1$ is a group of formula (iv). In certain embodiments, at least three instances of $R^1$ is a group of formula (iv). In certain embodiments, at least four instances of $R^1$ is a group of formula (iv). In certain embodiments, at least five instances of $R^1$ is a group of formula (iv). In certain embodiments, at least six instances of $R^1$ is a group of formula (iv). In certain embodiments, at least seven instances of $R^1$ is a group of formula (iv). In certain embodiments, at least eight instances of $R^1$ is a group of formula (iv). In certain embodiments, at least nine instances of $R^1$ is a group of formula (iv). In certain embodiments, each instance of $R^1$ is a group of formula (iv).

In certain embodiments, L is an optionally substituted alkylene; e.g., optionally substituted $C_{1-50}$alkylene, optionally substituted $C_{1-40}$alkylene, optionally substituted $C_{1-30}$alkylene, optionally substituted $C_{1-20}$alkylene, optionally substituted $C_{4-20}$alkylene, optionally substituted $C_{6-20}$alkylene, optionally substituted $C_{8-20}$alkylene, optionally substituted $C_{10-20}$alkylene, optionally substituted $C_{1-6}$alkylene, optionally substituted $C_{2-6}$alkylene, optionally substituted $C_{3-6}$alkylene, optionally substituted $C_{4-6}$alkylene, optionally substituted $C_{4-5}$alkylene, or optionally substituted $C_{3-4}$alkylene. In some embodiments, L is optionally substituted $C_1$ alkylene. In some embodiments, L is optionally substituted $C_2$ alkylene. In some embodiments, L is optionally substituted $C_3$ alkylene. In some embodiments, L is optionally substituted $C_4$ alkylene. In some embodiments, L is optionally substituted $C_5$ alkylene. In some embodiments, L is optionally substituted $C_6$ alkylene. In some embodiments, L is optionally substituted $C_7$ alkylene. In some embodiments, L is optionally substituted $C_8$ alkylene. In some embodiments, L is optionally substituted $C_9$ alkylene. In some embodiments, L is optionally substituted $C_{10}$ alkylene. In some embodiments, L is —$CH_2$—. In some embodiments, L is —$(CH_2)_2$—. In some embodiments, L is —$(CH_2)_3$—. In some embodiments, L is —$(CH_2)_4$—. In some embodiments, L is —$(CH_2)_5$—. In some embodiments, L is —$(CH_2)_6$—. In some embodiments, L is —$(CH_2)_7$—. In some embodiments, L is —$(CH_2)_8$—. In some embodiments, L is —$(CH_2)_9$—. In some embodiments, L is —$(CH_2)_{10}$—.

In certain embodiments, L is an optionally substituted alkenylene, e.g., optionally substituted $C_{2-50}$alkenylene, optionally substituted $C_{2-40}$alkenylene, optionally substituted $C_{2-30}$alkenylene, optionally substituted $C_{2-20}$alkenylene, optionally substituted $C_{4-20}$alkenylene, optionally substituted $C_{6-20}$alkenylene, optionally substituted $C_{8-20}$alkenylene, optionally substituted $C_{10-20}$alkenylene, optionally substituted $C_{2-6}$alkenylene, optionally substituted $C_{3-6}$alkenylene, optionally substituted $C_{4-6}$alkenylene, optionally substituted $C_{4-5}$alkenylene, or optionally substituted $C_{3-4}$alkenylene.

In certain embodiments, L is an optionally substituted alkynylene, e.g., optionally substituted $C_{2-50}$alkynylene, optionally substituted $C_{2-40}$alkynylene, optionally substituted $C_{2-30}$alkynylene, optionally substituted $C_{2-20}$alkynylene, optionally substituted $C_{4-20}$alkynylene, optionally substituted $C_{6-20}$alkynylene, optionally substituted $C_{8-20}$alkynylene, optionally substituted $C_{10-20}$alkynylene, optionally substituted $C_{2-6}$alkynylene, optionally substituted $C_{3-6}$alkynylene, optionally substituted $C_{4-6}$alkynylene, optionally substituted $C_{4-5}$alkynylene, or optionally substituted $C_{3-4}$alkynylene.

In certain embodiments, L is an optionally substituted heteroalkylene; e.g., optionally substituted heteroC$_{1-50}$alkylene, optionally substituted heteroC$_{1-40}$alkylene, optionally substituted heteroC$_{1-30}$alkylene, optionally substituted heteroC$_{1-20}$alkylene, optionally substituted heteroC$_{4-20}$alkylene, optionally substituted heteroC$_{6-20}$alkylene, optionally substituted heteroC$_{8-20}$alkylene, optionally substituted heteroC$_{10-20}$alkylene, optionally substituted heteroC$_{1-6}$alkylene, optionally substituted heteroC$_{2-6}$alkylene, optionally substituted heteroC$_{3-6}$alkylene, optionally substituted heteroC$_{4-6}$alkylene, optionally substituted heteroC$_{4-5}$alkylene, or optionally substituted heteroC$_{3-4}$alkylene. In some embodiments, L is optionally substituted heteroC$_2$alkylene. In some embodiments, L is optionally substituted heteroC$_3$alkylene. In some embodiments, L is optionally substituted heteroC$_4$alkylene. In some embodiments, L is optionally substituted heteroC$_5$alkylene. In some embodiments, L is optionally substituted heteroC$_6$alkylene. In some embodiments, L is optionally substituted heteroC$_7$alkylene. In some embodiments, L is optionally substituted heteroC$_8$alkylene. In some embodiments, L is optionally substituted heteroC$_9$alkylene. In some embodiments, L is optionally substituted heteroC$_{10}$alkylene.

In certain embodiments, L is an optionally substituted heteroalkenylene, e.g., optionally substituted heteroC$_{2-50}$alkenylene, optionally substituted heteroC$_{2-40}$alkenylene, optionally substituted heteroC$_{2-30}$alkenylene, optionally substituted heteroC$_{2-20}$alkenylene, optionally substituted heteroC$_{4-20}$alkenylene, optionally substituted heteroC$_{6-20}$alkenylene, optionally substituted heteroC$_{8-20}$alkenylene, optionally substituted heteroC$_{10-20}$alkenylene, optionally substituted heteroC$_{2-6}$alkenylene, optionally substituted heteroC$_{3-6}$alkenylene, optionally substituted heteroC$_{4-6}$alkenylene, optionally substituted heteroC$_{4-5}$alkenylene, or optionally substituted heteroC$_{3-4}$alkenylene.

In certain embodiments, L is an optionally substituted heteroalkynylene, e.g., optionally substituted heteroC$_{2-50}$alkynylene, optionally substituted heteroC$_{2-40}$alkynylene, optionally substituted heteroC$_{2-30}$alkynylene, optionally substituted heteroC$_{2-20}$alkynylene, optionally substituted heteroC$_{4-20}$alkynylene, optionally substituted heteroC$_{6-20}$alkynylene, optionally substituted heteroC$_{8-20}$alkynylene, optionally substituted heteroC$_{10-20}$alkynylene, optionally substituted heteroC$_{2-6}$alkynylene, optionally substituted heteroC$_{3-6}$alkynylene, optionally substituted heteroC$_{4-6}$alkynylene, optionally substituted heteroC$_{4-5}$alkynylene, or optionally substituted heteroC$_{3-4}$alkynylene.

In certain embodiments, L is an optionally substituted carbocyclylene, e.g., optionally substituted $C_{3-10}$carbocyclylene, optionally substituted $C_{5-8}$carbocyclylene, optionally substituted $C_{5-6}$carbocyclylene, optionally substituted $C_5$carbocyclylene, or optionally substituted $C_6$carbocyclylene.

In certain embodiments, L is an optionally substituted heterocyclylene, e.g., optionally substituted 3-14 membered heterocyclylene, optionally substituted 3-10 membered heterocyclylene, optionally substituted 5-8 membered heterocyclylene, optionally substituted 5-6 membered heterocyclylene, optionally substituted 5-membered heterocyclylene, or optionally substituted 6-membered heterocyclylene.

In certain embodiments, L is an optionally substituted arylene, e.g., optionally substituted phenylene. In some embodiments, L is optionally substituted phenylene. In some embodiments, L is substituted phenylene. In some embodiments, L is unsubstituted phenylene.

In certain embodiments, L is an optionally substituted heteroarylene, e.g., optionally substituted 5-14 membered heteroarylene, optionally substituted 5-10 membered heteroarylene, optionally substituted 5-6 membered heteroarylene, optionally substituted 5-membered heteroarylene, or optionally substituted 6-membered heteroarylene.

In certain embodiments, wherein L is an optionally substituted alkylene group, the group of formula (iv) is a group of the formula

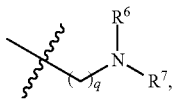

wherein q is an integer between 1 and 50, inclusive, and each of $R^6$ and $R^7$ is independently as defined above and described herein.

In certain embodiments, q is an integer between 1 and 40, inclusive. In certain embodiments, q is an integer between 1 and 30, inclusive. In certain embodiments, q is an integer between 1 and 20, inclusive. In certain embodiments, q is an integer between 1 and 10, inclusive. In certain embodiments, q is an integer between 4 and 20, inclusive. In certain embodiments, q is an integer between 6 and 20, inclusive. In certain embodiments, q is an integer between 2 and 10, inclusive. In certain embodiments, q is an integer between 2 and 9, inclusive. In certain embodiments, q is an integer between 2 and 8, inclusive. In certain embodiments, q is an integer between 2 and 7, inclusive. In certain embodiments, q is an integer between 2 and 6, inclusive. In certain embodiments, q is an integer between 2 and 5, inclusive. In certain embodiments, q is an integer between 2 and 4, inclusive. In certain embodiments, q is an integer between 3 and 10, inclusive. In certain embodiments, q is an integer between 3 and 8, inclusive. In certain embodiments, q is an integer between 3 and 7, inclusive. In certain embodiments, q is an integer between 3 and 6, inclusive. In certain embodiments, q is an integer between 3 and 5, inclusive. In certain embodiments, q is 3 or 4. In certain embodiments, q is an integer between 3 and 9, inclusive. In certain embodiments, q is an integer between 8 and 20, inclusive. In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8. In certain embodiments, q is 9. In certain embodiments, q is 10.

As generally defined above, each $R^6$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii).

In some embodiments, $R^6$ is hydrogen.

In some embodiments, $R^6$ is optionally substituted alkyl. In some embodiments, $R^6$ is optionally substituted $C_{2-50}$ alkyl. In some embodiments, $R^6$ is optionally substituted $C_{2-40}$ alkyl. In some embodiments, $R^6$ is optionally substituted $C_{2-30}$ alkyl. In some embodiments, $R^6$ is optionally substituted $C_{2-20}$ alkyl. In some embodiments, $R^6$ is optionally substituted $C_{2-19}$ alkyl. In some embodiments, $R^6$ is optionally substituted $C_{2-18}$ alkyl. In some embodiments, $R^6$ is optionally substituted $C_{2-17}$ alkyl. In some embodiments, $R^6$ is optionally substituted $C_{2-16}$ alkyl. In some embodiments, $R^6$ is optionally substituted $C_{2-15}$ alkyl. In some embodiments, $R^6$ is optionally substituted $C_{2-14}$ alkyl. In some embodiments, $R^6$ is optionally substituted $C_{2-13}$ alkyl. In some embodiments, $R^6$ is optionally substituted $C_{2-12}$ alkyl. In some embodiments, $R^6$ is optionally substituted $C_{2-11}$ alkyl. In some embodiments, $R^6$ is optionally substituted $C_{2-10}$ alkyl. In some embodiments, $R^6$ is optionally substituted $C_{2-9}$ alkyl. In some embodiments, $R^6$ is optionally substituted $C_{2-8}$ alkyl. In some embodiments, $R^6$ is optionally substituted $C_{2-7}$ alkyl. In some embodiments, $R^6$ is optionally substituted $C_{2-6}$ alkyl.

In some embodiments, $R^6$ is optionally substituted $C_{4-50}$ alkyl. In some embodiments, $R^6$ is optionally substituted $C_{4-40}$ alkyl. In some embodiments, $R^6$ is optionally substituted $C_{4-30}$ alkyl. In some embodiments, $R^6$ is optionally substituted $C_{4-20}$ alkyl. In some embodiments, $R^6$ is optionally substituted $C_{4-19}$ alkyl. In some embodiments, $R^6$ is optionally substituted $C_{4-15}$ alkyl. In some embodiments, $R^6$ is optionally substituted $C_{4-17}$ alkyl. In some embodiments, $R^6$ is optionally substituted $C_{4-16}$ alkyl. In some embodiments, $R^6$ is optionally substituted $C_{4-15}$ alkyl. In some embodiments, $R^6$ is optionally substituted $C_{4-14}$ alkyl. In some embodiments, $R^6$ is optionally substituted $C_{4-13}$ alkyl. In some embodiments, $R^6$ is optionally substituted $C_{4-12}$ alkyl. In some embodiments, $R^6$ is optionally substituted $C_{4-11}$ alkyl. In some embodiments, $R^6$ is optionally substituted $C_{4-10}$ alkyl. In some embodiments, $R^6$ is optionally substituted $C_{4-9}$ alkyl. In some embodiments, $R^6$ is optionally substituted $C_{4-8}$ alkyl. In some embodiments, $R^6$ is optionally substituted $C_{4-7}$ alkyl. In some embodiments, $R^6$ is optionally substituted $C_{4-6}$ alkyl.

In some embodiments, $R^6$ is optionally substituted $C_{6-50}$ alkyl. In some embodiments, $R^6$ is optionally substituted $C_{6-40}$ alkyl. In some embodiments, $R^6$ is optionally substituted $C_{6-30}$ alkyl. In some embodiments, $R^6$ is optionally substituted $C_{6-20}$ alkyl. In some embodiments, $R^6$ is optionally substituted $C_{6-19}$ alkyl. In some embodiments, $R^6$ is optionally substituted $C_{6-18}$ alkyl. In some embodiments, $R^6$ is optionally substituted $C_{6-17}$ alkyl. In some embodiments, $R^6$ is optionally substituted $C_{6-16}$ alkyl. In some embodiments, $R^6$ is optionally substituted $C_{6-15}$ alkyl. In some embodiments, $R^6$ is optionally substituted $C_{6-14}$ alkyl. In some embodiments, $R^6$ is optionally substituted $C_{6-13}$ alkyl. In some embodiments, $R^6$ is optionally substituted $C_{6-12}$ alkyl. In some embodiments, $R^6$ is optionally substituted $C_{6-11}$ alkyl. In some embodiments, $R^6$ is optionally substituted $C_{6-10}$ alkyl. In some embodiments, $R^6$ is optionally substituted $C_{6-9}$ alkyl. In some embodiments, $R^6$ is optionally substituted $C_{6-8}$ alkyl. In some embodiments, $R^6$ is optionally substituted $C_{6-7}$ alkyl.

In some embodiments, $R^6$ is optionally substituted $C_{8-50}$ alkyl. In some embodiments, $R^6$ is optionally substituted $C_{8-40}$ alkyl. In some embodiments, $R^6$ is optionally substituted $C_{8-30}$ alkyl. In some embodiments, $R^6$ is optionally substituted $C_{3-20}$ alkyl. In some embodiments, $R^6$ is optionally substituted $C_{8-19}$ alkyl. In some embodiments, $R^6$ is optionally substituted $C_{8-18}$ alkyl. In some embodiments, $R^6$ is optionally substituted $C_{8-17}$ alkyl. In some embodiments, $R^6$ is optionally substituted $C_{8-16}$ alkyl. In some embodiments, $R^6$ is optionally substituted $C_{8-15}$ alkyl. In some embodiments, $R^6$ is optionally substituted $C_{8-14}$ alkyl. In some embodiments, $R^6$ is optionally substituted $C_{8-13}$ alkyl. In some embodiments, $R^6$ is optionally substituted $C_{8-12}$ alkyl. In some embodiments, $R^6$ is optionally substituted $C_{8-11}$ alkyl. In some embodiments, $R^6$ is optionally substituted $C_{8-10}$ alkyl. In some embodiments, $R^6$ is optionally substituted $C_{8-9}$ alkyl.

In some embodiments, $R^6$ is optionally substituted $C_{9-50}$ alkyl. In some embodiments, $R^6$ is optionally substituted $C_{9-40}$ alkyl. In some embodiments, $R^6$ is optionally substituted $C_{9-30}$ alkyl. In some embodiments, $R^6$ is optionally substituted $C_{9-20}$ alkyl. In some embodiments, $R^6$ is optionally substituted $C_{9-19}$ alkyl. In some embodiments, $R^6$ is optionally substituted $C_{9-15}$ alkyl. In some embodiments, $R^6$ is optionally substituted $C_{9-17}$ alkyl. In some embodiments, $R^6$ is optionally substituted $C_{9-16}$ alkyl. In some embodiments, $R^6$ is optionally substituted $C_{9-15}$ alkyl. In some embodiments, $R^6$ is optionally substituted $C_{9-14}$ alkyl. In some embodiments, $R^6$ is optionally substituted $C_{9-13}$ alkyl. In some embodiments, $R^6$ is optionally substituted $C_{9-12}$ alkyl. In some embodiments, $R^6$ is optionally substituted $C_{9-11}$ alkyl. In some embodiments, $R^6$ is optionally substituted $C_{9-10}$ alkyl.

In some embodiments, $R^6$ is optionally substituted $C_{10-50}$ alkyl. In some embodiments, $R^6$ is optionally substituted $C_{10-40}$ alkyl. In some embodiments, $R^6$ is optionally substituted $C_{10-30}$ alkyl. In some embodiments, $R^6$ is optionally substituted $C_{10-20}$ alkyl. In some embodiments, $R^6$ is optionally substituted $C_{10-19}$ alkyl. In some embodiments, $R^6$ is optionally substituted $C_{10-18}$ alkyl. In some embodiments, $R^6$ is optionally substituted $C_{10-17}$ alkyl. In some embodiments, $R^6$ is optionally substituted $C_{10-16}$ alkyl. In some embodiments, $R^6$ is optionally substituted $C_{10-15}$ alkyl. In some embodiments, $R^6$ is optionally substituted $C_{10-14}$ alkyl. In some embodiments, $R^6$ is optionally substituted $C_{10-13}$ alkyl. In some embodiments, $R^6$ is optionally substituted $C_{10-12}$ alkyl. In some embodiments, $R^6$ is optionally substituted $C_{10-11}$ alkyl.

In some embodiments, $R^6$ is optionally substituted $C_{11-50}$ alkyl. In some embodiments, $R^6$ is optionally substituted $C_{11-40}$ alkyl. In some embodiments, $R^6$ is optionally substituted $C_{11-30}$ alkyl. In some embodiments, $R^6$ is optionally substituted $C_{11-20}$ alkyl. In some embodiments, $R^6$ is optionally substituted $C_{11-19}$ alkyl. In some embodiments, $R^6$ is optionally substituted $C_{11-18}$ alkyl. In some embodiments, $R^6$ is optionally substituted $C_{1-17}$ alkyl. In some embodiments, $R^6$ is optionally substituted $C_{11-16}$ alkyl. In some embodiments, $R^6$ is optionally substituted $C_{11-15}$ alkyl. In some embodiments, $R^6$ is optionally substituted $C_{1-4}$ alkyl. In some embodiments, $R^6$ is optionally substituted $C_{11-13}$ alkyl. In some embodiments, $R^6$ is optionally substituted $C_{11-12}$ alkyl.

In some embodiments, $R^6$ is optionally substituted $C_{12-50}$ alkyl. In some embodiments, $R^6$ is optionally substituted $C_{12-40}$ alkyl. In some embodiments, $R^6$ is optionally substituted $C_{12-30}$ alkyl. In some embodiments, $R^6$ is optionally substituted $C_{12-20}$ alkyl. In some embodiments, $R^6$ is optionally substituted $C_{12-19}$ alkyl. In some embodiments, $R^6$ is optionally substituted $C_{12-18}$ alkyl. In some embodiments, $R^6$ is optionally substituted $C_{12-17}$ alkyl. In some embodiments, $R^6$ is optionally substituted $C_{12-16}$ alkyl. In some embodiments, $R^6$ is optionally substituted $C_{12-15}$ alkyl. In some embodiments, $R^6$ is optionally substituted $C_{12-14}$ alkyl. In some embodiments, $R^6$ is optionally substituted $C_{12-13}$ alkyl.

In some embodiments, $R^6$ is optionally substituted $C_6$ alkyl. In some embodiments, $R^6$ is optionally substituted $C_7$ alkyl. In some embodiments, $R^6$ is optionally substituted $C_8$ alkyl. In some embodiments, $R^6$ is optionally substituted $C_9$ alkyl. In some embodiments, $R^6$ is optionally substituted $C_{10}$ alkyl. In some embodiments, $R^6$ is optionally substituted $C_{11}$ alkyl. In some embodiments, $R^6$ is optionally substituted $C_{12}$ alkyl. In some embodiments, $R^6$ is optionally substituted $C_{13}$ alkyl. In some embodiments, $R^6$ is optionally substituted $C_{14}$ alkyl. In some embodiments, $R^6$ is optionally substituted $C_{15}$ alkyl. In some embodiments, $R^6$ is optionally substituted $C_{16}$ alkyl. In some embodiments, $R^6$ is optionally substituted $C_{17}$ alkyl. In some embodiments, $R^6$ is optionally substituted $C_{18}$ alkyl. In some embodiments, $R^6$ is optionally substituted $C_{19}$ alkyl. In some embodiments, $R^6$ is optionally substituted $C_{20}$ alkyl.

In some embodiments, for example, in any of the above embodiments, $R^6$ is a substituted alkyl group. In some embodiments, $R^6$ is an unsubstituted alkyl group. In some embodiments, $R^6$ is an optionally substituted straight-chain alkyl group. In some embodiments, $R^6$ is a substituted straight-chain alkyl group. In some embodiments, $R^6$ is an unsubstituted straight-chain alkyl group. In some embodiments, $R^6$ is an optionally substituted branched alkyl group. In some embodiments, $R^6$ is a substituted branched alkyl group. In some embodiments, $R^6$ is an unsubstituted branched alkyl group.

In some embodiments, $R^6$ is optionally substituted alkenyl. In some embodiments, $R^6$ is optionally substituted $C_{2-50}$ alkenyl. In some embodiments, $R^6$ is optionally substituted $C_{2-40}$ alkenyl. In some embodiments, $R^6$ is optionally substituted $C_{2-30}$ alkenyl. In some embodiments, $R^6$ is optionally substituted $C_{2-20}$ alkenyl. In some embodiments, $R^6$ is optionally substituted $C_{2-19}$ alkenyl. In some embodiments, $R^6$ is optionally substituted $C_{2-18}$ alkenyl. In some embodiments, $R^6$ is optionally substituted $C_{2-17}$ alkenyl. In some embodiments, $R^6$ is optionally substituted $C_{2-16}$ alkenyl. In some embodiments, $R^6$ is optionally substituted $C_{2-15}$ alkenyl. In some embodiments, $R^6$ is optionally substituted $C_{2-14}$ alkenyl. In some embodiments, $R^6$ is optionally substituted $C_{2-13}$ alkenyl. In some embodiments, $R^6$ is optionally substituted $C_{2-12}$ alkenyl. In some embodiments, $R^6$ is optionally substituted $C_{2-11}$ alkenyl. In some embodiments, $R^6$ is optionally substituted $C_{2-10}$ alkenyl. In some embodiments, $R^6$ is optionally substituted $C_{2-9}$ alkenyl. In some embodiments, $R^6$ is optionally substituted $C_{2-8}$ alkenyl. In some embodiments, $R^6$ is optionally substituted $C_{2-7}$ alkenyl. In some embodiments, $R^6$ is optionally substituted $C_{2-6}$ alkenyl.

In some embodiments, $R^6$ is optionally substituted $C_{4-50}$ alkenyl. In some embodiments, $R^6$ is optionally substituted $C_{4-40}$ alkenyl. In some embodiments, $R^6$ is optionally substituted $C_{4-30}$ alkenyl. In some embodiments, $R^6$ is optionally substituted $C_{4-20}$ alkenyl. In some embodiments, $R^6$ is optionally substituted $C_{4-19}$ alkenyl. In some embodiments, $R^6$ is optionally substituted $C_{4-18}$ alkenyl. In some embodiments, $R^6$ is optionally substituted $C_{4-17}$ alkenyl. In some embodiments, $R^6$ is optionally substituted $C_{4-16}$ alkenyl. In some embodiments, $R^6$ is optionally substituted $C_{4-15}$ alkenyl. In some embodiments, $R^6$ is optionally substituted $C_{4-14}$ alkenyl. In some embodiments, $R^6$ is optionally substituted $C_{4-13}$ alkenyl. In some embodiments, $R^6$ is optionally substituted $C_{4-12}$ alkenyl. In some embodiments, $R^6$ is optionally substituted $C_{4-11}$ alkenyl. In some embodiments, $R^6$ is optionally substituted $C_{4-10}$ alkenyl. In some embodiments, $R^6$ is optionally substituted $C_{4-9}$ alkenyl. In some embodiments, $R^6$ is optionally substituted $C_{4-8}$ alkenyl. In some embodiments, $R^6$ is optionally substituted $C_{4-7}$ alkenyl. In some embodiments, $R^6$ is optionally substituted $C_{4-6}$ alkenyl.

In some embodiments, $R^6$ is optionally substituted $C_{6-50}$ alkenyl. In some embodiments, $R^6$ is optionally substituted $C_{6-40}$ alkenyl. In some embodiments, $R^6$ is optionally substituted $C_{6-30}$ alkenyl. In some embodiments, $R^6$ is optionally substituted $C_{6-20}$ alkenyl. In some embodiments, $R^6$ is optionally substituted $C_{6-19}$ alkenyl. In some embodiments, $R^6$ is optionally substituted $C_{6-18}$ alkenyl. In some embodiments, $R^6$ is optionally substituted $C_{6-17}$ alkenyl. In some embodiments, $R^6$ is optionally substituted $C_{6-16}$ alkenyl. In some embodiments, $R^6$ is optionally substituted $C_{6-15}$ alkenyl. In some embodiments, $R^6$ is optionally substituted $C_{6-14}$ alkenyl. In some embodiments, $R^6$ is optionally substituted $C_{6-13}$ alkenyl. In some embodiments, $R^6$ is optionally substituted $C_{6-12}$ alkenyl. In some embodiments, $R^6$ is optionally substituted $C_{6-11}$ alkenyl. In some embodiments, $R^6$ is optionally substituted $C_{6-10}$ alkenyl. In some embodiments, $R^6$ is optionally substituted $C_{6-9}$ alkenyl. In some embodiments, $R^6$ is optionally substituted $C_{6-8}$ alkenyl. In some embodiments, $R^6$ is optionally substituted $C_{6-7}$ alkenyl.

In some embodiments, $R^6$ is optionally substituted $C_{8-50}$ alkenyl. In some embodiments, $R^6$ is optionally substituted $C_{8-40}$ alkenyl. In some embodiments, $R^6$ is optionally substituted $C_{8-30}$ alkenyl. In some embodiments, $R^6$ is optionally substituted $C_{8-20}$ alkenyl. In some embodiments, $R^6$ is optionally substituted $C_{8-19}$ alkenyl. In some embodiments, $R^6$ is optionally substituted $C_{8-18}$ alkenyl. In some embodiments, $R^6$ is optionally substituted $C_{8-17}$ alkenyl. In some embodiments, $R^6$ is optionally substituted $C_{8-16}$ alkenyl. In some embodiments, $R^6$ is optionally substituted $C_{8-15}$ alkenyl. In some embodiments, $R^6$ is optionally substituted $C_{8-14}$ alkenyl. In some embodiments, $R^6$ is optionally substituted $C_{8-13}$ alkenyl. In some embodiments, $R^6$ is optionally substituted $C_{8-12}$ alkenyl. In some embodiments, $R^6$ is optionally substituted $C_{8-11}$ alkenyl. In some embodiments, $R^6$ is optionally substituted $C_{8-10}$ alkenyl. In some embodiments, $R^6$ is optionally substituted $C_{8-9}$ alkenyl.

In some embodiments, $R^6$ is optionally substituted $C_{9-50}$ alkenyl. In some embodiments, $R^6$ is optionally substituted $C_{9-40}$ alkenyl. In some embodiments, $R^6$ is optionally substituted $C_{9-30}$ alkenyl. In some embodiments, $R^6$ is optionally substituted $C_{9-20}$ alkenyl. In some embodiments, $R^6$ is optionally substituted $C_{9-19}$ alkenyl. In some embodiments, $R^6$ is optionally substituted $C_{9-18}$ alkenyl. In some embodiments, $R^6$ is optionally substituted $C_{9-17}$ alkenyl. In some embodiments, $R^6$ is optionally substituted $C_{9-16}$ alkenyl. In some embodiments, $R^6$ is optionally substituted $C_{9-15}$ alkenyl. In some embodiments, $R^6$ is optionally substituted $C_{9-14}$ alkenyl. In some embodiments, $R^6$ is optionally substituted $C_{9-13}$ alkenyl. In some embodiments, $R^6$ is optionally substituted $C_{9-12}$ alkenyl. In some embodiments, $R^6$ is optionally substituted $C_{9-11}$ alkenyl. In some embodiments, $R^6$ is optionally substituted $C_{9-10}$ alkenyl.

In some embodiments, $R^6$ is optionally substituted $C_{10-50}$ alkenyl. In some embodiments, $R^6$ is optionally substituted $C_{10-40}$ alkenyl. In some embodiments, $R^6$ is optionally substituted $C_{10-30}$ alkenyl. In some embodiments, $R^6$ is optionally substituted $C_{10-20}$ alkenyl. In some embodiments, $R^6$ is optionally substituted $C_{10-19}$ alkenyl. In some embodiments, $R^6$ is optionally substituted $C_{10-18}$ alkenyl. In some embodiments, $R^6$ is optionally substituted $C_{10-17}$ alkenyl. In some embodiments, $R^6$ is optionally substituted $C_{10-16}$ alkenyl. In some embodiments, $R^6$ is optionally substituted $C_{10-15}$ alkenyl. In some embodiments, $R^6$ is optionally substituted $C_{10-14}$ alkenyl. In some embodiments, $R^6$ is optionally substituted $C_{10-13}$ alkenyl. In some embodiments, $R^6$ is optionally substituted $C_{10-12}$ alkenyl. In some embodiments, $R^6$ is optionally substituted $C_{10-11}$ alkenyl.

In some embodiments, $R^6$ is optionally substituted $C_{11-50}$ alkenyl. In some embodiments, $R^6$ is optionally substituted $C_{11-40}$ alkenyl. In some embodiments, $R^6$ is optionally substituted $C_{11-30}$ alkenyl. In some embodiments, $R^6$ is optionally substituted $C_{11-20}$ alkenyl. In some embodiments, $R^6$ is optionally substituted $C_{11-19}$ alkenyl. In some embodiments, $R^6$ is optionally substituted $C_{11-18}$ alkenyl. In some embodiments, $R^6$ is optionally substituted $C_{1-17}$ alkenyl. In some embodiments, $R^6$ is optionally substituted $C_{11-16}$ alkenyl. In some embodiments, $R^6$ is optionally substituted $C_{11-15}$ alkenyl. In some embodiments, $R^6$ is optionally substituted $C_{11-14}$ alkenyl. In some embodiments, $R^6$ is optionally substituted $C_{1-3}$ alkenyl. In some embodiments, $R^6$ is optionally substituted $C_{11-12}$ alkenyl.

In some embodiments, $R^6$ is optionally substituted $C_{12-50}$ alkenyl. In some embodiments, $R^6$ is optionally substituted $C_{12-40}$ alkenyl. In some embodiments, $R^6$ is optionally substituted $C_{12-30}$ alkenyl. In some embodiments, $R^6$ is optionally substituted $C_{12-20}$ alkenyl. In some embodiments, $R^6$ is optionally substituted $C_{12-19}$ alkenyl. In some embodiments, $R^6$ is optionally substituted $C_{12-18}$ alkenyl. In some embodiments, $R^6$ is optionally substituted $C_{12-17}$ alkenyl. In some embodiments, $R^6$ is optionally substituted $C_{12-16}$ alkenyl. In some embodiments, $R^6$ is optionally substituted $C_{12-15}$ alkenyl. In some embodiments, $R^6$ is optionally substituted $C_{12-14}$ alkenyl. In some embodiments, $R^6$ is optionally substituted $C_{12-13}$ alkenyl.

In some embodiments, $R^6$ is optionally substituted $C_6$ alkenyl. In some embodiments, $R^6$ is optionally substituted $C_7$ alkenyl. In some embodiments, $R^6$ is optionally substituted $C_8$ alkenyl. In some embodiments, $R^6$ is optionally substituted $C_9$ alkenyl. In some embodiments, $R^6$ is optionally substituted $C_{10}$ alkenyl. In some embodiments, $R^6$ is optionally substituted $C_{11}$ alkenyl. In some embodiments, $R^6$ is optionally substituted $C_{12}$ alkenyl. In some embodiments, $R^6$ is optionally substituted $C_{13}$ alkenyl. In some embodiments, $R^6$ is optionally substituted $C_{14}$ alkenyl. In some embodiments, $R^6$ is optionally substituted $C_{15}$ alkenyl. In some embodiments, $R^6$ is optionally substituted $C_{16}$ alkenyl. In some embodiments, $R^6$ is optionally substituted $C_{17}$ alkenyl. In some embodiments, $R^6$ is optionally substituted $C_{18}$ alkenyl. In some embodiments, $R^6$ is optionally substituted $C_{19}$ alkenyl. In some embodiments, $R^6$ is optionally substituted $C_{20}$ alkenyl.

In some embodiments, for example, in any of the above embodiments, $R^6$ is a substituted alkenyl group. In some embodiments, $R^6$ is an unsubstituted alkenyl group. In some embodiments, $R^6$ is an optionally substituted straight-chain alkenyl group. In some embodiments, $R^6$ is a substituted straight-chain alkenyl group. In some embodiments, $R^6$ is an unsubstituted straight-chain alkenyl group. In some embodiments, $R^6$ is an optionally substituted branched alkenyl group. In some embodiments, $R^6$ is a substituted branched alkenyl group. In some embodiments, $R^6$ is an unsubstituted branched alkenyl group.

In some embodiments, $R^6$ is optionally substituted alkynyl. In some embodiments, $R^6$ is optionally substituted $C_{2-50}$ alkynyl. In some embodiments, $R^6$ is optionally substituted $C_{2-40}$ alkynyl. In some embodiments, $R^6$ is optionally substituted $C_{2-30}$ alkynyl. In some embodiments, $R^6$ is optionally substituted $C_{2-20}$ alkynyl. In some embodiments, $R^6$ is optionally substituted $C_{2-19}$ alkynyl. In some embodiments, $R^6$ is optionally substituted $C_{2-18}$ alkynyl. In some embodiments, $R^6$ is optionally substituted $C_{2-17}$ alkynyl. In some embodiments, $R^6$ is optionally substituted $C_{2-16}$ alkynyl. In some embodiments, $R^6$ is optionally substituted $C_{2-15}$ alkynyl. In some embodiments, $R^6$ is optionally substituted $C_{2-14}$ alkynyl. In some embodiments, $R^6$ is optionally substituted $C_{2-13}$ alkynyl. In some embodiments, $R^6$ is optionally substituted $C_{2-12}$ alkynyl. In some embodiments, $R^6$ is optionally substituted $C_{2-11}$ alkynyl. In some embodiments, $R^6$ is optionally substituted $C_{2-10}$ alkynyl. In some embodiments, $R^6$ is optionally substituted $C_{2-9}$ alkynyl. In some embodiments, $R^6$ is optionally substituted $C_{2-8}$ alkynyl. In some embodiments, $R^6$ is optionally substituted $C_{2-7}$ alkynyl. In some embodiments, $R^6$ is optionally substituted $C_{2-6}$ alkynyl.

In some embodiments, $R^6$ is optionally substituted $C_{4-50}$ alkynyl. In some embodiments, $R^6$ is optionally substituted $C_{4-40}$ alkynyl. In some embodiments, $R^6$ is optionally substituted $C_{4-30}$ alkynyl. In some embodiments, $R^6$ is optionally substituted $C_{4-20}$ alkynyl. In some embodiments, $R^6$ is optionally substituted $C_{4-19}$ alkynyl. In some embodiments, $R^6$ is optionally substituted $C_{4-18}$ alkynyl. In some embodiments, $R^6$ is optionally substituted $C_{4-17}$ alkynyl. In some embodiments, $R^6$ is optionally substituted $C_{4-16}$ alkynyl. In some embodiments, $R^6$ is optionally substituted $C_{4-15}$ alkynyl. In some embodiments, $R^6$ is optionally substituted $C_{4-14}$ alkynyl. In some embodiments, $R^6$ is optionally substituted $C_{4-13}$ alkynyl. In some embodiments, $R^6$ is optionally substituted $C_{4-12}$ alkynyl. In some embodiments, $R^6$ is optionally substituted $C_{4-11}$ alkynyl. In some embodiments, $R^6$ is optionally substituted $C_{4-10}$ alkynyl. In some embodiments, $R^6$ is optionally substituted $C_{4-9}$ alkynyl. In some embodiments, $R^6$ is optionally substituted $C_{4-8}$ alkynyl. In some embodiments, $R^6$ is optionally substituted $C_{4-7}$ alkynyl. In some embodiments, $R^6$ is optionally substituted $C_{4-6}$ alkynyl.

In some embodiments, $R^6$ is optionally substituted $C_{6-50}$ alkynyl. In some embodiments, $R^6$ is optionally substituted $C_{6-40}$ alkynyl. In some embodiments, $R^6$ is optionally substituted $C_{6-30}$ alkynyl. In some embodiments, $R^6$ is optionally substituted $C_{6-20}$ alkynyl. In some embodiments, $R^6$ is optionally substituted $C_{6-19}$ alkynyl. In some embodiments, $R^6$ is optionally substituted $C_{6-18}$ alkynyl. In some embodiments, $R^6$ is optionally substituted $C_{6-17}$ alkynyl. In some embodiments, $R^6$ is optionally substituted $C_{6-16}$ alkynyl. In some embodiments, $R^6$ is optionally substituted $C_{6-15}$ alkynyl. In some embodiments, $R^6$ is optionally substituted $C_{6-14}$ alkynyl. In some embodiments, $R^6$ is optionally substituted $C_{6-13}$ alkynyl. In some embodiments, $R^6$ is optionally substituted $C_{6-12}$ alkynyl. In some embodiments, $R^6$ is optionally substituted $C_{6-11}$ alkynyl. In some embodiments, $R^6$ is optionally substituted $C_{6-10}$ alkynyl. In some embodiments, $R^6$ is optionally substituted $C_{6-9}$ alkynyl. In some embodiments, $R^6$ is optionally substituted $C_{6-8}$ alkynyl. In some embodiments, $R^6$ is optionally substituted $C_{6-7}$ alkynyl.

In some embodiments, $R^6$ is optionally substituted $C_{8-50}$ alkynyl. In some embodiments, $R^6$ is optionally substituted $C_{8-40}$ alkynyl. In some embodiments, $R^6$ is optionally substituted $C_{8-30}$ alkynyl. In some embodiments, $R^6$ is optionally substituted $C_{3-20}$ alkynyl. In some embodiments, $R^6$ is optionally substituted $C_{8-19}$ alkynyl. In some embodiments, $R^6$ is optionally substituted $C_{8-18}$ alkynyl. In some embodiments, $R^6$ is optionally substituted $C_{8-17}$ alkynyl. In some embodiments, $R^6$ is optionally substituted $C_{3-16}$ alkynyl. In some embodiments, $R^6$ is optionally substituted $C_{8-15}$ alkynyl. In some embodiments, $R^6$ is optionally substituted $C_{8-14}$ alkynyl. In some embodiments, $R^6$ is optionally substituted $C_{8-13}$ alkynyl. In some embodiments, $R^6$ is optionally substituted $C_{8-12}$ alkynyl. In some embodiments, $R^6$ is optionally substituted $C_{8-11}$ alkynyl. In some embodiments, $R^6$ is optionally substituted $C_{8-10}$ alkynyl. In some embodiments, $R^6$ is optionally substituted $C_{8-9}$ alkynyl.

In some embodiments, $R^6$ is optionally substituted $C_{9-50}$ alkynyl. In some embodiments, $R^6$ is optionally substituted $C_{9-40}$ alkynyl. In some embodiments, $R^6$ is optionally substituted $C_{9-30}$ alkynyl. In some embodiments, $R^6$ is optionally substituted $C_{9-20}$ alkynyl. In some embodiments, $R^6$ is optionally substituted $C_{9-19}$ alkynyl. In some embodiments, $R^6$ is optionally substituted $C_{9-18}$ alkynyl. In some embodiments, $R^6$ is optionally substituted $C_{9-17}$ alkynyl. In some embodiments, $R^6$ is optionally substituted $C_{9-16}$ alkynyl. In some embodiments, $R^6$ is optionally substituted $C_{9-15}$ alkynyl. In some embodiments, $R^6$ is optionally substituted $C_{9-14}$ alkynyl. In some embodiments, $R^6$ is optionally substituted $C_{9-13}$ alkynyl. In some embodiments, $R^6$ is optionally substituted $C_{9-12}$ alkynyl. In some embodiments, $R^6$ is optionally substituted $C_{9-11}$ alkynyl. In some embodiments, $R^6$ is optionally substituted $C_{9-10}$ alkynyl.

In some embodiments, $R^6$ is optionally substituted $C_{10-50}$ alkynyl. In some embodiments, $R^6$ is optionally substituted $C_{10-40}$ alkynyl. In some embodiments, $R^6$ is optionally substituted $C_{10-30}$ alkynyl. In some embodiments, $R^6$ is optionally substituted $C_{10-20}$ alkynyl. In some embodiments, $R^6$ is optionally substituted $C_{10-19}$ alkynyl. In some embodiments, $R^6$ is optionally substituted $C_{10-18}$ alkynyl. In some embodiments, $R^6$ is optionally substituted $C_{10-17}$ alkynyl. In some embodiments, $R^6$ is optionally substituted $C_{10-16}$ alkynyl. In some embodiments, $R^6$ is optionally substituted $C_{10-15}$ alkynyl. In some embodiments, $R^6$ is optionally substituted $C_{10-14}$ alkynyl. In some embodiments, $R^6$ is optionally substituted $C_{10-13}$ alkynyl. In some embodiments, $R^6$ is optionally substituted $C_{10-12}$ alkynyl. In some embodiments, $R^6$ is optionally substituted $C_{10-11}$ alkynyl.

In some embodiments, $R^6$ is optionally substituted $C_{11-50}$ alkynyl. In some embodiments, $R^6$ is optionally substituted $C_{11-40}$ alkynyl. In some embodiments, $R^6$ is optionally substituted $C_{11-30}$ alkynyl. In some embodiments, $R^6$ is optionally substituted $C_{11-20}$ alkynyl. In some embodiments, $R^6$ is optionally substituted $C_{11-19}$ alkynyl. In some embodiments, $R^6$ is optionally substituted $C_{11-18}$ alkynyl. In some embodiments, $R^6$ is optionally substituted $C_{11-17}$ alkynyl. In some embodiments, $R^6$ is optionally substituted $C_{11-16}$ alkynyl. In some embodiments, $R^6$ is optionally substituted $C_{11-15}$ alkynyl. In some embodiments, $R^6$ is optionally substituted $C_{11-14}$ alkynyl. In some embodiments, $R^6$ is optionally substituted $C_{11-13}$ alkynyl. In some embodiments, $R^6$ is optionally substituted $C_{11-12}$ alkynyl.

In some embodiments, $R^6$ is optionally substituted $C_{12-50}$ alkynyl. In some embodiments, $R^6$ is optionally substituted $C_{12-40}$ alkynyl. In some embodiments, $R^6$ is optionally substituted $C_{12-30}$ alkynyl. In some embodiments, $R^6$ is optionally substituted $C_{12-20}$ alkynyl. In some embodiments, $R^6$ is optionally substituted $C_{12-19}$ alkynyl. In some embodiments, $R^6$ is optionally substituted $C_{12-18}$ alkynyl. In some embodiments, $R^6$ is optionally substituted $C_{12-17}$ alkynyl. In some embodiments, $R^6$ is optionally substituted $C_{12-16}$ alkynyl. In some embodiments, $R^6$ is optionally substituted $C_{12-15}$ alkynyl. In some embodiments, $R^6$ is optionally substituted $C_{12-14}$ alkynyl. In some embodiments, $R^6$ is optionally substituted $C_{12-13}$ alkynyl.

In some embodiments, $R^6$ is optionally substituted $C_6$ alkynyl. In some embodiments, $R^6$ is optionally substituted $C_7$ alkynyl. In some embodiments, $R^6$ is optionally substituted $C_8$ alkynyl. In some embodiments, $R^6$ is optionally substituted $C_9$ alkynyl. In some embodiments, $R^6$ is optionally substituted $C_{10}$ alkynyl. In some embodiments, $R^6$ is optionally substituted $C_{11}$ alkynyl. In some embodiments, $R^6$ is optionally substituted $C_{12}$ alkynyl. In some embodiments, $R^6$ is optionally substituted $C_{13}$ alkynyl. In some embodiments, $R^6$ is optionally substituted $C_{14}$ alkynyl. In some embodiments, $R^6$ is optionally substituted $C_{15}$ alkynyl. In some embodiments, $R^6$ is optionally substituted $C_{16}$ alkynyl. In some embodiments, $R^6$ is optionally substituted $C_{17}$ alkynyl. In some embodiments, $R^6$ is optionally substituted $C_{18}$ alkynyl. In some embodiments, $R^6$ is optionally substituted $C_{19}$ alkynyl. In some embodiments, $R^6$ is optionally substituted $C_{20}$ alkynyl.

In some embodiments, for example, in any of the above embodiments, $R^6$ is a substituted alkynyl group. In some embodiments, $R^6$ is an unsubstituted alknyl group. In some embodiments, $R^6$ is an optionally substituted straight-chain alkynyl group. In some embodiments, $R^6$ is a substituted straight-chain alkynyl group. In some embodiments, $R^6$ is an unsubstituted straight-chain alkynyl group. In some embodiments, $R^6$ is an optionally substituted branched alkynyl group. In some embodiments, $R^6$ is a substituted branched alkynyl group. In some embodiments, $R^6$ is an unsubstituted branched alkynyl group.

In some embodiments, $R^6$ is optionally substituted carbocyclyl. In some embodiments, $R^6$ is optionally substituted heterocyclyl. In some embodiments, $R^6$ is optionally substituted aryl. In some embodiments, $R^6$ is optionally substituted heteroaryl. In some embodiments, $R^6$ is a nitrogen protecting group.

In some embodiments, $R^6$ is a group of formula (i). In some embodiments, $R^6$ is a group of formula (i-a). In some embodiments, $R^6$ is a group of formula

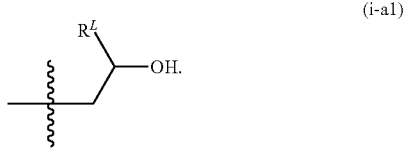

(i-a1)

In some embodiments, $R^6$ is a group of formula (i-b). In some embodiments, R is a group of formula (ii). In some embodiments, $R^6$ is a group of formula (iii).

In some embodiments, $R^6$ is substituted with one or more hydroxyl groups. In some embodiments, $R^6$ is substituted with one hydroxyl group. In some embodiments, $R^6$ is substituted with one 2-hydroxyl group (C1 is the carbon atom directly bonded to the nitrogen atom depicted in formula (iv)).

As generally defined above, each R is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii).

In some embodiments, $R^7$ is hydrogen.

In some embodiments, $R^7$ is optionally substituted alkyl. In some embodiments, $R^7$ is optionally substituted $C_{2-50}$ alkyl. In some embodiments, R is optionally substituted $C_{2-40}$ alkyl. In some embodiments, $R^7$ is optionally substituted $C_{2-30}$ alkyl. In some embodiments, $R^7$ is optionally substituted $C_{2-20}$ alkyl. In some embodiments, $R^7$ is optionally substituted $C_{2-19}$ alkyl. In some embodiments, $R^7$ is optionally substituted $C_{2-18}$ alkyl. In some embodiments, $R^7$ is optionally substituted $C_{2-17}$ alkyl. In some embodiments, $R^7$ is optionally substituted $C_{2-16}$ alkyl. In some embodiments, $R^7$ is optionally substituted $C_{2-15}$ alkyl. In some embodiments, $R^7$ is optionally substituted $C_{2-14}$ alkyl. In some embodiments, $R^7$ is optionally substituted $C_{2-13}$ alkyl. In some embodiments, $R^7$ is optionally substituted $C_{2-12}$ alkyl. In some embodiments, $R^7$ is optionally substituted $C_{2-11}$ alkyl. In some embodiments, $R^7$ is optionally substituted $C_{2-10}$ alkyl. In some embodiments, $R^7$ is optionally substituted $C_{2-9}$ alkyl. In some embodiments, $R^7$ is optionally substituted $C_{2-8}$ alkyl. In some embodiments, $R^7$ is optionally substituted $C_{2-7}$ alkyl. In some embodiments, $R^7$ is optionally substituted $C_{2-6}$ alkyl.

In some embodiments, $R^7$ is optionally substituted $C_{4-50}$ alkyl. In some embodiments, $R^7$ is optionally substituted $C_{4-40}$ alkyl. In some embodiments, $R^7$ is optionally substituted $C_{4-30}$ alkyl. In some embodiments, $R^7$ is optionally substituted $C_{4-20}$ alkyl. In some embodiments, $R^7$ is optionally substituted $C_{4-19}$ alkyl. In some embodiments, $R^7$ is optionally substituted $C_{4-18}$ alkyl. In some embodiments, $R^7$ is optionally substituted $C_{4-17}$ alkyl. In some embodiments, $R^7$ is optionally substituted $C_{4-16}$ alkyl. In some embodiments, $R^7$ is optionally substituted $C_{4-15}$ alkyl. In some embodiments, $R^7$ is optionally substituted $C_{4-14}$ alkyl. In some embodiments, $R^7$ is optionally substituted $C_{4-13}$ alkyl. In some embodiments, $R^7$ is optionally substituted $C_{4-12}$ alkyl. In some embodiments, $R^7$ is optionally substituted $C_{4-11}$ alkyl. In some embodiments, $R^7$ is optionally substituted $C_{4-10}$ alkyl. In some embodiments, $R^7$ is optionally substituted $C_{4-9}$ alkyl. In some embodiments, $R^7$ is optionally substituted $C_{4-8}$ alkyl. In some embodiments, $R^7$ is optionally substituted $C_{4-7}$ alkyl. In some embodiments, $R^7$ is optionally substituted $C_{4-6}$ alkyl.

In some embodiments, $R^7$ is optionally substituted $C_{6-50}$ alkyl. In some embodiments, $R^7$ is optionally substituted $C_{6-40}$ alkyl. In some embodiments, $R^7$ is optionally substituted $C_{6-30}$ alkyl. In some embodiments, $R^7$ is optionally substituted $C_{6-20}$ alkyl. In some embodiments, $R^7$ is optionally substituted $C_{6-19}$ alkyl. In some embodiments, $R^7$ is optionally substituted $C_{6-18}$ alkyl. In some embodiments, $R^7$ is optionally substituted $C_{6-17}$ alkyl. In some embodiments, $R^7$ is optionally substituted $C_{6-16}$ alkyl. In some embodiments, $R^7$ is optionally substituted $C_{6-15}$ alkyl. In some embodiments, $R^7$ is optionally substituted $C_{6-14}$ alkyl. In some embodiments, $R^7$ is optionally substituted $C_{6-13}$ alkyl. In some embodiments, $R^7$ is optionally substituted $C_{6-12}$ alkyl. In some embodiments, $R^7$ is optionally substituted $C_{6-11}$ alkyl. In some embodiments, $R^7$ is optionally substituted $C_{6-10}$ alkyl. In some embodiments, $R^7$ is optionally substituted $C_{6-9}$ alkyl. In some embodiments, $R^7$ is optionally substituted $C_{6-8}$ alkyl. In some embodiments, $R^7$ is optionally substituted $C_{6-7}$ alkyl.

In some embodiments, $R^7$ is optionally substituted $C_{8-50}$ alkyl. In some embodiments, $R^7$ is optionally substituted $C_{8-40}$ alkyl. In some embodiments, $R^7$ is optionally substituted $C_{8-30}$ alkyl. In some embodiments, $R^7$ is optionally substituted $C_{8-20}$ alkyl. In some embodiments, $R^7$ is optionally substituted $C_{8-19}$ alkyl. In some embodiments, $R^7$ is optionally substituted $C_{8-18}$ alkyl. In some embodiments, $R^7$ is optionally substituted $C_{8-17}$ alkyl. In some embodiments, $R^7$ is optionally substituted $C_{8-16}$ alkyl. In some embodiments, $R^7$ is optionally substituted $C_{8-15}$ alkyl. In some embodiments, $R^7$ is optionally substituted $C_{8-14}$ alkyl. In some embodiments, $R^7$ is optionally substituted $C_{8-13}$ alkyl. In some embodiments, $R^7$ is optionally substituted $C_{8-12}$ alkyl. In some embodiments, $R^7$ is optionally substituted $C_{8-11}$ alkyl. In some embodiments, $R^7$ is optionally substituted $C_{8-10}$ alkyl. In some embodiments, $R^7$ is optionally substituted $C_{8-9}$ alkyl.

In some embodiments, $R^7$ is optionally substituted $C_{9-50}$ alkyl. In some embodiments, $R^7$ is optionally substituted $C_{9-40}$ alkyl. In some embodiments, $R^7$ is optionally substituted $C_{9-30}$ alkyl. In some embodiments, $R^7$ is optionally substituted $C_{9-20}$ alkyl. In some embodiments, $R^7$ is optionally substituted $C_{9-19}$ alkyl. In some embodiments, $R^7$ is optionally substituted $C_{9-18}$ alkyl. In some embodiments, $R^7$ is optionally substituted $C_{9-17}$ alkyl. In some embodiments, $R^7$ is optionally substituted $C_{9-16}$ alkyl. In some embodiments, $R^7$ is optionally substituted $C_{9-15}$ alkyl. In some embodiments, $R^7$ is optionally substituted $C_{9-14}$ alkyl. In some embodiments, $R^7$ is optionally substituted $C_{9-13}$ alkyl. In some embodiments, $R^7$ is optionally substituted $C_{9-12}$ alkyl. In some embodiments, $R^7$ is optionally substituted $C_{9-11}$ alkyl. In some embodiments, $R^7$ is optionally substituted $C_{9-10}$ alkyl.

In some embodiments, $R^7$ is optionally substituted $C_{10-50}$ alkyl. In some embodiments, $R^7$ is optionally substituted $C_{10-40}$ alkyl. In some embodiments, $R^7$ is optionally substituted $C_{10-30}$ alkyl. In some embodiments, $R^7$ is optionally substituted $C_{10-20}$ alkyl. In some embodiments, $R^7$ is optionally substituted $C_{10-19}$ alkyl. In some embodiments, $R^7$ is optionally substituted $C_{10-18}$ alkyl. In some embodiments, $R^7$ is optionally substituted $C_{10-17}$ alkyl. In some embodiments, $R^7$ is optionally substituted $C_{10-16}$ alkyl. In some embodiments, $R^7$ is optionally substituted $C_{10-15}$ alkyl. In some embodiments, R is optionally substituted $C_{10-14}$ alkyl. In some embodiments, $R^7$ is optionally substituted $C_{10-13}$ alkyl. In some embodiments, $R^7$ is optionally substituted $C_{10-12}$ alkyl. In some embodiments, $R^7$ is optionally substituted $C_{10-11}$ alkyl.

In some embodiments, $R^7$ is optionally substituted $C_{11-50}$ alkyl. In some embodiments, $R^7$ is optionally substituted $C_{11-40}$ alkyl. In some embodiments, $R^7$ is optionally substituted $C_{11-30}$ alkyl. In some embodiments, R is optionally substituted $C_{11-20}$ alkyl. In some embodiments, $R^7$ is optionally substituted $C_{11-19}$ alkyl. In some embodiments, $R^7$ is optionally substituted $C_{11-18}$ alkyl. In some embodiments, R is optionally substituted $C_{1-17}$ alkyl. In some embodiments, R is optionally substituted $C_{11-16}$ alkyl. In some embodiments, $R^7$ is optionally substituted $C_{11-15}$ alkyl. In some embodiments, R is optionally substituted $C_{11-14}$ alkyl. In some embodiments, R is optionally substituted $C_{11-13}$ alkyl. In some embodiments, $R^7$ is optionally substituted $C_{11-12}$ alkyl.

In some embodiments, $R^7$ is optionally substituted $C_{12-50}$ alkyl. In some embodiments, R is optionally substituted $C_{12-40}$ alkyl. In some embodiments, $R^7$ is optionally substituted $C_{12-30}$ alkyl. In some embodiments, $R^7$ is optionally substituted $C_{12-20}$ alkyl. In some embodiments, R is optionally substituted $C_{12-19}$ alkyl. In some embodiments, $R^7$ is optionally substituted $C_{12-18}$ alkyl. In some embodiments, $R^7$ is optionally substituted $C_{12-17}$ alkyl. In some embodiments, R is optionally substituted $C_{12-16}$ alkyl. In some embodiments, $R^7$ is optionally substituted $C_{12-15}$ alkyl. In some embodiments, $R^7$ is optionally substituted $C_{12-14}$ alkyl. In some embodiments, 7 is optionally substituted $C_{12-13}$ alkyl.

In some embodiments, $R^7$ is optionally substituted $C_6$ alkyl. In some embodiments, $R^7$ is optionally substituted $C_7$ alkyl. In some embodiments, $R^7$ is optionally substituted $C_8$ alkyl. In some embodiments, $R^7$ is optionally substituted $C_9$ alkyl. In some embodiments, $R^7$ is optionally substituted $C_{10}$ alkyl. In some embodiments, $R^7$ is optionally substituted $C_{11}$ alkyl. In some embodiments, $R^7$ is optionally substituted $C_{12}$ alkyl. In some embodiments, $R^7$ is optionally substituted $C_{13}$ alkyl. In some embodiments, $R^7$ is optionally substituted $C_{14}$ alkyl. In some embodiments, $R^7$ is optionally substituted $C_{15}$ alkyl. In some embodiments, $R^7$ is optionally substituted $C_{16}$ alkyl. In some embodiments, $R^7$ is optionally substituted $C_{17}$ alkyl. In some embodiments, $R^7$ is optionally substituted $C_{18}$ alkyl. In some embodiments, $R^7$ is optionally substituted $C_{19}$ alkyl. In some embodiments, $R^7$ is optionally substituted $C_{20}$ alkyl.

In some embodiments, for example, in any of the above embodiments, $R^7$ is a substituted alkyl group. In some embodiments, $R^7$ is an unsubstituted alkyl group. In some embodiments, $R^7$ is an optionally substituted straight-chain alkyl group. In some embodiments, $R^7$ is a substituted straight-chain alkyl group. In some embodiments, $R^7$ is an unsubstituted straight-chain alkyl group. In some embodiments, $R^7$ is an optionally substituted branched alkyl group. In some embodiments, $R^7$ is a substituted branched alkyl group. In some embodiments, $R^7$ is an unsubstituted branched alkyl group.

In some embodiments, $R^7$ is optionally substituted alkenyl. In some embodiments, $R^7$ is optionally substituted $C_{2-50}$ alkenyl. In some embodiments, $R^7$ is optionally substituted $C_{2-40}$ alkenyl. In some embodiments, $R^7$ is optionally substituted $C_{2-30}$ alkenyl. In some embodiments, $R^7$ is optionally substituted $C_{2-20}$ alkenyl. In some embodiments, $R^7$ is optionally substituted $C_{2-19}$ alkenyl. In some embodiments, $R^7$ is optionally substituted $C_{2-18}$ alkenyl. In some embodiments, $R^7$ is optionally substituted $C_{2-17}$ alkenyl. In some embodiments, $R^7$ is optionally substituted $C_{2-16}$ alkenyl. In some embodiments, R is optionally substituted $C_{2-15}$ alkenyl. In some embodiments, $R^7$ is optionally substituted $C_{2-14}$ alkenyl. In some embodiments, $R^7$ is optionally substituted $C_{2-13}$ alkenyl. In some embodiments, $R^7$ is optionally substituted $C_{2-12}$ alkenyl. In some embodiments, $R^7$ is optionally substituted $C_{2-11}$ alkenyl. In some embodiments, $R^7$ is optionally substituted $C_{2-10}$ alkenyl. In some embodiments, $R^7$ is optionally substituted $C_{2-9}$ alkenyl. In some embodiments, $R^7$ is optionally substituted $C_{2-8}$ alkenyl. In some embodiments, $R^7$ is optionally substituted $C_{2-7}$ alkenyl. In some embodiments, $R^7$ is optionally substituted $C_{2-6}$ alkenyl.

In some embodiments, $R^7$ is optionally substituted $C_{4-50}$ alkenyl. In some embodiments, $R^7$ is optionally substituted $C_{4-40}$ alkenyl. In some embodiments, $R^7$ is optionally substituted $C_{4-30}$ alkenyl. In some embodiments, $R^7$ is optionally substituted $C_{4-20}$ alkenyl. In some embodiments, $R^7$ is optionally substituted $C_{4-19}$ alkenyl. In some embodiments, $R^7$ is optionally substituted $C_{4-18}$ alkenyl. In some embodiments, $R^7$ is optionally substituted $C_{4-17}$ alkenyl. In some embodiments, $R^7$ is optionally substituted $C_{4-16}$ alkenyl. In some embodiments, $R^7$ is optionally substituted $C_{4-15}$ alkenyl. In some embodiments, R is optionally substituted $C_{4-14}$ alkenyl. In some embodiments, $R^7$ is optionally substituted $C_{4-13}$ alkenyl. In some embodiments, $R^7$ is optionally substituted $C_{4-12}$ alkenyl. In some embodiments, $R^7$ is optionally substituted $C_{4-11}$ alkenyl. In some embodiments, $R^7$ is optionally substituted $C_{4-10}$ alkenyl. In some embodiments, $R^7$ is optionally substituted $C_{4-9}$ alkenyl. In some embodiments, $R^7$ is optionally substituted $C_{4-8}$ alkenyl. In some embodiments, $R^7$ is optionally substituted $C_{4-7}$ alkenyl. In some embodiments, $R^7$ is optionally substituted $C_{4-6}$ alkenyl.

In some embodiments, $R^7$ is optionally substituted $C_{6-50}$ alkenyl. In some embodiments, $R^7$ is optionally substituted $C_{6-40}$ alkenyl. In some embodiments, $R^7$ is optionally substituted $C_{6-30}$ alkenyl. In some embodiments, $R^7$ is optionally substituted $C_{6-20}$ alkenyl. In some embodiments, $R^7$ is optionally substituted $C_{6-19}$ alkenyl. In some embodiments, $R^7$ is optionally substituted $C_{6-18}$ alkenyl. In some embodiments, $R^7$ is optionally substituted $C_{6-17}$ alkenyl. In some embodiments, $R^7$ is optionally substituted $C_{6-16}$ alkenyl. In some embodiments, $R^7$ is optionally substituted $C_{6-15}$ alkenyl. In some embodiments, $R^7$ is optionally substituted $C_{6-14}$ alkenyl. In some embodiments, $R^7$ is optionally substituted $C_{6-13}$ alkenyl. In some embodiments, $R^7$ is optionally substituted $C_{6-12}$ alkenyl. In some embodiments, $R^7$ is optionally substituted $C_{6-11}$ alkenyl. In some embodiments, $R^7$ is optionally substituted $C_{6-10}$ alkenyl. In some embodiments, $R^7$ is optionally substituted $C_{6-9}$ alkenyl. In some embodiments, $R^7$ is optionally substituted $C_{6-8}$ alkenyl. In some embodiments, $R^7$ is optionally substituted $C_{6-7}$ alkenyl.

In some embodiments, $R^7$ is optionally substituted $C_{8-50}$ alkenyl. In some embodiments, $R^7$ is optionally substituted $C_{8-40}$ alkenyl. In some embodiments, $R^7$ is optionally substituted $C_{8-30}$ alkenyl. In some embodiments, $R^7$ is optionally substituted $C_{8-20}$ alkenyl. In some embodiments, $R^7$ is optionally substituted $C_{8-19}$ alkenyl. In some embodiments, $R^7$ is optionally substituted $C_{8-18}$ alkenyl. In some embodiments, $R^7$ is optionally substituted $C_{8-17}$ alkenyl. In some embodiments, $R^7$ is optionally substituted $C_{8-16}$ alkenyl. In some embodiments, $R^7$ is optionally substituted $C_{8-15}$ alkenyl. In some embodiments, $R^7$ is optionally substituted $C_{8-14}$ alkenyl. In some embodiments, $R^7$ is optionally substituted $C_{8-13}$ alkenyl. In some embodiments, $R^7$ is optionally substituted $C_{8-12}$ alkenyl. In some embodiments, $R^7$ is optionally substituted $C_{8-11}$ alkenyl. In some embodiments, $R^7$ is optionally substituted $C_{8-10}$ alkenyl. In some embodiments, $R^7$ is optionally substituted $C_{8-9}$ alkenyl.

In some embodiments, $R^7$ is optionally substituted $C_{9-50}$ alkenyl. In some embodiments, $R^7$ is optionally substituted $C_{9-40}$ alkenyl. In some embodiments, $R^7$ is optionally substituted $C_{9-30}$ alkenyl. In some embodiments, $R^7$ is optionally substituted $C_{9-20}$ alkenyl. In some embodiments, $R^7$ is optionally substituted $C_{9-19}$ alkenyl. In some embodiments, $R^7$ is optionally substituted $C_{9-18}$ alkenyl. In some embodiments, $R^7$ is optionally substituted $C_{9-17}$ alkenyl. In some embodiments, $R^7$ is optionally substituted $C_{9-16}$ alkenyl. In some embodiments, $R^7$ is optionally substituted $C_{9-15}$ alkenyl. In some embodiments, $R^7$ is optionally substituted $C_{9-14}$ alkenyl. In some embodiments, $R^7$ is optionally substituted $C_{9-13}$ alkenyl. In some embodiments, $R^7$ is optionally substituted $C_{9-12}$ alkenyl. In some embodiments, $R^7$ is optionally substituted $C_{9-11}$ alkenyl. In some embodiments, $R^7$ is optionally substituted $C_{9-10}$ alkenyl.

In some embodiments, $R^7$ is optionally substituted $C_{10-50}$ alkenyl. In some embodiments, $R^7$ is optionally substituted $C_{10-40}$ alkenyl. In some embodiments, $R^7$ is optionally substituted $C_{10-30}$ alkenyl. In some embodiments, $R^7$ is optionally substituted $C_{10-20}$ alkenyl. In some embodiments, $R^7$ is optionally substituted $C_{10-19}$ alkenyl. In some embodiments, $R^7$ is optionally substituted $C_{10-18}$ alkenyl. In some embodiments, $R^7$ is optionally substituted $C_{10-17}$ alkenyl. In some embodiments, $R^7$ is optionally substituted $C_{10-16}$ alkenyl. In some embodiments, $R^7$ is optionally substituted $C_{10-15}$ alkenyl. In some embodiments, $R^7$ is optionally substituted $C_{10-14}$ alkenyl. In some embodiments, $R^7$ is optionally substituted $C_{10-13}$ alkenyl. In some embodiments, $R^7$ is optionally substituted $C_{10-12}$ alkenyl. In some embodiments, $R^7$ is optionally substituted $C_{10-11}$ alkenyl.

In some embodiments, $R^7$ is optionally substituted $C_{11-50}$ alkenyl. In some embodiments, $R^7$ is optionally substituted $C_{10-40}$ alkenyl. In some embodiments, $R^7$ is optionally substituted $C_{11-30}$ alkenyl. In some embodiments, $R^7$ is optionally substituted $C_{11-20}$ alkenyl. In some embodiments, $R^7$ is optionally substituted $C_{11-19}$ alkenyl. In some embodiments, $R^7$ is optionally substituted $C_{11-18}$ alkenyl. In some embodiments, $R^7$ is optionally substituted $C_{11-17}$ alkenyl. In some embodiments, $R^7$ is optionally substituted $C_{11-16}$ alkenyl. In some embodiments, $R^7$ is optionally substituted $C_{11-15}$ alkenyl. In some embodiments, $R^7$ is optionally substituted $C_{11-14}$ alkenyl. In some embodiments, $R^7$ is optionally substituted $C_{11-13}$ alkenyl. In some embodiments, $R^7$ is optionally substituted $C_{1-12}$ alkenyl.

In some embodiments, $R^7$ is optionally substituted $C_{12-50}$ alkenyl. In some embodiments, $R^7$ is optionally substituted $C_{12-40}$ alkenyl. In some embodiments, $R^7$ is optionally substituted $C_{12-30}$ alkenyl. In some embodiments, $R^7$ is optionally substituted $C_{12-20}$ alkenyl. In some embodiments, $R^7$ is optionally substituted $C_{12-19}$ alkenyl. In some embodiments, $R^7$ is optionally substituted $C_{12-18}$ alkenyl. In some embodiments, $R^7$ is optionally substituted $C_{12-17}$ alkenyl. In some embodiments, $R^7$ is optionally substituted $C_{12-16}$ alkenyl. In some embodiments, $R^7$ is optionally substituted $C_{12-15}$ alkenyl. In some embodiments, $R^7$ is optionally substituted $C_{12-14}$ alkenyl. In some embodiments, $R^7$ is optionally substituted $C_{12-13}$ alkenyl.

In some embodiments, $R^7$ is optionally substituted $C_6$ alkenyl. In some embodiments, $R^7$ is optionally substituted $C_7$ alkenyl. In some embodiments, $R^7$ is optionally substituted $C_8$ alkenyl. In some embodiments, $R^7$ is optionally substituted $C_9$ alkenyl. In some embodiments, $R^7$ is optionally substituted $C_{10}$ alkenyl. In some embodiments, $R^7$ is optionally substituted $C_{11}$ alkenyl. In some embodiments, $R^7$ is optionally substituted $C_{12}$ alkenyl. In some embodiments, $R^7$ is optionally substituted $C_{13}$ alkenyl. In some embodiments, $R^7$ is optionally substituted $C_{14}$ alkenyl. In some embodiments, $R^7$ is optionally substituted $C_{15}$ alkenyl. In some embodiments, $R^7$ is optionally substituted $C_{16}$ alkenyl. In some embodiments, $R^7$ is optionally substituted $C_{17}$ alkenyl. In some embodiments, $R^7$ is optionally substituted $C_{18}$ alkenyl. In some embodiments, $R^7$ is optionally substituted $C_{19}$ alkenyl. In some embodiments, $R^7$ is optionally substituted $C_{20}$ alkenyl.

In some embodiments, for example, in any of the above embodiments, $R^7$ is a substituted alkenyl group. In some embodiments, $R^7$ is an unsubstituted alkenyl group. In some embodiments, $R^7$ is an optionally substituted straight-chain alkenyl group. In some embodiments, $R^7$ is a substituted straight-chain alkenyl group. In some embodiments, $R^7$ is an unsubstituted straight-chain alkenyl group. In some embodiments, $R^7$ is an optionally substituted branched alkenyl group. In some embodiments, $R^7$ is a substituted branched alkenyl group. In some embodiments, $R^7$ is an unsubstituted branched alkenyl group.

In some embodiments, $R^7$ is optionally substituted alkynyl. In some embodiments, $R^7$ is optionally substituted $C_{2-50}$ alkynyl. In some embodiments, $R^7$ is optionally substituted $C_{2-40}$ alkynyl. In some embodiments, $R^7$ is optionally substituted $C_{2-30}$ alkynyl. In some embodiments, $R^7$ is optionally substituted $C_{2-20}$ alkynyl. In some embodiments, $R^7$ is optionally substituted $C_{2-19}$ alkynyl. In some embodiments, $R^7$ is optionally substituted $C_{2-18}$ alkynyl. In some embodiments, $R^7$ is optionally substituted $C_{2-17}$ alkynyl. In some embodiments, $R^7$ is optionally substituted $C_{2-16}$ alkynyl. In some embodiments, $R^7$ is optionally substituted $C_{2-15}$ alkynyl. In some embodiments, $R^7$ is optionally substituted $C_{2-14}$ alkynyl. In some embodiments, $R^7$ is optionally substituted $C_{2-13}$ alkynyl. In some embodiments, $R^7$ is optionally substituted $C_{2-12}$ alkynyl. In some embodiments, $R^7$ is optionally substituted $C_{2-11}$ alkynyl. In some embodiments, $R^7$ is optionally substituted $C_{2-10}$ alkynyl. In some embodiments, $R^7$ is optionally substituted $C_{2-9}$ alkynyl. In some embodiments, $R^7$ is optionally substituted $C_{2-8}$ alkynyl. In some embodiments, $R^7$ is optionally substituted $C_{2-7}$ alkynyl. In some embodiments, $R^7$ is optionally substituted $C_{2-6}$ alkynyl.

In some embodiments, $R^7$ is optionally substituted $C_{4-50}$ alkynyl. In some embodiments, $R^7$ is optionally substituted $C_{4-40}$ alkynyl. In some embodiments, $R^7$ is optionally substituted $C_{4-30}$ alkynyl. In some embodiments, $R^7$ is optionally substituted $C_{4-20}$ alkynyl. In some embodiments, $R^7$ is optionally substituted $C_{4-19}$ alkynyl. In some embodiments, $R^7$ is optionally substituted $C_{4-18}$ alkynyl. In some embodiments, $R^7$ is optionally substituted $C_{4-17}$ alkynyl. In some embodiments, $R^7$ is optionally substituted $C_{4-16}$ alkynyl. In some embodiments, $R^7$ is optionally substituted $C_{4-15}$ alkynyl. In some embodiments, $R^7$ is optionally substituted $C_{4-14}$ alkynyl. In some embodiments, $R^7$ is optionally substituted $C_{4-13}$ alkynyl. In some embodiments, $R^7$ is optionally substituted $C_{4-12}$ alkynyl. In some embodiments, $R^7$ is optionally substituted $C_{4-11}$ alkynyl. In some embodiments, $R^7$ is optionally substituted $C_{4-10}$ alkynyl. In some embodiments, $R^7$ is optionally substituted $C_{4-9}$ alkynyl. In some embodiments, $R^7$ is optionally substituted $C_{4-8}$ alkynyl. In some embodiments, $R^7$ is optionally substituted $C_{4-7}$ alkynyl. In some embodiments, $R^7$ is optionally substituted $C_{4-6}$ alkynyl.

In some embodiments, $R^7$ is optionally substituted $C_{6-50}$ alkynyl. In some embodiments, $R^7$ is optionally substituted $C_{6-40}$ alkynyl. In some embodiments, $R^7$ is optionally substituted $C_{6-30}$ alkynyl. In some embodiments, $R^7$ is optionally substituted $C_{6-20}$ alkynyl. In some embodiments, $R^7$ is optionally substituted $C_{6-19}$ alkynyl. In some embodiments, $R^7$ is optionally substituted $C_{6-18}$ alkynyl. In some embodiments, $R^7$ is optionally substituted $C_{6-17}$ alkynyl. In some embodiments, $R^7$ is optionally substituted $C_{6-16}$ alkynyl. In some embodiments, $R^7$ is optionally substituted $C_{6-15}$ alkynyl. In some embodiments, $R^7$ is optionally substituted $C_{6-14}$ alkynyl. In some embodiments, $R^7$ is optionally substituted $C_{6-13}$ alkynyl. In some embodiments, $R^7$ is optionally substituted $C_{6-12}$ alkynyl. In some embodiments, $R^7$ is optionally substituted $C_{6-11}$ alkynyl. In some embodiments, $R^7$ is optionally substituted $C_{6-10}$ alkynyl. In some embodiments, $R^7$ is optionally substituted $C_{6-9}$ alkynyl. In some embodiments, $R^7$ is optionally substituted $C_{6-8}$ alkynyl. In some embodiments, $R^7$ is optionally substituted $C_{6-7}$ alkynyl.

In some embodiments, $R^7$ is optionally substituted $C_{8-50}$ alkynyl. In some embodiments, $R^7$ is optionally substituted $C_{8-40}$ alkynyl. In some embodiments, $R^7$ is optionally substituted $C_{8-30}$ alkynyl. In some embodiments, $R^7$ is optionally substituted $C_{8-20}$ alkynyl. In some embodiments, $R^7$ is optionally substituted $C_{8-19}$ alkynyl. In some embodiments, $R^7$ is optionally substituted $C_{8-18}$ alkynyl. In some embodiments, $R^7$ is optionally substituted $C_{8-17}$ alkynyl. In some embodiments, $R^7$ is optionally substituted $C_{8-16}$ alkynyl. In some embodiments, $R^7$ is optionally substituted $C_{8-15}$ alkynyl. In some embodiments, $R^7$ is optionally substituted $C_{8-14}$ alkynyl. In some embodiments, $R^7$ is optionally substituted $C_{8-13}$ alkynyl. In some embodiments, $R^7$ is optionally substituted $C_{8-12}$ alkynyl. In some embodiments, $R^7$ is optionally substituted $C_{8-11}$ alkynyl. In some embodiments, $R^7$ is optionally substituted $C_{8-10}$ alkynyl. In some embodiments, $R^7$ is optionally substituted $C_{8-9}$ alkynyl.

In some embodiments, $R^7$ is optionally substituted $C_{9-50}$ alkynyl. In some embodiments, $R^7$ is optionally substituted $C_{9-40}$ alkynyl. In some embodiments, $R^7$ is optionally substituted $C_{9-30}$ alkynyl. In some embodiments, $R^7$ is optionally substituted $C_{9-20}$ alkynyl. In some embodiments, $R^7$ is optionally substituted $C_{9-19}$ alkynyl. In some embodiments, $R^7$ is optionally substituted $C_{9-18}$ alkynyl. In some embodiments, $R^7$ is optionally substituted $C_{9-17}$ alkynyl. In some embodiments, $R^7$ is optionally substituted $C_{9-16}$ alkynyl. In some embodiments, $R^7$ is optionally substituted $C_{9-15}$ alkynyl. In some embodiments, $R^7$ is optionally substituted $C_{9-14}$ alkynyl. In some embodiments, $R^7$ is optionally substituted $C_{9-13}$ alkynyl. In some embodiments, $R^7$ is optionally substituted $C_{9-12}$ alkynyl. In some embodiments, $R^7$ is optionally substituted $C_{9-11}$ alkynyl. In some embodiments, $R^7$ is optionally substituted $C_{9-10}$ alkynyl.

In some embodiments, $R^7$ is optionally substituted $C_{10-50}$ alkynyl. In some embodiments, $R^7$ is optionally substituted $C_{10-40}$ alkynyl. In some embodiments, $R^7$ is optionally substituted $C_{10-30}$ alkynyl. In some embodiments, $R^7$ is optionally substituted $C_{10-20}$ alkynyl. In some embodiments, $R^7$ is optionally substituted $C_{10-19}$ alkynyl. In some embodiments, $R^7$ is optionally substituted $C_{10-18}$ alkynyl. In some embodiments, $R^7$ is optionally substituted $C_{10-17}$ alkynyl. In some embodiments, $R^7$ is optionally substituted $C_{10-16}$ alkynyl. In some embodiments, $R^7$ is optionally substituted $C_{10-15}$ alkynyl. In some embodiments, $R^7$ is optionally substituted $C_{10-14}$ alkynyl. In some embodiments, $R^7$ is optionally substituted $C_{10-13}$ alkynyl. In some embodiments, $R^7$ is optionally substituted $C_{10-12}$ alkynyl. In some embodiments, $R^7$ is optionally substituted $C_{10-11}$ alkynyl.

In some embodiments, $R^7$ is optionally substituted $C_{11-50}$ alkynyl. In some embodiments, $R^7$ is optionally substituted $C_{11-40}$ alkynyl. In some embodiments, $R^7$ is optionally substituted $C_{11-30}$ alkynyl. In some embodiments, $R^7$ is optionally substituted $C_{11-20}$ alkynyl. In some embodiments, $R^7$ is optionally substituted $C_{11-19}$ alkynyl. In some embodiments, $R^7$ is optionally substituted $C_{11-18}$ alkynyl. In some embodiments, $R^7$ is optionally substituted $C_{1-17}$ alkynyl. In some embodiments, $R^7$ is optionally substituted $C_{11-16}$ alkynyl. In some embodiments, $R^7$ is optionally substituted $C_{11-15}$ alkynyl. In some embodiments, $R^7$ is optionally substituted $C_{11-14}$ alkynyl. In some embodiments, $R^7$ is optionally substituted $C_{11-13}$ alkynyl. In some embodiments, $R^7$ is optionally substituted $C_{11-12}$ alkynyl.

In some embodiments, $R^7$ is optionally substituted $C_{12-50}$ alkynyl. In some embodiments, $R^7$ is optionally substituted $C_{12-40}$ alkynyl. In some embodiments, $R^7$ is optionally substituted $C_{12-30}$ alkynyl. In some embodiments, $R^7$ is optionally substituted $C_{12-20}$ alkynyl. In some embodiments, $R^7$ is optionally substituted $C_{12-19}$ alkynyl. In some embodiments, $R^7$ is optionally substituted $C_{12-18}$ alkynyl. In some embodiments, $R^7$ is optionally substituted $C_{12-17}$ alkynyl. In some embodiments, $R^7$ is optionally substituted $C_{12-16}$ alkynyl. In some embodiments, $R^7$ is optionally substituted $C_{12-15}$ alkynyl. In some embodiments, $R^7$ is optionally substituted $C_{12-14}$ alkynyl. In some embodiments, $R^7$ is optionally substituted $C_{12-13}$ alkynyl.

In some embodiments, $R^7$ is optionally substituted $C_6$ alkynyl. In some embodiments, $R^7$ is optionally substituted $C_7$ alkynyl. In some embodiments, $R^7$ is optionally substituted $C_8$ alkynyl. In some embodiments, $R^7$ is optionally substituted $C_9$ alkynyl. In some embodiments, $R^7$ is optionally substituted $C_{10}$ alkynyl. In some embodiments, $R^7$ is optionally substituted $C_{11}$ alkynyl. In some embodiments, $R^7$ is optionally substituted $C_{12}$ alkynyl. In some embodiments, $R^7$ is optionally substituted $C_{13}$ alkynyl. In some embodiments, $R^7$ is optionally substituted $C_{14}$ alkynyl. In some embodiments, $R^7$ is optionally substituted $C_{15}$ alkynyl. In some embodiments, $R^7$ is optionally substituted $C_{16}$ alkynyl. In some embodiments, $R^7$ is optionally substituted $C_{17}$ alkynyl. In some embodiments, $R^7$ is optionally substituted $C_{18}$ alkynyl. In some embodiments, $R^7$ is optionally substituted $C_{19}$ alkynyl. In some embodiments, $R^7$ is optionally substituted $C_{20}$ alkynyl.

In some embodiments, for example, in any of the above embodiments, $R^7$ is a substituted alkynyl group. In some embodiments, $R^7$ is an unsubstituted alkynyl group. In some embodiments, $R^7$ is an optionally substituted straight-chain alkynyl group. In some embodiments, $R^7$ is a substituted straight-chain alkynyl group. In some embodiments, $R^7$ is an unsubstituted straight-chain alkynyl group. In some embodiments, $R^7$ is an optionally substituted branched alkynyl group. In some embodiments, $R^7$ is a substituted branched alkynyl group. In some embodiments, $R^7$ is an unsubstituted branched alkynyl group.

In some embodiments, $R^7$ is optionally substituted carbocyclyl. In some embodiments, $R^7$ is optionally substituted heterocyclyl. In some embodiments, $R^7$ is optionally substituted aryl. In some embodiments, $R^7$ is optionally substituted heteroaryl. In some embodiments, $R^7$ is a nitrogen protecting group.

In some embodiments, $R^7$ is a group of formula (i). In some embodiments, $R^7$ is a group of formula (i-a). In some embodiments, $R^7$ is a group of formula

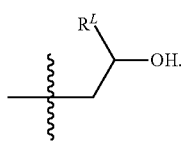

(i-a1)

In some embodiments, $R^7$ is a group of formula (i-b). In some embodiments, $R^7$ is a group of formula (ii). In some embodiments, $R^7$ is a group of formula (iii).

In some embodiments, at least one instance of $R^6$ and $R^7$ is a group of the formula (i), (ii) or (iii). In some embodiments, each instance of $R^6$ and $R^7$ is independently a group of the formula (i), (ii) or (iii). In some embodiments, each instance of $R^6$ and $R^7$ is independently a group of the formula (i). In some embodiments, each instance of $R^6$ and $R^7$ is independently a group of the formula (i-a). In some embodiments, each instance of $R^6$ and $R^7$ is independently a group of the formula (i-b). In some embodiments, each instance of $R^6$ and $R^7$ is independently a group of the formula (ii). In some embodiments, each instance of $R^6$ and $R^7$ is independently a group of the formula (iii).

In some embodiments, $R^6$ and $R^7$ are the same. In some embodiments, $R^6$ and $R^7$ are different.

In certain embodiments, both $R^6$ and $R^7$ are hydrogen. In certain embodiments, $R^6$ is hydrogen and $R^7$ is a group of the formula (i), (ii), or (iii). In certain embodiments, $R^6$ is hydrogen and $R^7$ is a group of the formula (i). In certain embodiments, $R^6$ is hydrogen and $R^7$ is a group of the formula (ii). In certain embodiments, $R^6$ is hydrogen and $R^7$ is a group of the formula (iii). In certain embodiments, each of $R^6$ and $R^7$ is independently a group of the formula (i), (ii), or (iii). In certain embodiments, each of $R^6$ and $R^7$ is independently a group of the formula (i). In certain embodiments, each of $R^6$ and $R^7$ is independently a group of the formula (ii). In certain embodiments, each of $R^6$ and $R^7$ is independently a group of the formula (iii). In certain embodiments, $R^6$ and $R^7$ are the same group, which is selected from formulas (i), (ii), and (iii). In some embodiments, $R^6$ and $R^7$ are the same group of formula (i). In some embodiments, $R^6$ and $R^7$ are the same group of formula (i-a). In some embodiments, $R^6$ and $R^7$ are the same group of formula (i-a1). In some embodiments, $R^6$ and $R^7$ are the same group of formula (i-b).

In some embodiments, $R^6$ and $R^7$ are the same group of formula

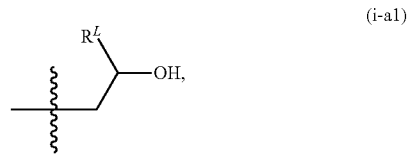

(i-a1)

wherein $R^L$ is as defined above and described herein. In some embodiments, $R^6$ and $R^7$ are the same group of formula

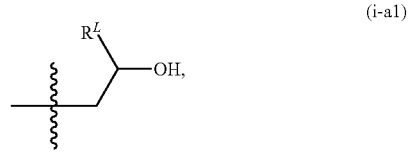

(i-a1)

wherein $R^L$ is optionally substituted $C_{1-50}$alkyl, optionally substituted $C_{2-50}$alkenyl, optionally substituted $C_{2-50}$alkynyl, optionally substituted heteroC$_{1-50}$alkyl, optionally substituted heteroC$_{2-50}$alkenyl, or optionally substituted heteroC$_{2-50}$alkynyl. In some embodiments, $R^6$ and $R^7$ are the same group of formula

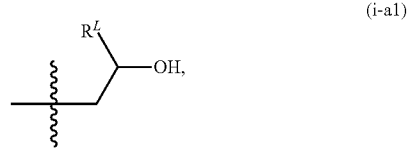

(i-a1)

wherein $R^L$ is optionally substituted $C_{5-50}$alkyl, optionally substituted $C_{5-50}$alkenyl, optionally substituted $C_{5-50}$alkynyl, optionally substituted heteroC$_{5-50}$alkyl, optionally substituted heteroC$_{5-50}$alkenyl, or optionally substituted heteroC$_{5-50}$alkynyl. In some embodiments, $R^6$ and $R^7$ are the same group of formula

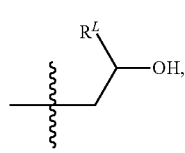

(i-a1)

wherein $R^L$ is optionally substituted $C_{5-40}$alkyl, optionally substituted $C_{5-40}$alkenyl, optionally substituted $C_{5-40}$alkynyl, optionally substituted heteroC$_{5-40}$alkyl, optionally substituted heteroC$_{5-40}$alkenyl, or optionally substituted heteroC$_{5-40}$alkynyl. In some embodiments, $R^6$ and $R^7$ are the same group of formula

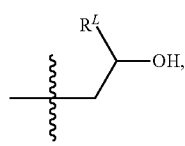

(i-a1)

wherein $R^L$ is optionally substituted $C_{5-30}$alkyl, optionally substituted $C_{5-30}$alkenyl, optionally substituted $C_{5-30}$alkynyl, optionally substituted heteroC$_{5-30}$alkyl, optionally substituted heteroC$_{5-30}$alkenyl, or optionally substituted heteroC$_{5-30}$alkynyl. In some embodiments, $R^6$ and $R^7$ are the same group of formula

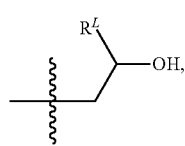

(i-a1)

wherein $R^L$ is optionally substituted $C_{5-25}$alkyl, optionally substituted $C_{5-25}$alkenyl, optionally substituted $C_{5-25}$alkynyl, optionally substituted heteroC$_{5-25}$alkyl, optionally substituted heteroC$_{5-25}$alkenyl, or optionally substituted heteroC$_{5-25}$alkynyl. In some embodiments, $R^6$ and $R^7$ are the same group of formula

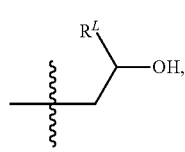

(i-a1)

wherein $R^L$ is optionally substituted $C_{5-20}$alkyl, optionally substituted $C_{5-20}$alkenyl, optionally substituted $C_{5-20}$alkynyl, optionally substituted heteroC$_{5-20}$alkyl, optionally substituted heteroC$_{5-20}$alkenyl, or optionally substituted heteroC$_{5-20}$alkynyl. In some embodiments, $R^6$ and $R^7$ are the same group of formula

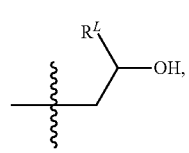

(i-a1)

wherein $R^L$ is optionally substituted $C_{5-15}$alkyl, optionally substituted $C_{5-15}$alkenyl, optionally substituted $C_{5-15}$alkynyl, optionally substituted heteroC$_{5-15}$alkyl, optionally substituted heteroC$_{5-15}$alkenyl, or optionally substituted heteroC$_{5-15}$alkynyl. In some embodiments, $R^6$ and $R^7$ are the same group of formula

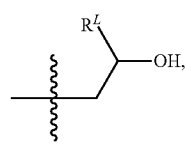

(i-a1)

wherein $R^L$ is optionally substituted $C_5$ alkyl, optionally substituted $C_5$ alkenyl, optionally substituted $C_5$ alkynyl, optionally substituted heteroC$_5$alkyl, optionally substituted heteroC$_5$alkenyl, or optionally substituted heteroC$_5$alkynyl. In some embodiments, $R^6$ and $R^7$ are the same group of formula

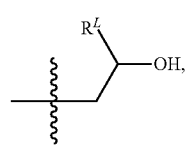

(i-a1)

wherein $R^L$ is optionally substituted $C_6$ alkyl, optionally substituted $C_6$ alkenyl, optionally substituted $C_6$ alkynyl, optionally substituted heteroC$_6$alkyl, optionally substituted heteroC$_6$alkenyl, or optionally substituted heteroC$_6$alkynyl. In some embodiments, $R^6$ and $R^7$ are the same group of formula

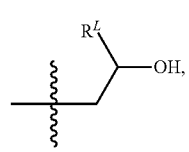

(i-a1)

wherein $R^L$ is optionally substituted $C_7$ alkyl, optionally substituted $C_7$ alkenyl, optionally substituted $C_7$ alkynyl, optionally substituted heteroC$_7$alkyl, optionally substituted heteroC$_7$alkenyl, or optionally substituted heteroC$_7$alkynyl. In some embodiments, $R^6$ and $R^7$ are the same group of formula

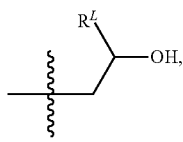
(i-a1)

wherein $R^L$ is optionally substituted $C_8$ alkyl, optionally substituted $C_8$ alkenyl, optionally substituted $C_8$ alkynyl, optionally substituted heteroC$_8$alkyl, optionally substituted heteroC$_8$alkenyl, or optionally substituted heteroC$_8$alkynyl. In some embodiments, $R^6$ and $R^7$ are the same group of formula

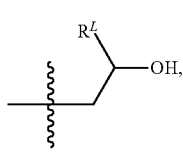
(i-a1)

wherein $R^L$ is optionally substituted $C_9$ alkyl, optionally substituted $C_9$ alkenyl, optionally substituted $C_9$ alkynyl, optionally substituted heteroC$_9$alkyl, optionally substituted heteroC$_9$alkenyl, or optionally substituted heteroC$_9$alkynyl. In some embodiments, $R^6$ and $R^7$ are the same group of formula

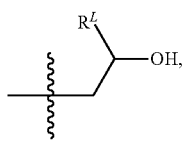
(i-a1)

wherein $R^L$ is optionally substituted $C_{10}$ alkyl, optionally substituted $C_{10}$ alkenyl, optionally substituted $C_{10}$ alkynyl, optionally substituted heteroC$_{10}$alkyl, optionally substituted heteroC$_{10}$alkenyl, or optionally substituted heteroC$_{10}$ alkynyl. In some embodiments, $R^6$ and $R^7$ are the same group of formula

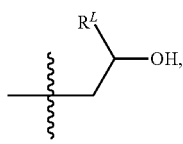
(i-a1)

wherein $R^L$ is optionally substituted $C_{11}$ alkyl, optionally substituted $C_{11}$ alkenyl, optionally substituted $C_{11}$ alkynyl, optionally substituted heteroC$_{11}$alkyl, optionally substituted heteroC$_{11}$alkenyl, or optionally substituted heteroC$_{11}$ alkynyl. In some embodiments, $R^6$ and $R^7$ are the same group of formula

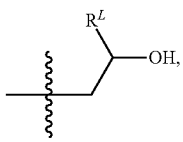
(i-a1)

wherein $R^L$ is optionally substituted $C_{12}$ alkyl, optionally substituted $C_{12}$ alkenyl, optionally substituted $C_{12}$ alkynyl, optionally substituted heteroC$_{12}$alkyl, optionally substituted heteroC$_{12}$alkenyl, or optionally substituted heteroC$_{12}$ alkynyl. In some embodiments, $R^6$ and $R^7$ are the same group of formula

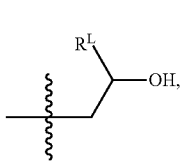
(i-a1)

wherein $R^L$ is optionally substituted $C_{13}$ alkyl, optionally substituted $C_{13}$ alkenyl, optionally substituted $C_{13}$ alkynyl, optionally substituted heteroC$_{13}$alkyl, optionally substituted heteroC$_{13}$alkenyl, or optionally substituted heteroC$_{13}$ alkynyl. In some embodiments, $R^6$ and $R^7$ are the same group of formula

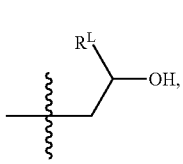
(i-a1)

wherein $R^L$ is optionally substituted $C_{14}$ alkyl, optionally substituted $C_{14}$ alkenyl, optionally substituted $C_{14}$ alkynyl, optionally substituted heteroC$_{14}$alkyl, optionally substituted heteroC$_{14}$alkenyl, or optionally substituted heteroC$_{14}$ alkynyl. In some embodiments, $R^6$ and $R^7$ are the same group of formula

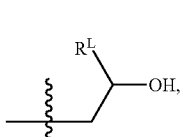
(i-a1)

wherein $R^L$ is optionally substituted $C_{15}$ alkyl, optionally substituted $C_{15}$ alkenyl, optionally substituted $C_{15}$ alkynyl, optionally substituted heteroC$_{15}$alkyl, optionally substituted heteroC$_{15}$alkenyl, or optionally substituted heteroC$_{15}$ alkynyl.

In some embodiments, $R^6$ and $R^7$ are the same group of formula

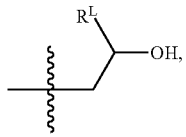
(i-a1)

wherein $R^L$ is as defined above and described herein. In some embodiments, $R^6$ and $R^7$ are the same group of formula

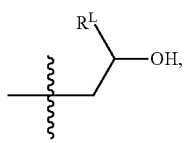
(i-a1)

wherein R is optionally substituted $C_{1-50}$alkyl. In some embodiments, $R^6$ and $R^7$ are the same group of formula

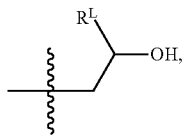
(i-a1)

wherein $R^L$ is optionally substituted $C_{5-50}$alkyl. In some embodiments, $R^6$ and $R^7$ are the same group of formula

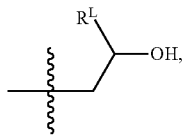
(i-a1)

wherein R is optionally substituted $C_{5-40}$alkyl. In some embodiments, $R^6$ and $R^7$ are the same group of formula

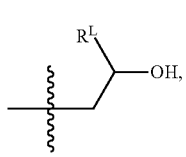
(i-a1)

wherein $R^L$ is optionally substituted $C_{5-30}$alkyl. In some embodiments, $R^6$ and $R^7$ are the same group of formula

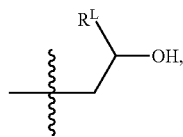
(i-a1)

wherein $R^L$ is optionally substituted $C_{5-25}$alkyl. In some embodiments, $R^6$ and $R^7$ are the same group of formula

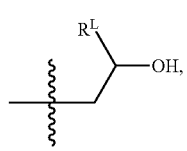
(i-a1)

wherein $R^L$ is optionally substituted $C_{5-20}$alkyl. In some embodiments, $R^6$ and $R^7$ are the same group of formula

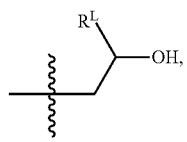
(i-a1)

wherein $R^L$ is optionally substituted $C_{5-15}$alkyl. In some embodiments, $R^6$ and $R^7$ are the same group of formula

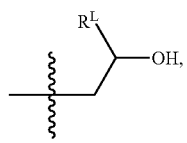
(i-a1)

wherein $R^L$ is optionally substituted $C_5$ alkyl. In some embodiments, $R^6$ and $R^7$ are the same group of formula (i-a1)

wherein $R^L$ is optionally substituted $C_6$ alkyl. In some embodiments, $R^6$ and $R^7$ are the same group of formula

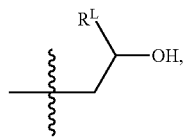
(i-a1)

wherein $R^L$ is optionally substituted $C_7$ alkyl. In some embodiments, $R^6$ and $R^7$ are the same group of formula

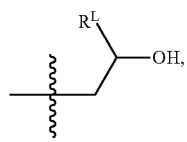
(i-a1)

wherein $R^L$ is optionally substituted $C_8$ alkyl. In some embodiments, $R^6$ and $R^7$ are the same group of formula

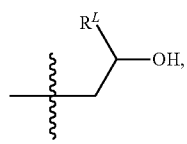
(i-a1)

wherein $R^L$ is optionally substituted $C_9$ alkyl. In some embodiments, $R^6$ and $R^7$ are the same group of formula

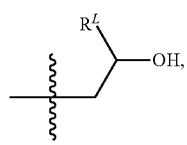
(i-a1)

wherein $R^L$ is optionally substituted $C_{10}$ alkyl. In some embodiments, $R^6$ and $R^7$ are the same group of formula

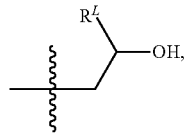
(i-a1)

wherein $R^L$ is optionally substituted $C_{11}$ alkyl. In some embodiments, $R^6$ and $R^7$ are the same group of formula

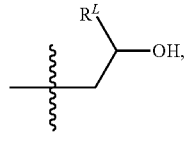
(i-a1)

wherein $R^L$ is optionally substituted $C_{12}$ alkyl. In some embodiments, $R^6$ and $R^7$ are the same group of formula

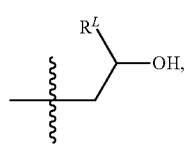
(i-a1)

wherein $R^L$ is optionally substituted $C_{13}$ alkyl. In some embodiments, $R^6$ and $R^7$ are the same group of formula

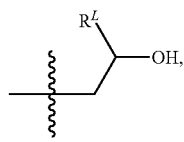
(i-a1)

wherein $R^L$ is optionally substituted $C_{14}$ alkyl. In some embodiments, $R^6$ and $R^7$ are the same group of formula

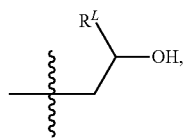
(i-a1)

wherein $R^L$ is optionally substituted $C_{15}$ alkyl.

As generally defined above, each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{41}$ groups, together with the nitrogen atom to which they are attached, are joined to form an optionally substituted heterocyclic or optionally substituted heteroaryl ring.

In some embodiments, $R^{41}$ is hydrogen. In some embodiments, $R^{41}$ is optionally substituted alkyl. In some embodiments, $R^{41}$ is optionally substituted alkenyl. In some embodiments, $R^{41}$ is optionally substituted alkynyl. In some embodiments, $R^{41}$ is optionally substituted carbocyclyl. In some embodiments, $R^{41}$ is optionally substituted heterocyclyl. In some embodiments, $R^{41}$ is optionally substituted aryl. In some embodiments, $R^{41}$ is optionally substituted heteroaryl. In some embodiments, $R^{41}$ is an oxygen protecting group when attached to an oxygen atom. In some embodiments, $R^{41}$ is a sulfur protecting group when attached to a sulfur atom. In some embodiments, $R^{41}$ is a nitrogen protecting group when attached to a nitrogen atom. In some embodiments, two $R^{41}$ groups, together with the nitrogen atom to which they are attached, are joined to form an optionally substituted heterocyclic or optionally substituted heteroaryl ring.

As generally defined above, each instance of R' is independently hydrogen or optionally substituted alkyl. In some embodiments, R' is hydrogen. In some embodiments, R' is substituted alkyl. In certain embodiments, at least one instance of R' is hydrogen. In certain embodiments, at least two instances of R' is hydrogen. In certain embodiments, each instance of R' is hydrogen. In certain embodiments, at least one instance of R' is optionally substituted alkyl, e.g., methyl. In certain embodiments, at least two instances of R' is optionally substituted alkyl, e.g., methyl. In some embodiments, at least one instance of R' is hydrogen, and at least one instance of R' is optionally substituted alkyl. In certain embodiments, one instance of R' is optionally substituted alkyl, and the rest are hydrogen.

As generally defined above, X is O, S, or $NR^X$. In some embodiments, X is O. In some embodiments, X is S. In some embodiments, X is $NR^X$, wherein $R^X$ is as defined above and described herein.

As generally defined above, $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In some embodiments, $R^X$ is hydrogen. In some embodiments, $R^X$ is optionally substituted alkyl. In some embodiments, $R^X$ is optionally substituted alkenyl. In some embodiments, $R^X$ is optionally substituted alkynyl. In some embodiments, $R^X$ is optionally substituted carbocyclyl. In some embodiments, $R^X$ is optionally substituted heterocyclyl. In some embodiments, $R^X$ is optionally substituted aryl. In some embodiments, $R^X$ is optionally substituted heteroaryl. In some embodiments, $R^X$ is a nitrogen protecting group.

As generally defined above, Y is O, S, or $NR^Y$. In some embodiments, Y is O. In some embodiments, Y is S. In some embodiments, Y is $NR^Y$, wherein $R^Y$ is as defined above and described herein.

As generally defined above, $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In some embodiments, $R^Y$ is hydrogen. In some embodiments, $R^Y$ is optionally substituted alkyl. In some embodiments, $R^Y$ is optionally substituted alkenyl. In some embodiments, $R^Y$ is optionally substituted alkynyl. In some embodiments, $R^Y$ is optionally substituted carbocyclyl. In some embodiments, $R^Y$ is optionally substituted heterocyclyl. In some embodiments, $R^Y$ is optionally substituted aryl. In some embodiments, $R^Y$ is optionally substituted heteroaryl. In some embodiments, R is a nitrogen protecting group.

As generally defined above, $R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom. In some embodiments, $R^P$ is hydrogen. In some embodiments, $R^P$ is optionally substituted alkyl. In some embodiments, $R^P$ is optionally substituted alkenyl. In some embodiments, $R^P$ is optionally substituted alkynyl. In some embodiments, $R^P$ is optionally substituted carbocyclyl. In some embodiments, $R^P$ is optionally substituted heterocyclyl. In some embodiments, $R^P$ is optionally substituted aryl. In some embodiments, $R^P$ is optionally substituted heteroaryl. In some embodiments, $R^P$ is an oxygen protecting group when attached to an oxygen atom. In some embodiments, $R^P$ is a sulfur protecting group when attached to a sulfur atom. In some embodiments, $R^P$ is a nitrogen protecting group when attached to a nitrogen atom.

As generally defined above, $R^L$ is optionally substituted $C_{1-50}$ alkyl, optionally substituted $C_{2-50}$ alkenyl, optionally substituted $C_{2-50}$ alkynyl, optionally substituted hetero$C_{1-50}$ alkyl, optionally substituted hetero$C_{2-50}$ alkenyl, optionally substituted hetero$C_{2-50}$ alkynyl, or a polymer.

In some embodiments, $R^L$ is optionally substituted $C_{1-50}$ alkyl. In some embodiments, $R^L$ is optionally substituted $C_{2-50}$ alkyl. In some embodiments, $R^L$ is optionally substituted $C_{2-40}$ alkyl. In some embodiments, $R^L$ is optionally substituted $C_{2-30}$ alkyl. In some embodiments, $R^L$ is optionally substituted $C_{2-20}$ alkyl. In some embodiments, $R^L$ is optionally substituted $C_{2-19}$ alkyl. In some embodiments, $R^L$ is optionally substituted $C_{2-18}$ alkyl. In some embodiments, $R^L$ is optionally substituted $C_{2-17}$ alkyl. In some embodiments, $R^L$ is optionally substituted $C_{2-16}$ alkyl. In some embodiments, $R^L$ is optionally substituted $C_{2-15}$ alkyl. In some embodiments, $R^L$ is optionally substituted $C_{2-14}$ alkyl. In some embodiments, $R^L$ is optionally substituted $C_{2-13}$ alkyl. In some embodiments, $R^L$ is optionally substituted $C_{2-12}$ alkyl. In some embodiments, $R^L$ is optionally substituted $C_{2-11}$ alkyl. In some embodiments, $R^L$ is optionally substituted $C_{2-10}$ alkyl. In some embodiments, $R^L$ is optionally substituted $C_{2-9}$ alkyl. In some embodiments, $R^L$ is optionally substituted $C_{2-8}$ alkyl. In some embodiments, $R^L$ is optionally substituted $C_{2-7}$ alkyl. In some embodiments, $R^L$ is optionally substituted $C_{2-6}$ alkyl.

In some embodiments, $R^L$ is optionally substituted $C_{4-50}$ alkyl. In some embodiments, $R^L$ is optionally substituted $C_{4-40}$ alkyl. In some embodiments, $R^L$ is optionally substituted $C_{4-30}$ alkyl. In some embodiments, $R^L$ is optionally substituted $C_{4-20}$ alkyl. In some embodiments, $R^L$ is optionally substituted $C_{4-19}$ alkyl. In some embodiments, $R^L$ is optionally substituted $C_{4-18}$ alkyl. In some embodiments, $R^L$ is optionally substituted $C_{4-17}$ alkyl. In some embodiments, $R^L$ is optionally substituted $C_{4-16}$ alkyl. In some embodiments, $R^L$ is optionally substituted $C_{4-15}$ alkyl. In some embodiments, $R^L$ is optionally substituted $C_{4-14}$ alkyl. In some embodiments, $R^L$ is optionally substituted $C_{4-13}$ alkyl. In some embodiments, $R^L$ is optionally substituted $C_{4-12}$ alkyl. In some embodiments, $R^L$ is optionally substituted $C_{4-11}$ alkyl. In some embodiments, $R^L$ is optionally substituted $C_{4-10}$ alkyl. In some embodiments, $R^L$ is optionally substituted $C_{4-9}$ alkyl. In some embodiments, $R^L$ is optionally substituted $C_{4-8}$ alkyl. In some embodiments, $R^L$ is optionally substituted $C_{4-7}$ alkyl. In some embodiments, $R^L$ is optionally substituted $C_{4-6}$ alkyl.

In some embodiments, $R^L$ is optionally substituted $C_{6-50}$ alkyl. In some embodiments, $R^L$ is optionally substituted $C_{6-40}$ alkyl. In some embodiments, $R^L$ is optionally substituted $C_{6-30}$ alkyl. In some embodiments, $R^L$ is optionally substituted $C_{6-20}$ alkyl. In some embodiments, $R^L$ is optionally substituted $C_{6-19}$ alkyl. In some embodiments, $R^L$ is optionally substituted $C_{6-18}$ alkyl. In some embodiments, $R^L$ is optionally substituted $C_{6-17}$ alkyl. In some embodiments, $R^L$ is optionally substituted $C_{6-16}$ alkyl. In some embodiments, $R^L$ is optionally substituted $C_{6-15}$ alkyl. In some embodiments, $R^L$ is optionally substituted $C_{6-14}$ alkyl. In some embodiments, $R^L$ is optionally substituted $C_{6-13}$ alkyl. In some embodiments, $R^L$ is optionally substituted $C_{6-12}$ alkyl. In some embodiments, $R^L$ is optionally substituted $C_{6-11}$ alkyl. In some embodiments, $R^L$ is optionally substituted $C_{6-10}$ alkyl. In some embodiments, $R^L$ is optionally substituted $C_{6-9}$ alkyl. In some embodiments, $R^L$ is optionally substituted $C_{6-8}$ alkyl. In some embodiments, $R^L$ is optionally substituted $C_{6-7}$ alkyl.

In some embodiments, $R^L$ is optionally substituted $C_{8-50}$ alkyl. In some embodiments, $R^L$ is optionally substituted $C_{8-40}$ alkyl. In some embodiments, $R^L$ is optionally substituted $C_{8-30}$ alkyl. In some embodiments, $R^L$ is optionally substituted $C_{8-20}$ alkyl. In some embodiments, $R^L$ is optionally substituted $C_{8-19}$ alkyl. In some embodiments, $R^L$ is optionally substituted $C_{8-18}$ alkyl. In some embodiments, $R^L$ is optionally substituted $C_{8-17}$ alkyl. In some embodiments, $R^L$ is optionally substituted $C_{8-16}$ alkyl. In some embodiments, $R^L$ is optionally substituted $C_{8-15}$ alkyl. In some embodiments, $R^L$ is optionally substituted $C_{8-14}$ alkyl. In some embodiments, $R^L$ is optionally substituted $C_{8-13}$ alkyl. In some embodiments, $R^L$ is optionally substituted $C_{8-12}$ alkyl. In some embodiments, $R^L$ is optionally substituted $C_{8-11}$ alkyl. In some embodiments, $R^L$ is optionally substituted $C_{8-10}$ alkyl. In some embodiments, $R^L$ is optionally substituted $C_{8-9}$ alkyl.

In some embodiments, $R^L$ is optionally substituted $C_{9-50}$ alkyl. In some embodiments, $R^L$ is optionally substituted $C_{9-40}$ alkyl. In some embodiments, $R^L$ is optionally substituted $C_{9-30}$ alkyl. In some embodiments, $R^L$ is optionally substituted $C_{9-20}$ alkyl. In some embodiments, $R^L$ is optionally substituted $C_{9-19}$ alkyl. In some embodiments, $R^L$ is optionally substituted $C_{9-18}$ alkyl. In some embodiments, $R^L$ is optionally substituted $C_{9-17}$ alkyl. In some embodiments, $R^L$ is optionally substituted $C_{9-16}$ alkyl. In some embodiments, $R^L$ is optionally substituted $C_{9-15}$ alkyl. In some embodiments, $R^L$ is optionally substituted $C_{9-14}$ alkyl. In some embodiments, $R^L$ is optionally substituted $C_{9-13}$ alkyl. In some embodiments, $R^L$ is optionally substituted $C_{9-12}$ alkyl. In some embodiments, $R^L$ is optionally substituted $C_{9-11}$ alkyl. In some embodiments, $R^L$ is optionally substituted $C_{9-10}$ alkyl.

In some embodiments, $R^L$ is optionally substituted $C_{10-50}$ alkyl. In some embodiments, $R^L$ is optionally substituted $C_{10-40}$ alkyl. In some embodiments, $R^L$ is optionally substituted $C_{10-30}$ alkyl. In some embodiments, $R^L$ is optionally substituted $C_{10-20}$ alkyl. In some embodiments, $R^L$ is optionally substituted $C_{10-19}$ alkyl. In some embodiments, $R^L$ is optionally substituted $C_{10-18}$ alkyl. In some embodiments, $R^L$ is optionally substituted $C_{10-17}$ alkyl. In some embodiments, $R^L$ is optionally substituted $C_{10-16}$ alkyl. In some embodiments, $R^L$ is optionally substituted $C_{10-15}$ alkyl. In some embodiments, $R^L$ is optionally substituted $C_{10-14}$ alkyl. In some embodiments, $R^L$ is optionally substituted $C_{10-13}$ alkyl. In some embodiments, $R^L$ is optionally substituted $C_{10-12}$ alkyl. In some embodiments, $R^L$ is optionally substituted $C_{10-11}$ alkyl.

In some embodiments, $R^L$ is optionally substituted $C_{11-50}$ alkyl. In some embodiments, $R^L$ is optionally substituted $C_{11-40}$ alkyl. In some embodiments, $R^L$ is optionally substituted $C_{11-30}$ alkyl. In some embodiments, $R^L$ is optionally substituted $C_{11-20}$ alkyl. In some embodiments, $R^L$ is optionally substituted $C_{11-19}$ alkyl. In some embodiments, $R^L$ is optionally substituted $C_{11-18}$ alkyl. In some embodiments, $R^L$ is optionally substituted $C_{11-17}$ alkyl. In some embodiments, $R^L$ is optionally substituted $C_{11-16}$ alkyl. In some embodiments, $R^L$ is optionally substituted $C_{11-15}$ alkyl. In some embodiments, $R^L$ is optionally substituted $C_{11-14}$ alkyl. In some embodiments, $R^L$ is optionally substituted $C_{11-13}$ alkyl. In some embodiments, $R^L$ is optionally substituted $C_{11-12}$ alkyl.

In some embodiments, $R^L$ is optionally substituted $C_{12-50}$ alkyl. In some embodiments, $R^L$ is optionally substituted $C_{12-40}$ alkyl. In some embodiments, $R^L$ is optionally substituted $C_{12-30}$ alkyl. In some embodiments, $R^L$ is optionally substituted $C_{12-20}$ alkyl. In some embodiments, $R^L$ is optionally substituted $C_{12-19}$ alkyl. In some embodiments, $R^L$ is optionally substituted $C_{12-18}$ alkyl. In some embodiments, $R^L$ is optionally substituted $C_{12-17}$ alkyl. In some embodiments, $R^L$ is optionally substituted $C_{12-16}$ alkyl. In some embodiments, $R^L$ is optionally substituted $C_{12-15}$ alkyl. In some embodiments, $R^L$ is optionally substituted $C_{12-14}$ alkyl. In some embodiments, $R^L$ is optionally substituted $C_{12-13}$ alkyl.

In some embodiments, $R^L$ is optionally substituted $C_6$ alkyl. In some embodiments, $R^L$ is optionally substituted $C_7$ alkyl. In some embodiments, $R^L$ is optionally substituted $C_8$ alkyl. In some embodiments, $R^L$ is optionally substituted $C_9$ alkyl. In some embodiments, $R^L$ is optionally substituted $C_{10}$ alkyl. In some embodiments, $R^L$ is optionally substituted $C_{11}$ alkyl. In some embodiments, $R^L$ is optionally substituted $C_{12}$ alkyl. In some embodiments, $R^L$ is optionally substituted $C_{13}$ alkyl. In some embodiments, $R^L$ is optionally substituted $C_{14}$ alkyl. In some embodiments, $R^L$ is optionally substituted $C_{15}$ alkyl. In some embodiments, $R^L$ is optionally substituted $C_{16}$ alkyl. In some embodiments, $R^L$ is optionally substituted $C_{17}$ alkyl. In some embodiments, $R^L$ is optionally substituted $C_{18}$ alkyl. In some embodiments, $R^L$ is optionally substituted $C_{19}$ alkyl. In some embodiments, $R^L$ is optionally substituted $C_{20}$ alkyl.

In some embodiments, for example, in any of the above embodiments, $R^L$ is a substituted alkyl group. In some embodiments, $R^L$ is an unsubstituted alkyl group. In some embodiments, $R^L$ is an optionally substituted straight-chain alkyl group. In some embodiments, $R^L$ is a substituted straight-chain alkyl group. In some embodiments, $R^L$ is an unsubstituted straight-chain alkyl group. In some embodiments, $R^L$ is an optionally substituted branched alkyl group. In some embodiments, $R^L$ is a substituted branched alkyl group. In some embodiments, $R^L$ is an unsubstituted branched alkyl group.

In certain embodiments, at least one instance of $R^L$ is an unsubstituted alkyl. Exemplary unsubstituted alkyl groups include, but are not limited to, $—CH_3$, $—C_2H_5$, $—C_3H_7$, $—C_4H_9$, $—C_5H_{11}$, $—C_6H_{13}$, $—C_7H_{15}$, $—C_8H_{17}$, $—C_9H_{19}$, $—C_{10}H_{21}$, $—C_{11}H_{23}$, $—C_{12}H_{25}$, $—C_{13}H_{27}$, $—C_{14}H_{29}$, $—C_{15}H_{31}$, $—C_{16}H_{33}$, $—C_{17}H_{35}$, $—C_{18}H_{37}$, $—C_{19}H_{39}$, $—C_{20}H_{41}$, $—C_{21}H_{43}$, $—C_{22}H_{45}$, $—C_{23}H_{47}$, $—C_{24}H_{49}$, and $—C_{25}H_{51}$.

In certain embodiments, at least one instance of $R^L$ is a substituted alkyl. For example, in certain embodiments, at least one instance of $R^L$ is an alkyl substituted with one or more fluorine substituents. Exemplary fluorinated alkyl groups include, but are not limited to:

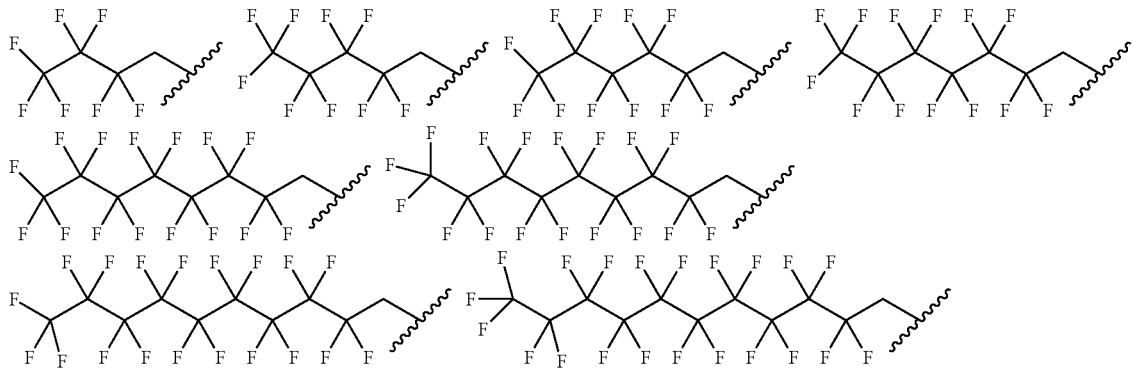

-continued

[chemical structures]

In some embodiments, $R^L$ is optionally substituted $C_{2-50}$ alkenyl. In some embodiments, $R^L$ is optionally substituted $C_{2-40}$ alkenyl. In some embodiments, $R^L$ is optionally substituted $C_{2-30}$ alkenyl. In some embodiments, $R^L$ is optionally substituted $C_{2-20}$ alkenyl. In some embodiments, $R^L$ is optionally substituted $C_{2-19}$ alkenyl. In some embodiments, $R^L$ is optionally substituted $C_{2-18}$ alkenyl. In some embodiments, $R^L$ is optionally substituted $C_{2-17}$ alkenyl. In some embodiments, $R^L$ is optionally substituted $C_{2-16}$ alkenyl. In some embodiments, $R^L$ is optionally substituted $C_{2-15}$ alkenyl. In some embodiments, $R^L$ is optionally substituted $C_{2-14}$ alkenyl. In some embodiments, $R^L$ is optionally substituted $C_{2-13}$ alkenyl. In some embodiments, $R^L$ is optionally substituted $C_{2-12}$ alkenyl. In some embodiments, $R^L$ is optionally substituted $C_{2-11}$ alkenyl. In some embodiments, $R^L$ is optionally substituted $C_{2-10}$ alkenyl. In some embodiments, $R^L$ is optionally substituted $C_{2-9}$ alkenyl. In some embodiments, $R^L$ is optionally substituted $C_{2-8}$ alkenyl. In some embodiments, $R^L$ is optionally substituted $C_{2-7}$ alkenyl. In some embodiments, $R^L$ is optionally substituted $C_{2-6}$ alkenyl.

In some embodiments, $R^L$ is optionally substituted $C_{4-50}$ alkenyl. In some embodiments, $R^L$ is optionally substituted $C_{4-40}$ alkenyl. In some embodiments, $R^L$ is optionally substituted $C_{4-30}$ alkenyl. In some embodiments, $R^L$ is optionally substituted $C_{4-20}$ alkenyl. In some embodiments, $R^L$ is optionally substituted $C_{4-19}$ alkenyl. In some embodiments, $R^L$ is optionally substituted $C_{4-18}$ alkenyl. In some embodiments, $R^L$ is optionally substituted $C_{4-17}$ alkenyl. In some embodiments, $R^L$ is optionally substituted $C_{4-16}$ alkenyl. In some embodiments, $R^L$ is optionally substituted $C_{4-15}$ alkenyl. In some embodiments, $R^L$ is optionally substituted $C_{4-14}$ alkenyl. In some embodiments, $R^L$ is optionally substituted $C_{4-13}$ alkenyl. In some embodiments, $R^L$ is optionally substituted $C_{4-12}$ alkenyl. In some embodiments, $R^L$ is optionally substituted $C_{4-11}$ alkenyl. In some embodiments, $R^L$ is optionally substituted $C_{4-10}$ alkenyl. In some embodiments, $R^L$ is optionally substituted $C_{4-9}$ alkenyl. In some embodiments, $R^L$ is optionally substituted $C_{4-8}$ alkenyl. In some embodiments, $R^L$ is optionally substituted $C_{4-7}$ alkenyl. In some embodiments, $R^L$ is optionally substituted $C_{4-6}$ alkenyl.

In some embodiments, $R^L$ is optionally substituted $C_{6-50}$ alkenyl. In some embodiments, $R^L$ is optionally substituted $C_{6-40}$ alkenyl. In some embodiments, $R^L$ is optionally substituted $C_{6-30}$ alkenyl. In some embodiments, $R^L$ is optionally substituted $C_{6-20}$ alkenyl. In some embodiments, $R^L$ is optionally substituted $C_{6-19}$ alkenyl. In some embodiments, $R^L$ is optionally substituted $C_{6-18}$ alkenyl. In some embodiments, $R^L$ is optionally substituted $C_{6-17}$ alkenyl. In some embodiments, $R^L$ is optionally substituted $C_{6-16}$ alkenyl. In some embodiments, $R^L$ is optionally substituted $C_{6-15}$ alkenyl. In some embodiments, $R^L$ is optionally substituted $C_{6-14}$ alkenyl. In some embodiments, $R^L$ is optionally substituted $C_{6-13}$ alkenyl. In some embodiments, $R^L$ is optionally substituted $C_{6-12}$ alkenyl. In some embodiments, $R^L$ is optionally substituted $C_{6-11}$ alkenyl. In some embodiments, $R^L$ is optionally substituted $C_{6-10}$ alkenyl. In some embodiments, $R^L$ is optionally substituted $C_{6-9}$ alkenyl. In some embodiments, $R^L$ is optionally substituted $C_{6-8}$ alkenyl. In some embodiments, $R^L$ is optionally substituted $C_{6-7}$ alkenyl.

In some embodiments, $R^L$ is optionally substituted $C_{8-50}$ alkenyl. In some embodiments, $R^L$ is optionally substituted $C_{8-40}$ alkenyl. In some embodiments, $R^L$ is optionally substituted $C_{8-30}$ alkenyl. In some embodiments, $R^L$ is optionally substituted $C_{8-20}$ alkenyl. In some embodiments, $R^L$ is optionally substituted $C_{8-19}$ alkenyl. In some embodiments, $R^L$ is optionally substituted $C_{8-18}$ alkenyl. In some embodiments, $R^L$ is optionally substituted $C_{8-17}$ alkenyl. In some embodiments, $R^L$ is optionally substituted $C_{8-16}$ alkenyl. In some embodiments, $R^L$ is optionally substituted $C_{8-15}$ alkenyl. In some embodiments, $R^L$ is optionally substituted $C_{8-14}$ alkenyl. In some embodiments, $R^L$ is optionally substituted $C_{8-13}$ alkenyl. In some embodiments, $R^L$ is optionally substituted $C_{8-12}$ alkenyl. In some embodiments, $R^L$ is optionally substituted $C_{8-11}$ alkenyl. In some embodiments, $R^L$ is optionally substituted $C_{8-10}$ alkenyl. In some embodiments, $R^L$ is optionally substituted $C_{8-9}$ alkenyl.

In some embodiments, $R^L$ is optionally substituted $C_{9-50}$ alkenyl. In some embodiments, $R^L$ is optionally substituted $C_{9-40}$ alkenyl. In some embodiments, $R^L$ is optionally substituted $C_{9-30}$ alkenyl. In some embodiments, $R^L$ is optionally substituted $C_{9-20}$ alkenyl. In some embodiments, $R^L$ is optionally substituted $C_{9-19}$ alkenyl. In some embodiments, $R^L$ is optionally substituted $C_{9-18}$ alkenyl. In some embodiments, $R^L$ is optionally substituted $C_{9-17}$ alkenyl. In some embodiments, $R^L$ is optionally substituted $C_{9-16}$ alkenyl. In some embodiments, $R^L$ is optionally substituted $C_{9-15}$ alkenyl. In some embodiments, $R^L$ is optionally substituted $C_{9-14}$ alkenyl. In some embodiments, $R^L$ is optionally substituted $C_{9-13}$ alkenyl. In some embodiments, $R^L$ is optionally substituted $C_{9-12}$ alkenyl. In some embodiments, $R^L$ is optionally substituted $C_{9-11}$ alkenyl. In some embodiments, $R^L$ is optionally substituted $C_{9-10}$ alkenyl.

In some embodiments, $R^L$ is optionally substituted $C_{10-50}$ alkenyl. In some embodiments, $R^L$ is optionally substituted $C_{10-40}$ alkenyl. In some embodiments, $R^L$ is optionally substituted $C_{10-30}$ alkenyl. In some embodiments, $R^L$ is optionally substituted $C_{10-20}$ alkenyl. In some embodiments, $R^L$ is optionally substituted $C_{10-19}$ alkenyl. In some embodiments, $R^L$ is optionally substituted $C_{10-18}$ alkenyl. In some embodiments, $R^L$ is optionally substituted $C_{10-17}$ alkenyl. In some embodiments, $R^L$ is optionally substituted $C_{10-16}$ alkenyl. In some embodiments, $R^L$ is optionally substituted $C_{10-15}$ alkenyl. In some embodiments, $R^L$ is optionally substituted $C_{10-14}$ alkenyl. In some embodiments, $R^L$ is optionally substituted $C_{10-13}$ alkenyl. In some embodiments, $R^L$ is optionally substituted $C_{10-12}$ alkenyl. In some embodiments, $R^L$ is optionally substituted $C_{10-11}$ alkenyl.

In some embodiments, $R^L$ is optionally substituted $C_{11-50}$ alkenyl. In some embodiments, $R^L$ is optionally substituted $C_{11-40}$ alkenyl. In some embodiments, $R^L$ is optionally substituted $C_{11-30}$ alkenyl. In some embodiments, $R^L$ is optionally substituted $C_{11-20}$ alkenyl. In some embodiments, $R^L$ is optionally substituted $C_{11-19}$ alkenyl. In some embodiments, $R^L$ is optionally substituted $C_{11-18}$ alkenyl. In some embodiments, $R^L$ is optionally substituted $C_{11-17}$ alkenyl. In some embodiments, $R^L$ is optionally substituted $C_{11-16}$ alkenyl. In some embodiments, $R^L$ is optionally substituted $C_{11-15}$ alkenyl. In some embodiments, $R^L$ is optionally substituted $C_{11-14}$ alkenyl. In some embodiments, $R^L$ is optionally substituted $C_{11-13}$ alkenyl. In some embodiments, $R^L$ is optionally substituted $C_{11-12}$ alkenyl.

In some embodiments, $R^L$ is optionally substituted $C_{12-50}$ alkenyl. In some embodiments, $R^L$ is optionally substituted $C_{12-40}$ alkenyl. In some embodiments, $R^L$ is optionally substituted $C_{12-30}$ alkenyl. In some embodiments, $R^L$ is optionally substituted $C_{12-20}$ alkenyl. In some embodiments, $R^L$ is optionally substituted $C_{12-19}$ alkenyl. In some embodiments, $R^L$ is optionally substituted $C_{12-18}$ alkenyl. In some embodiments, $R^L$ is optionally substituted $C_{12-17}$ alkenyl. In some embodiments, $R^L$ is optionally substituted $C_{12-16}$ alkenyl. In some embodiments, $R^L$ is optionally substituted $C_{12-15}$ alkenyl. In some embodiments, $R^L$ is optionally substituted $C_{12-14}$ alkenyl. In some embodiments, $R^L$ is optionally substituted $C_{12-13}$ alkenyl.

In some embodiments, $R^L$ is optionally substituted $C_6$ alkenyl. In some embodiments, $R^L$ is optionally substituted $C_7$ alkenyl. In some embodiments, $R^L$ is optionally substituted $C_8$ alkenyl. In some embodiments, $R^L$ is optionally substituted $C_9$ alkenyl. In some embodiments, $R^L$ is optionally substituted $C_{10}$ alkenyl. In some embodiments, $R^L$ is optionally substituted $C_{11}$ alkenyl. In some embodiments, $R^L$ is optionally substituted $C_{12}$ alkenyl. In some embodiments, $R^L$ is optionally substituted $C_{13}$ alkenyl. In some embodiments, $R^L$ is optionally substituted $C_{14}$ alkenyl. In some embodiments, $R^L$ is optionally substituted $C_{15}$ alkenyl. In some embodiments, $R^L$ is optionally substituted $C_{16}$ alkenyl. In some embodiments, $R^L$ is optionally substituted $C_{17}$ alkenyl. In some embodiments, $R^L$ is optionally substituted $C_{18}$ alkenyl. In some embodiments, $R^L$ is optionally substituted $C_{19}$ alkenyl. In some embodiments, $R^L$ is optionally substituted $C_{20}$ alkenyl.

In some embodiments, for example, in any of the above embodiments, $R^L$ is a substituted alkyl group. In some embodiments, $R^L$ is an unsubstituted alkyl group. In some embodiments, $R^L$ is an optionally substituted straight-chain alkenyl group. In some embodiments, $R^L$ is a substituted straight-chain alkenyl group. In some embodiments, $R^L$ is an unsubstituted straight-chain alkenyl group. In some embodiments, $R^L$ is an optionally substituted branched alkenyl group. In some embodiments, $R^L$ is a substituted branched alkenyl group. In some embodiments, $R^L$ is an unsubstituted branched alkenyl group.

Exemplary unsubstituted alkenyl group include, but are not limited to:

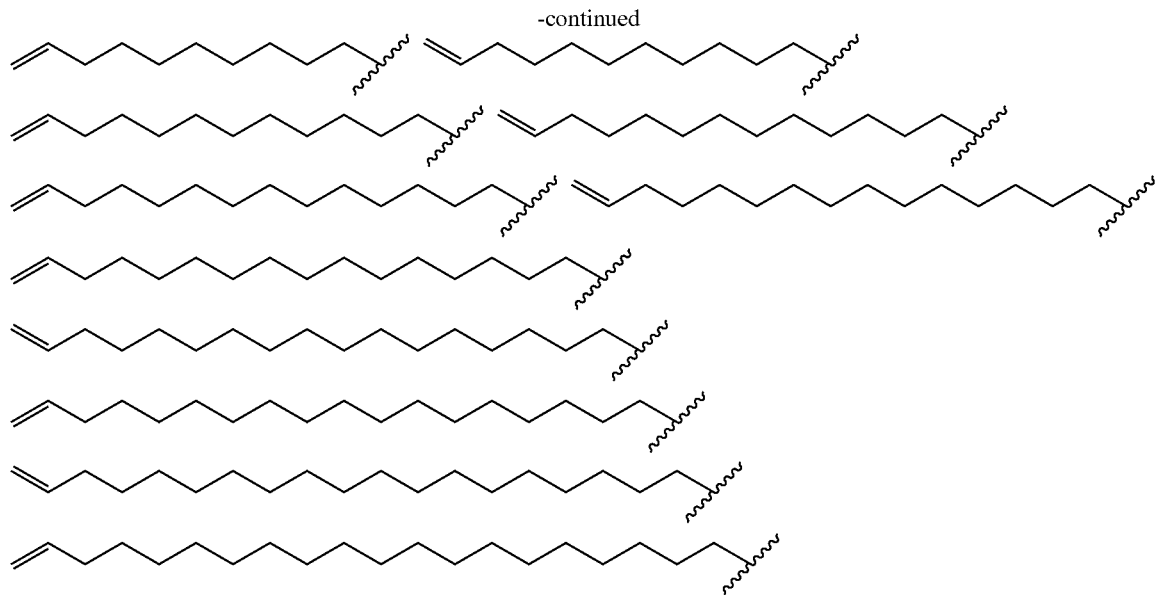

Myristoleic —(CH$_2$)$_7$CH=CH(CH$_2$)$_3$CH$_3$,
Palmitoliec —(CH$_2$)$_7$CH=CH(CH$_2$)$_5$CH$_3$,
Sapienic —(CH$_2$)$_4$CH=CH(CH$_2$)$_8$CH$_3$,
Oleic —(CH$_2$)$_7$CH=CH(CH$_2$)$_7$CH$_3$,
Linoleic —(CH$_2$)$_7$CH=CHCH$_2$CH=CH(CH$_2$)$_4$CH$_3$,
α-Linolenic —(CH$_2$)$_7$CH=CHCH$_2$CH=CHCH$_2$CH=CHCH$_2$CH$_3$,
Arachinodonic —(CH$_2$)$_3$CH=CHCH$_2$CH=CHCH$_2$CH=CHCH$_2$ CH=CH(CH$_2$)$_4$CH$_3$,
Eicosapentaenoic —(CH$_2$)$_3$CH=CHCH$_2$CH=CHCH$_2$CH=CHCH$_2$ CH=CHCH$_2$CH=CHCH$_2$CH$_3$,
Erucic —(CH$_2$)$_{11}$CH=CH(CH$_2$)$_7$CH$_3$, and
Docosahexaenoic —(CH$_2$)$_2$CH=CHCH$_2$CH=CHCH$_2$CH=CHCH$_2$CH=CHCH$_2$CH=CHCH$_2$CH=CH—CH$_2$CH$_3$.

In some embodiments, wherein R$^L$ is defined as a C$_{6-50}$alkyl or C$_{6-50}$alkenyl groups, such groups are meant to encompass lipophilic groups (also referred to as a "lipid tail"). Lipophilic groups comprise a group of molecules that include fats, waxes, oils, fatty acids, and the like. Lipid tails present in these lipid groups can be saturated and unsaturated, depending on whether or not the lipid tail comprises double bonds. The lipid tail can also comprise different lengths, often categorized as medium (i.e., with tails between 7-12 carbons, e.g., C$_{7-12}$ alkyl or C$_{7-12}$ alkenyl), long (i.e., with tails greater than 12 carbons and up to 22 carbons, e.g., C$_{13-22}$alkyl or C$_{13-22}$ alkenyl), or very long (i.e., with tails greater than 22 carbons, e.g., C$_{23-30}$ alkyl or C$_{23-30}$ alkenyl).

In some embodiments, R$^L$ is optionally substituted C$_{2-50}$ alkynyl. In some embodiments, R$^L$ is optionally substituted C$_{2-40}$ alkynyl. In some embodiments, R$^L$ is optionally substituted C$_{2-30}$ alkynyl. In some embodiments, R$^L$ is optionally substituted C$_{2-20}$ alkynyl. In some embodiments, R$^L$ is optionally substituted C$_{2-19}$ alkynyl. In some embodiments, R$^L$ is optionally substituted C$_{2-18}$ alkynyl. In some embodiments, R$^L$ is optionally substituted C$_{2-17}$ alkynyl. In some embodiments, R$^L$ is optionally substituted C$_{2-16}$ alkynyl. In some embodiments, R$^L$ is optionally substituted C$_{2-15}$ alkynyl. In some embodiments, R$^L$ is optionally substituted C$_{2-14}$ alkynyl. In some embodiments, R$^L$ is optionally substituted C$_{2-13}$ alkynyl. In some embodiments, R$^L$ is optionally substituted C$_{2-12}$ alkynyl. In some embodiments, R$^L$ is optionally substituted C$_{2-11}$ alkynyl. In some embodiments, R$^L$ is optionally substituted C$_{2-10}$ alkynyl. In some embodiments, R$^L$ is optionally substituted C$_{2-9}$ alkynyl. In some embodiments, R$^L$ is optionally substituted C$_{2-8}$ alkynyl. In some embodiments, R$^L$ is optionally substituted C$_{2-7}$ alkynyl. In some embodiments, R$^L$ is optionally substituted C$_{2-6}$ alkynyl.

In some embodiments, R$^L$ is optionally substituted C$_{4-50}$ alkynyl. In some embodiments, R$^L$ is optionally substituted C$_{4-40}$ alkynyl. In some embodiments, R$^L$ is optionally substituted C$_{4-30}$ alkynyl. In some embodiments, R$^L$ is optionally substituted C$_{4-20}$ alkynyl. In some embodiments, R$^L$ is optionally substituted C$_{4-19}$ alkynyl. In some embodiments, R$^L$ is optionally substituted C$_{4-18}$ alkynyl. In some embodiments, R$^L$ is optionally substituted C$_{4-17}$ alkynyl. In some embodiments, R$^L$ is optionally substituted C$_{4-16}$ alkynyl. In some embodiments, R$^L$ is optionally substituted C$_{4-15}$ alkynyl. In some embodiments, R$^L$ is optionally substituted C$_{4-14}$ alkynyl. In some embodiments, R$^L$ is optionally substituted C$_{4-13}$ alkynyl. In some embodiments, R$^L$ is optionally substituted C$_{4-12}$ alkynyl. In some embodiments, R$^L$ is optionally substituted C$_{4-11}$ alkynyl. In some embodiments, R$^L$ is optionally substituted C$_{4-10}$ alkynyl. In some embodiments, R$^L$ is optionally substituted C$_{4-9}$ alkynyl. In some embodiments, R$^L$ is optionally substituted C$_{4-8}$ alkynyl. In some embodiments, R$^L$ is optionally substituted C$_{4-7}$ alkynyl. In some embodiments, R$^L$ is optionally substituted C$_{4-6}$ alkynyl.

In some embodiments, R$^L$ is optionally substituted C$_{6-50}$ alkynyl. In some embodiments, R$^L$ is optionally substituted C$_{6-40}$ alkynyl. In some embodiments, R$^L$ is optionally substituted C$_{6-30}$ alkynyl. In some embodiments, R$^L$ is optionally substituted C$_{6-20}$ alkynyl. In some embodiments, R$^L$ is optionally substituted C$_{6-19}$ alkynyl. In some embodiments, R$^L$ is optionally substituted C$_{6-18}$ alkynyl. In some embodiments, R$^L$ is optionally substituted C$_{6-17}$ alkynyl. In some embodiments, R$^L$ is optionally substituted C$_{6-16}$ alkynyl. In some embodiments, R$^L$ is optionally substituted C$_{6-15}$ alkynyl. In some embodiments, R$^L$ is optionally substituted C$_{6-14}$ alkynyl. In some embodiments, R$^L$ is optionally substituted $C_{6-13}$ alkynyl. In some embodiments, $R^L$ is optionally substituted $C_{6-12}$ alkynyl. In some embodiments, $R^L$ is optionally substituted $C_{6-11}$ alkynyl. In some embodiments, $R^L$ is optionally substituted $C_{6-10}$ alkynyl. In some embodiments, $R^L$ is optionally substituted $C_{6-9}$ alkynyl. In some embodiments, $R^L$ is optionally substituted $C_{6-8}$ alkynyl. In some embodiments, $R^L$ is optionally substituted $C_{6-7}$ alkynyl.

In some embodiments, $R^L$ is optionally substituted $C_{8-50}$ alkynyl. In some embodiments, $R^L$ is optionally substituted $C_{8-40}$ alkynyl. In some embodiments, $R^L$ is optionally substituted $C_{8-30}$ alkynyl. In some embodiments, $R^L$ is optionally substituted $C_{8-20}$ alkynyl. In some embodiments, $R^L$ is optionally substituted $C_{8-19}$ alkynyl. In some embodiments, $R^L$ is optionally substituted $C_{8-18}$ alkynyl. In some embodiments, $R^L$ is optionally substituted $C_{8-17}$ alkynyl. In some embodiments, $R^L$ is optionally substituted $C_8$-16 alkynyl. In some embodiments, $R^L$ is optionally substituted $C_{8-15}$ alkynyl. In some embodiments, $R^L$ is optionally substituted $C_{8-14}$ alkynyl. In some embodiments, $R^L$ is optionally substituted $C_{8-13}$ alkynyl. In some embodiments, $R^L$ is optionally substituted $C_{8-12}$ alkynyl. In some embodiments, $R^L$ is optionally substituted $C_{8-11}$ alkynyl. In some embodiments, $R^L$ is optionally substituted $C_{8-10}$ alkynyl. In some embodiments, $R^L$ is optionally substituted $C_{8-9}$ alkynyl.

In some embodiments, $R^L$ is optionally substituted $C_{9-50}$ alkynyl. In some embodiments, $R^L$ is optionally substituted $C_{9-40}$ alkynyl. In some embodiments, $R^L$ is optionally substituted $C_{9-30}$ alkynyl. In some embodiments, $R^L$ is optionally substituted $C_{9-20}$ alkynyl. In some embodiments, $R^L$ is optionally substituted $C_{9-19}$ alkynyl. In some embodiments, $R^L$ is optionally substituted $C_{9-18}$ alkynyl. In some embodiments, $R^L$ is optionally substituted $C_{9-17}$ alkynyl. In some embodiments, $R^L$ is optionally substituted $C_{9-16}$ alkynyl. In some embodiments, $R^L$ is optionally substituted $C_{9-15}$ alkynyl. In some embodiments, $R^L$ is optionally substituted $C_{9-14}$ alkynyl. In some embodiments, $R^L$ is optionally substituted $C_{9-13}$ alkynyl. In some embodiments, $R^L$ is optionally substituted $C_{9-12}$ alkynyl. In some embodiments, $R^L$ is optionally substituted $C_{9-11}$ alkynyl. In some embodiments, $R^L$ is optionally substituted $C_{9-10}$ alkynyl.

In some embodiments, $R^L$ is optionally substituted $C_{10-50}$ alkynyl. In some embodiments, $R^L$ is optionally substituted $C_{10-40}$ alkynyl. In some embodiments, $R^L$ is optionally substituted $C_{10-30}$ alkynyl. In some embodiments, $R^L$ is optionally substituted $C_{10-20}$ alkynyl. In some embodiments, $R^L$ is optionally substituted $C_{10-19}$ alkynyl. In some embodiments, $R^L$ is optionally substituted $C_{10-18}$ alkynyl. In some embodiments, $R^L$ is optionally substituted $C_{10-17}$ alkynyl. In some embodiments, $R^L$ is optionally substituted $C_{10-16}$ alkynyl. In some embodiments, $R^L$ is optionally substituted $C_{10-15}$ alkynyl. In some embodiments, $R^L$ is optionally substituted $C_{10-14}$ alkynyl. In some embodiments, $R^L$ is optionally substituted $C_{10-13}$ alkynyl. In some embodiments, $R^L$ is optionally substituted $C_{10-12}$ alkynyl. In some embodiments, $R^L$ is optionally substituted $C_{10-11}$ alkynyl.

In some embodiments, $R^L$ is optionally substituted $C_{11-50}$ alkynyl. In some embodiments, $R^L$ is optionally substituted $C_{11-40}$ alkynyl. In some embodiments, $R^L$ is optionally substituted $C_{11-30}$ alkynyl. In some embodiments, $R^L$ is optionally substituted $C_{1-20}$ alkynyl. In some embodiments, $R^L$ is optionally substituted $C_{11-19}$ alkynyl. In some embodiments, $R^L$ is optionally substituted $C_{11-18}$ alkynyl. In some embodiments, $R^L$ is optionally substituted $C_{11-17}$ alkynyl. In some embodiments, $R^L$ is optionally substituted $C_{11-16}$ alkynyl. In some embodiments, $R^L$ is optionally substituted $C_{11-15}$ alkynyl. In some embodiments, $R^L$ is optionally substituted $C_{11-14}$ alkynyl. In some embodiments, $R^L$ is optionally substituted $C_{11-13}$ alkynyl. In some embodiments, $R^L$ is optionally substituted $C_{11-12}$ alkynyl.

In some embodiments, $R^L$ is optionally substituted $C_{12-50}$ alkynyl. In some embodiments, $R^L$ is optionally substituted $C_{12-40}$ alkynyl. In some embodiments, $R^L$ is optionally substituted $C_{12-30}$ alkynyl. In some embodiments, $R^L$ is optionally substituted $C_{12-20}$ alkynyl. In some embodiments, $R^L$ is optionally substituted $C_{12-19}$ alkynyl. In some embodiments, $R^L$ is optionally substituted $C_{12-18}$ alkynyl. In some embodiments, $R^L$ is optionally substituted $C_{12-17}$ alkynyl. In some embodiments, $R^L$ is optionally substituted $C_{12-16}$ alkynyl. In some embodiments, $R^L$ is optionally substituted $C_{12-15}$ alkynyl. In some embodiments, $R^L$ is optionally substituted $C_{12-14}$ alkynyl. In some embodiments, $R^L$ is optionally substituted $C_{12-13}$ alkynyl.

In some embodiments, $R^L$ is optionally substituted $C_6$ alkynyl. In some embodiments, $R^L$ is optionally substituted $C_7$ alkynyl. In some embodiments, $R^L$ is optionally substituted $C_8$ alkynyl. In some embodiments, $R^L$ is optionally substituted $C_9$ alkynyl. In some embodiments, $R^L$ is optionally substituted $C_{10}$ alkynyl. In some embodiments, $R^L$ is optionally substituted $C_{11}$ alkynyl. In some embodiments, $R^L$ is optionally substituted $C_{12}$ alkynyl. In some embodiments, $R^L$ is optionally substituted $C_{13}$ alkynyl. In some embodiments, $R^L$ is optionally substituted $C_{14}$ alkynyl. In some embodiments, $R^L$ is optionally substituted $C_{15}$ alkynyl. In some embodiments, $R^L$ is optionally substituted $C_{16}$ alkynyl. In some embodiments, $R^L$ is optionally substituted $C_{17}$ alkynyl. In some embodiments, $R^L$ is optionally substituted $C_{18}$ alkynyl. In some embodiments, $R^L$ is optionally substituted $C_{19}$ alkynyl. In some embodiments, $R^L$ is optionally substituted $C_{20}$ alkynyl.

In some embodiments, for example, in any of the above embodiments, $R^L$ is a substituted alkynyl group. In some embodiments, $R^L$ is an unsubstituted alkynyl group. In some embodiments, $R^L$ is an optionally substituted straight-chain alkyl group. In some embodiments, $R^L$ is an optionally substituted straight-chain alkynyl group. In some embodiments, $R^L$ is a substituted straight-chain alkynyl group. In some embodiments, $R^L$ is an unsubstituted straight-chain alkynyl group. In some embodiments, $R^L$ is an optionally substituted branched alkynyl group. In some embodiments, $R^L$ is a substituted branched alkynyl group. In some embodiments, $R^L$ is an unsubstituted branched alkynyl group.

In some embodiments, $R^L$ is optionally substituted hetero$C_{1-50}$alkyl. In some embodiments, $R^L$ is optionally substituted hetero$C_{2-50}$-alkyl. In some embodiments, $R^L$ is optionally substituted hetero$C_{2-40}$alkyl. In some embodiments, $R^L$ is optionally substituted hetero$C_{2-30}$alkyl. In some embodiments, $R^L$ is optionally substituted hetero$C_{2-20}$alkyl. In some embodiments, $R^L$ is optionally substituted hetero$C_{2-19}$alkyl. In some embodiments, $R^L$ is optionally substituted hetero$C_{2-18}$alkyl. In some embodiments, $R^L$ is optionally substituted hetero$C_{2-17}$alkyl. In some embodiments, $R^L$ is optionally substituted hetero$C_{2-16}$alkyl. In some embodiments, $R^L$ is optionally substituted hetero$C_{2-15}$alkyl. In some embodiments, $R^L$ is optionally substituted hetero$C_{2-14}$alkyl. In some embodiments, $R^L$ is optionally substituted hetero$C_{2-13}$alkyl. In some embodiments, $R^L$ is optionally substituted hetero$C_{2-12}$alkyl. In some embodiments, $R^L$ is optionally substituted hetero$C_{2-11}$alkyl. In some embodiments, $R^L$ is optionally substituted hetero$C_{2-10}$alkyl. In some embodiments, $R^L$ is optionally substituted hetero$C_{2-9}$alkyl. In some embodiments, $R^L$ is optionally substituted hetero$C_{2-8}$alkyl. In some embodiments, $R^L$ is optionally substituted hetero$C_{2-7}$alkyl. In some embodiments, $R^L$ is optionally substituted hetero$C_{2-6}$alkyl.

In some embodiments, $R^L$ is optionally substituted heteroC$_{4-50}$alkyl. In some embodiments, $R^L$ is optionally substituted heteroC$_{4-40}$alkyl. In some embodiments, $R^L$ optionally substituted heteroC$_{4-30}$alkyl. In some embodiments, $R^L$ is optionally substituted heteroC$_{4-20}$alkyl. In some embodiments, $R^L$ is optionally substituted heteroC$_{4-19}$alkyl. In some embodiments, $R^L$ is optionally substituted heteroC$_{4-18}$alkyl. In some embodiments, $R^L$ is optionally substituted heteroC$_{4-17}$alkyl. In some embodiments, $R^L$ is optionally substituted heteroC$_{4-16}$alkyl. In some embodiments, $R^L$ is optionally substituted heteroC$_{4-15}$alkyl. In some embodiments, $R^L$ is optionally substituted heteroC$_{4-14}$alkyl. In some embodiments, $R^L$ is optionally substituted heteroC$_{4-13}$alkyl. In some embodiments, $R^L$ is optionally substituted heteroC$_{4-12}$alkyl. In some embodiments, $R^L$ is optionally substituted heteroC$_{4-11}$alkyl. In some embodiments, $R^L$ is optionally substituted heteroC$_{4-10}$alkyl. In some embodiments, $R^L$ is optionally substituted heteroC$_{4-9}$alkyl. In some embodiments, $R^L$ is optionally substituted heteroC$_{4-8}$alkyl. In some embodiments, $R^L$ is optionally substituted heteroC$_{4-7}$alkyl. In some embodiments, $R^L$ is optionally substituted heteroC$_{4-6}$alkyl.

In some embodiments, $R^L$ is optionally substituted heteroC$_{6-50}$alkyl. In some embodiments, $R^L$ is optionally substituted heteroC$_{6-40}$alkyl. In some embodiments, $R^L$ optionally substituted heteroC$_{6-30}$alkyl. In some embodiments, $R^L$ is optionally substituted heteroC$_{6-20}$alkyl. In some embodiments, $R^L$ is optionally substituted heteroC$_{6-19}$alky. In some embodiments, $R^L$ is optionally substituted heteroC$_{6-18}$alkyl. In some embodiments, $R^L$ is optionally substituted heteroC$_{6-17}$alkyl. In some embodiments, $R^L$ is optionally substituted heteroC$_{6-16}$alkyl. In some embodiments, $R^L$ is optionally substituted heteroC$_{6-15}$alkyl. In some embodiments, $R^L$ is optionally substituted heteroC$_{6-14}$alkyl. In some embodiments, $R^L$ optionally substituted heteroC$_{6-13}$alkyl. In some embodiments, $R^L$ is optionally substituted heteroC$_{6-12}$alkyl. In some embodiments, $R^L$ is optionally substituted heteroC$_{6-11}$alkyl. In some embodiments, $R^L$ is optionally substituted heteroC$_{6-10}$alkyl. In some embodiments, $R^L$ is optionally substituted heteroC$_{6-9}$alkyl. In some embodiments, $R^L$ is optionally substituted heteroC$_{6-8}$alkyl. In some embodiments, $R^L$ is optionally substituted heteroC$_{6-7}$alkyl.

In some embodiments, $R^L$ is optionally substituted heteroC$_{8-50}$alkyl. In some embodiments, $R^L$ is optionally substituted heteroC$_{8-40}$alkyl. In some embodiments, $R^L$ is optionally substituted heteroC$_{8-30}$alkyl. In some embodiments, $R^L$ is optionally substituted heteroC$_{8-20}$alkyl. In some embodiments, $R^L$ is optionally substituted heteroC$_{8-19}$alkyl. In some embodiments, $R^L$ is optionally substituted heteroC$_{8-18}$alkyl. In some embodiments, $R^L$ is optionally substituted heteroC$_{8-17}$alkyl. In some embodiments, $R^L$ is optionally substituted heteroC$_{8-16}$alkyl. In some embodiments, $R^L$ is optionally substituted heteroC$_{8-15}$alkyl. In some embodiments, $R^L$ is optionally substituted heteroC$_{8-14}$alkyl. In some embodiments, $R^L$ is optionally substituted heteroC$_{8-13}$alkyl. In some embodiments, $R^L$ is optionally substituted heteroC$_{8-12}$alkyl. In some embodiments, $R^L$ is optionally substituted heteroC$_{8-11}$alkyl. In some embodiments, $R^L$ is optionally substituted heteroC$_{8-10}$alkyl. In some embodiments, $R^L$ is optionally substituted heteroC$_{8-9}$alkyl.

In some embodiments, $R^L$ is optionally substituted heteroC$_{9-50}$alkyl. In some embodiments, $R^L$ is optionally substituted heteroC$_{9-40}$alkyl. In some embodiments, $R^L$ is optionally substituted heteroC$_{9-30}$alkyl. In some embodiments, $R^L$ is optionally substituted heteroC$_{9-20}$alkyl. In some embodiments, $R^L$ is optionally substituted heteroC$_{9-19}$alkyl. In some embodiments, $R^L$ is optionally substituted heteroC$_{9-18}$alkyl. In some embodiments, $R^L$ is optionally substituted heteroC$_{9-17}$alkyl. In some embodiments, $R^L$ is optionally substituted heteroC$_{9-16}$alkyl. In some embodiments, $R^L$ is optionally substituted heteroC$_{9-15}$alkyl. In some embodiments, $R^L$ is optionally substituted heteroC$_{9-14}$alkyl. In some embodiments, $R^L$ is optionally substituted heteroC$_{9-13}$alkyl. In some embodiments, $R^L$ is optionally substituted heteroC$_{9-12}$alkyl. In some embodiments, $R^L$ is optionally substituted heteroC$_{9-11}$alkyl. In some embodiments, $R^L$ is optionally substituted heteroC$_{9-10}$alkyl.

In some embodiments, $R^L$ is optionally substituted heteroC$_{10-50}$alkyl. In some embodiments, $R^L$ is optionally substituted heteroC$_{10-40}$alkyl. In some embodiments, R is optionally substituted heteroC$_{10-30}$alkyl. In some embodiments, $R^L$ is optionally substituted heteroC$_{10-20}$alkyl. In some embodiments, $R^L$ is optionally substituted heteroC$_{10-19}$alkyl. In some embodiments, $R^L$ is optionally substituted heteroC$_{10-18}$alkyl. In some embodiments, $R^L$ optionally substituted heteroC$_{10-17}$alkyl. In some embodiments, $R^L$ is optionally substituted heteroC$_{10-16}$alkyl. In some embodiments, $R^L$ is optionally substituted heteroC$_{10-15}$alkyl. In some embodiments, $R^L$ is optionally substituted heteroC$_{10-14}$alkyl. In some embodiments, $R^L$ is optionally substituted heteroC$_{10-13}$alkyl. In some embodiments, $R^L$ is optionally substituted heteroC$_{10-12}$alkyl. In some embodiments, $R^L$ is optionally substituted heteroC$_{10-11}$alkyl.

In some embodiments, $R^L$ is optionally substituted heteroC$_{11-50}$alkyl. In some embodiments, $R^L$ is optionally substituted heteroC$_{11-40}$alkyl. In some embodiments, $R^L$ is optionally substituted heteroC$_{11-30}$alkyl. In some embodiments, $R^L$ is optionally substituted heteroC$_{11-20}$alkyl. In some embodiments, $R^L$ is optionally substituted heteroC$_{11-19}$alkyl. In some embodiments, $R^L$ is optionally substituted heteroC$_{11-18}$alkyl. In some embodiments, $R^L$ is optionally substituted heteroC$_{11-17}$alkyl. In some embodiments, $R^L$ is optionally substituted heteroC$_{11-16}$alkyl. In some embodiments, $R^L$ is optionally substituted heteroC$_{11-15}$alkyl. In some embodiments, $R^L$ is optionally substituted heteroC$_{11-14}$alkyl. In some embodiments, $R^L$ is optionally substituted heteroC$_{11-13}$alkyl. In some embodiments, $R^L$ is optionally substituted heteroC$_{11-12}$alkyl.

In some embodiments, $R^L$ is optionally substituted heteroC$_{12-50}$alkyl. In some embodiments, $R^L$ is optionally substituted heteroC$_{12-40}$alkyl. In some embodiments, $R^L$ is optionally substituted heteroC$_{12-30}$alkyl. In some embodiments, $R^L$ is optionally substituted heteroC$_{12-20}$alkyl. In some embodiments, $R^L$ is optionally substituted heteroC$_{12-19}$alkyl. In some embodiments, $R^L$ is optionally substituted heteroC$_{12-18}$alkyl. In some embodiments, $R^L$ is optionally substituted heteroC$_{12-17}$alkyl. In some embodiments, $R^L$ is optionally substituted heteroC$_{12-16}$alkyl. In some embodiments, $R^L$ is optionally substituted heteroC$_{12-15}$alkyl. In some embodiments, $R^L$ is optionally substituted heteroC$_{12-14}$alkyl. In some embodiments, $R^L$ is optionally substituted heteroC$_{12-13}$alkyl.

In some embodiments, $R^L$ is optionally substituted heteroC$_6$alkyl. In some embodiments, $R^L$ is optionally substituted heteroC$_7$alkyl. In some embodiments, $R^L$ is optionally substituted heteroC$_8$alkyl. In some embodiments, $R^L$ is optionally substituted heteroC$_9$alkyl. In some embodiments, $R^L$ is optionally substituted heteroC$_{10}$alkyl. In some embodiments, $R^L$ is optionally substituted heteroC$_{11}$alkyl. In some embodiments, $R^L$ is optionally substituted heteroC$_{12}$alkyl. In some embodiments, $R^L$ is optionally substituted heteroC$_{13}$alkyl. In some embodiments, $R^L$ is optionally substituted heteroC$_{14}$alkyl. In some embodiments, $R^L$ is optionally substituted heteroC$_{15}$alkyl. In some embodiments, $R^L$ is optionally substituted heteroC$_{16}$alkyl. In some embodiments, $R^L$ is optionally substituted heteroC$_{17}$alkyl. In some embodiments, $R^L$ is optionally substituted heteroC$_{18}$alkyl. In some embodiments, $R^L$ is optionally substituted heteroC$_{19}$alkyl. In some embodiments, $R^L$ is optionally substituted heteroC$_{20}$alkyl.

In some embodiments, for example, in any of the above embodiments, $R^L$ is a substituted heteroalkyl group. In some embodiments, $R^L$ is an unsubstituted heteroalkyl group. In some embodiments, $R^L$ is an optionally substituted straight-chain heteroalkyl group. In some embodiments, $R^L$ is a substituted straight-chain heteroalkyl group. In some embodiments, $R^L$ an unsubstituted straight-chain heteroalkyl group. In some embodiments, $R^L$ is an optionally substituted branched heteroalkyl group. In some embodiments, $R^L$ is a substituted branched heteroalkyl group. In some embodiments, $R^L$ is an unsubstituted branched heteroalkyl group.

Exemplary unsubstituted heteroalkyl groups include, but are not limited to:

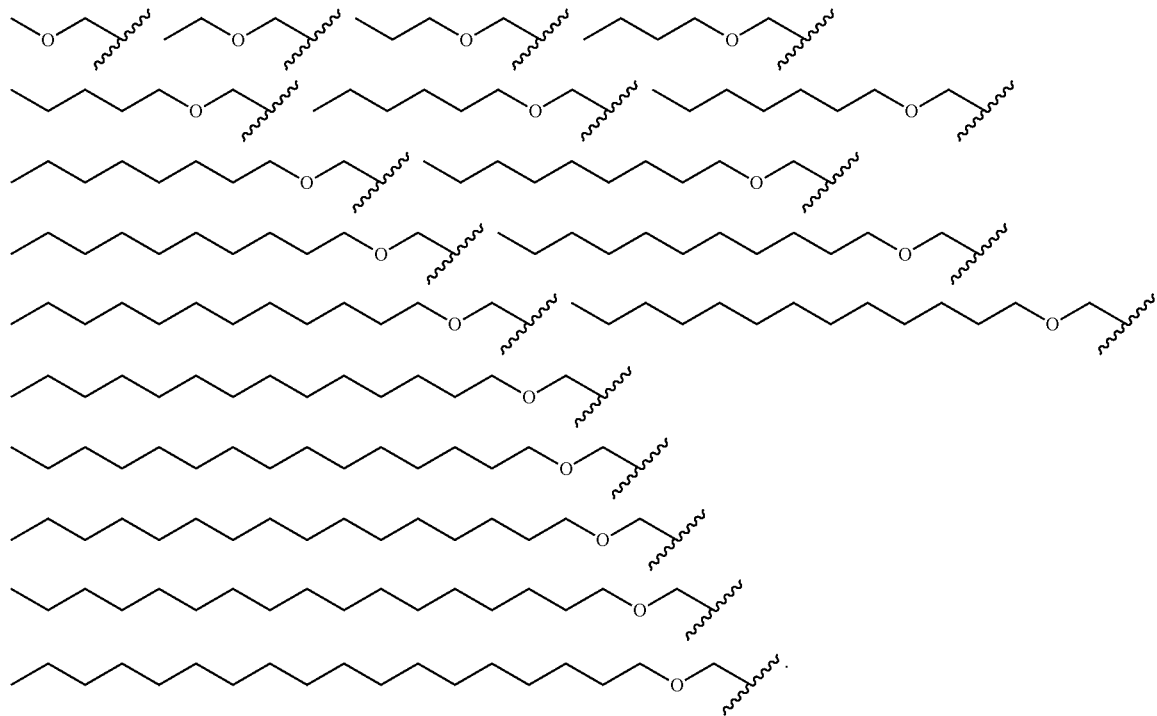

In some embodiments, $R^L$ is optionally substituted heteroC$_{2-50}$alkenyl. In some embodiments, $R^L$ is optionally substituted heteroC$_{2-40}$alkenyl. In some embodiments, $R^L$ is optionally substituted heteroC$_{2-30}$alkenyl. In some embodiments, $R^L$ is optionally substituted heteroC$_{2-20}$alkenyl. In some embodiments, $R^L$ is optionally substituted heteroC$_{2-19}$alkenyl. In some embodiments, $R^L$ is optionally substituted heteroC$_{2-18}$alkenyl. In some embodiments, $R^L$ is optionally substituted heteroC$_{2-17}$alkenyl. In some embodiments, $R^L$ is optionally substituted heteroC$_{2-16}$alkenyl. In some embodiments, $R^L$ is optionally substituted heteroC$_{2-15}$alkenyl. In some embodiments, $R^L$ is optionally substituted heteroC$_{2-14}$alkenyl. In some embodiments, $R^L$ is optionally substituted heteroC$_{2-13}$alkenyl. In some embodiments, $R^L$ is optionally substituted heteroC$_{2-12}$alkenyl. In some embodiments, $R^L$ is optionally substituted heteroC$_{2-11}$alkenyl. In some embodiments, $R^L$ is optionally substituted heteroC$_{2-10}$alkenyl. In some embodiments, $R^L$ is optionally substituted heteroC$_{2-9}$ alkenyl. In some embodiments, $R^L$ is optionally substituted heteroC$_{2-8}$alkenyl. In some embodiments, $R^L$ is optionally substituted heteroC$_{2-7}$alkenyl. In some embodiments, $R^L$ is optionally substituted heteroC$_{2-6}$alkenyl.

In some embodiments, $R^L$ is optionally substituted heteroC$_{4-50}$alkenyl. In some embodiments, $R^L$ is optionally substituted heteroC$_{4-40}$alkenyl. In some embodiments, $R^L$ is optionally substituted heteroC$_{4-30}$alkenyl. In some embodiments, $R^L$ is optionally substituted heteroC$_{4-20}$alkenyl. In some embodiments, $R^L$ is optionally substituted heteroC$_{4-19}$alkenyl. In some embodiments, $R^L$ is optionally substituted heteroC$_{4-18}$alkenyl. In some embodiments, $R^L$ is optionally substituted heteroC$_{4-17}$alkenyl. In some embodiments, $R^L$ is optionally substituted heteroC$_{4-16}$alkenyl. In some embodiments, $R^L$ is optionally substituted heteroC$_{4-15}$alkenyl. In some embodiments, $R^L$ is optionally substituted heteroC$_{4-14}$ alkenyl. In some embodiments, $R^L$ is optionally substituted heteroC$_{4-13}$alkenyl. In some embodiments, $R^L$ is optionally substituted heteroC$_{4-12}$alkenyl. In some embodiments, $R^L$ is optionally substituted heteroC$_{4-11}$alkenyl. In some embodiments, $R^L$ is optionally substituted heteroC$_{4-10}$alkenyl. In some embodiments, $R^L$ is optionally substituted heteroC$_{4-9}$ alkenyl. In some embodiments, $R^L$ is optionally substituted heteroC$_{4-8}$alkenyl. In some embodiments, $R^L$ is optionally substituted heteroC$_{4-7}$alkenyl. In some embodiments, $R^L$ is optionally substituted heteroC$_{4-6}$alkenyl.

In some embodiments, $R^L$ is optionally substituted heteroC$_{6-50}$alkenyl. In some embodiments, $R^L$ is optionally substituted heteroC$_{6-40}$alkenyl. In some embodiments, $R^L$ is optionally substituted heteroC$_{6-30}$alkenyl. In some embodiments, $R^L$ is optionally substituted heteroC$_{6-20}$alkenyl. In some embodiments, $R^L$ is optionally substituted heteroC$_{6-19}$ alkenyl. In some embodiments, $R^L$ is optionally substituted heteroC$_{6-18}$alkenyl. In some embodiments, $R^L$ is optionally substituted heteroC$_{6-17}$alkenyl. In some embodiments, R$^L$ is optionally substituted heteroC$_{6-16}$alkenyl. In some embodiments, R$^L$ is optionally substituted heteroC$_{6-15}$alkenyl. In some embodiments, R$^L$ is optionally substituted heteroC$_{6-14}$alkenyl. In some embodiments, R$^L$ is optionally substituted heteroC$_{6-13}$alkenyl. In some embodiments, R$^L$ is optionally substituted heteroC$_{6-12}$alkenyl. In some embodiments, R$^L$ is optionally substituted heteroC$_{6-11}$alkenyl. In some embodiments, R$^L$ is optionally substituted heteroC$_{6-10}$alkenyl. In some embodiments, R$^L$ is optionally substituted heteroC$_{6-9}$alkenyl. In some embodiments, R$^L$ is optionally substituted heteroC$_{6-8}$alkenyl. In some embodiments, R$^L$ is optionally substituted heteroC$_{6-7}$alkenyl.

In some embodiments, R$^L$ is optionally substituted heteroC$_{8-50}$alkenyl. In some embodiments, R$^L$ is optionally substituted heteroC$_{8-40}$alkenyl. In some embodiments, R$^L$ is optionally substituted heteroC$_{8-30}$alkenyl. In some embodiments, R$^L$ is optionally substituted heteroC$_{8-20}$alkenyl. In some embodiments, R$^L$ is optionally substituted heteroC$_{8-19}$alkenyl. In some embodiments, R$^L$ is optionally substituted heteroC$_{8-18}$alkenyl. In some embodiments, R$^L$ is optionally substituted heteroC$_{8-17}$alkenyl. In some embodiments, R$^L$ is optionally substituted heteroC$_{8-16}$alkenyl. In some embodiments, R$^L$ is optionally substituted heteroC$_{8-15}$alkenyl. In some embodiments, R$^L$ is optionally substituted heteroC$_{8-14}$alkenyl. In some embodiments, R$^L$ is optionally substituted heteroC$_{8-13}$alkenyl. In some embodiments, R$^L$ is optionally substituted heteroC$_{8-12}$alkenyl. In some embodiments, R$^L$ is optionally substituted heteroC$_{8-11}$alkenyl. In some embodiments, R$^L$ is optionally substituted heteroC$_{8-10}$alkenyl. In some embodiments, R$^L$ is optionally substituted heteroC$_{8-9}$alkenyl.

In some embodiments, R$^L$ is optionally substituted heteroC$_{9-50}$alkenyl. In some embodiments, R$^L$ is optionally substituted heteroC$_{9-40}$alkenyl. In some embodiments, R$^L$ is optionally substituted heteroC$_{9-30}$alkenyl. In some embodiments, R$^L$ is optionally substituted heteroC$_{9-20}$alkenyl. In some embodiments, R$^L$ is optionally substituted heteroC$_{9-19}$alkenyl. In some embodiments, R$^L$ is optionally substituted heteroC$_{9-18}$alkenyl. In some embodiments, R$^L$ is optionally substituted heteroC$_{9-17}$alkenyl. In some embodiments, R$^L$ is optionally substituted heteroC$_{9-16}$alkenyl. In some embodiments, R$^L$ is optionally substituted heteroC$_{9-15}$alkenyl. In some embodiments, R$^L$ is optionally substituted heteroC$_{9-14}$alkenyl. In some embodiments, R$^L$ is optionally substituted heteroC$_{9-13}$alkenyl. In some embodiments, R$^L$ is optionally substituted heteroC$_{9-12}$alkenyl. In some embodiments, R$^L$ is optionally substituted heteroC$_{9-11}$alkenyl. In some embodiments, R$^L$ is optionally substituted heteroC$_{9-10}$alkenyl.

In some embodiments, R$^L$ is optionally substituted heteroC$_{10-50}$alkenyl. In some embodiments, R$^L$ is optionally substituted heteroC$_{10-40}$alkenyl. In some embodiments, R$^L$ is optionally substituted heteroC$_{10-30}$alkenyl. In some embodiments, R$^L$ is optionally substituted heteroC$_{10-20}$alkenyl. In some embodiments, R$^L$ is optionally substituted heteroC$_{10-19}$alkenyl. In some embodiments, R$^L$ is optionally substituted heteroC$_{10-18}$alkenyl. In some embodiments, R$^L$ is optionally substituted heteroC$_{10-17}$alkenyl. In some embodiments, R$^L$ is optionally substituted heteroC$_{10-16}$alkenyl. In some embodiments, R$^L$ is optionally substituted heteroC$_{10-15}$alkenyl. In some embodiments, R$^L$ is optionally substituted heteroC$_{10-14}$alkenyl. In some embodiments, R$^L$ is optionally substituted heteroC$_{10-13}$alkenyl. In some embodiments, R$^L$ is optionally substituted heteroC$_{10-12}$alkenyl. In some embodiments, R$^L$ is optionally substituted heteroC$_{10-11}$alkenyl.

In some embodiments, R$^L$ is optionally substituted heteroC$_{11-50}$alkenyl. In some embodiments, R$^L$ is optionally substituted heteroC$_{11-40}$alkenyl. In some embodiments, R$^L$ is optionally substituted heteroC$_{11-30}$alkenyl. In some embodiments, R$^L$ is optionally substituted heteroC$_{11-20}$alkenyl. In some embodiments, R$^L$ is optionally substituted heteroC$_{11-19}$alkenyl. In some embodiments, R$^L$ is optionally substituted heteroC$_{11-18}$alkenyl. In some embodiments, R$^L$ is optionally substituted heteroC$_{11-17}$alkenyl. In some embodiments, R$^L$ is optionally substituted heteroC$_{11-16}$alkenyl. In some embodiments, R$^L$ is optionally substituted heteroC$_{11-15}$alkenyl. In some embodiments, R$^L$ is optionally substituted heteroC$_{11-14}$alkenyl. In some embodiments, R$^L$ is optionally substituted heteroC$_{11-13}$alkenyl. In some embodiments, R$^L$ is optionally substituted heteroC$_{11-12}$alkenyl.

In some embodiments, R$^L$ is optionally substituted heteroC$_{12-50}$alkenyl. In some embodiments, R$^L$ is optionally substituted heteroC$_{12-40}$alkenyl. In some embodiments, R$^L$ is optionally substituted heteroC$_{12-30}$alkenyl. In some embodiments, R$^L$ is optionally substituted heteroC$_{12-20}$alkenyl. In some embodiments, R$^L$ is optionally substituted heteroC$_{12-19}$alkenyl. In some embodiments, R$^L$ is optionally substituted heteroC$_{12-18}$alkenyl. In some embodiments, R$^L$ is optionally substituted heteroC$_{12-17}$alkenyl. In some embodiments, R$^L$ is optionally substituted heteroC$_{12-16}$alkenyl. In some embodiments, R$^L$ is optionally substituted heteroC$_{12-15}$alkenyl. In some embodiments, R$^L$ is optionally substituted heteroC$_{12-14}$alkenyl. In some embodiments, R$^L$ is optionally substituted heteroC$_{12-13}$alkenyl.

In some embodiments, R$^L$ is optionally substituted heteroC$_6$alkenyl. In some embodiments, R$^L$ is optionally substituted heteroC$_7$alkenyl. In some embodiments, R$^L$ is optionally substituted heteroC$_8$alkenyl. In some embodiments, R$^L$ is optionally substituted heteroC$_9$alkenyl. In some embodiments, R$^L$ is optionally substituted heteroC$_{10}$alkenyl. In some embodiments, R$^L$ is optionally substituted heteroC$_{11}$alkenyl. In some embodiments, R$^L$ is optionally substituted heteroC$_{12}$alkenyl. In some embodiments, R$^L$ is optionally substituted heteroC$_{13}$alkenyl. In some embodiments, R$^L$ is optionally substituted heteroC$_{14}$alkenyl. In some embodiments, R$^L$ is optionally substituted heteroC$_{15}$alkenyl. In some embodiments, R$^L$ is optionally substituted heteroC$_{16}$alkenyl. In some embodiments, R$^L$ is optionally substituted heteroC$_{17}$alkenyl. In some embodiments, R$^L$ is optionally substituted heteroC$_{18}$alkenyl. In some embodiments, R$^L$ is optionally substituted heteroC$_{19}$alkenyl. In some embodiments, R$^L$ is optionally substituted heteroC$_{20}$alkenyl.

In some embodiments, for example, in any of the above embodiments, R$^L$ is a substituted heteroalkenyl group. In some embodiments, R$^L$ is an unsubstituted heteroalkenyl group. In some embodiments, R$^L$ is an optionally substituted straight-chain heteroalkenyl group. In some embodiments, R$^L$ is a substituted straight-chain heteroalkenyl group. In some embodiments, R$^L$ is an unsubstituted straight-chain heteroalkenyl group. In some embodiments, R$^L$ is an optionally substituted branched heteroalkenyl group. In some embodiments, R$^L$ is a substituted branched heteroalkenyl group. In some embodiments, R$^L$ is an unsubstituted branched heteroalkenyl group.

In some embodiments, R$^L$ is optionally substituted heteroC$_{2-50}$alkynyl. In some embodiments, R$^L$ is optionally substituted heteroC$_{2-40}$alkynyl. In some embodiments, R$^L$ is optionally substituted heteroC$_{2-30}$alkynyl. In some embodiments, $R^L$ is optionally substituted heteroC$_{2-20}$alkynyl. In some embodiments, $R^L$ is optionally substituted heteroC$_{2-19}$alkynyl. In some embodiments, $R^L$ is optionally substituted heteroC$_{2-18}$alkynyl. In some embodiments, $R^L$ is optionally substituted heteroC$_{2-17}$alkynyl. In some embodiments, $R^L$ is optionally substituted heteroC$_{2-16}$alkynyl. In some embodiments, $R^L$ is optionally substituted heteroC$_{2-15}$alkynyl. In some embodiments, $R^L$ is optionally substituted heteroC$_{2-14}$alkynyl. In some embodiments, $R^L$ is optionally substituted heteroC$_{2-13}$alkynyl. In some embodiments, $R^L$ is optionally substituted heteroC$_{2-12}$alkynyl. In some embodiments, $R^L$ is optionally substituted heteroC$_{2-11}$alkynyl. In some embodiments, $R^L$ is optionally substituted heteroC$_{2-10}$alkynyl. In some embodiments, $R^L$ is optionally substituted heteroC$_{2-9}$alkynyl. In some embodiments, $R^L$ is optionally substituted heteroC$_{2-8}$alkynyl. In some embodiments, $R^L$ is optionally substituted heteroC$_{2-7}$alkynyl. In some embodiments, $R^L$ is optionally substituted heteroC$_{2-6}$alkynyl.

In some embodiments, $R^L$ is optionally substituted heteroC$_{4-50}$alkynyl. In some embodiments, $R^L$ is optionally substituted heteroC$_{4-40}$alkynyl. In some embodiments, $R^L$ is optionally substituted heteroC$_{4-30}$alkynyl. In some embodiments, $R^L$ is optionally substituted heteroC$_{4-20}$alkynyl. In some embodiments, $R^L$ is optionally substituted heteroC$_{4-19}$alkynyl. In some embodiments, $R^L$ is optionally substituted heteroC$_{4-18}$alkynyl. In some embodiments, $R^L$ is optionally substituted heteroC$_{4-17}$alkynyl. In some embodiments, $R^L$ is optionally substituted heteroC$_{4-16}$alkynyl. In some embodiments, $R^L$ is optionally substituted heteroC$_{4-15}$alkynyl. In some embodiments, $R^L$ is optionally substituted heteroC$_{4-14}$alkynyl. In some embodiments, $R^L$ is optionally substituted heteroC$_{4-13}$alkynyl. In some embodiments, $R^L$ is optionally substituted heteroC$_{4-12}$alkynyl. In some embodiments, $R^L$ is optionally substituted heteroC$_{4-11}$alkynyl. In some embodiments, $R^L$ is optionally substituted heteroC$_{4-10}$alkynyl. In some embodiments, $R^L$ is optionally substituted heteroC$_{4-9}$alkynyl. In some embodiments, $R^L$ is optionally substituted heteroC$_{4-8}$alkynyl. In some embodiments, $R^L$ is optionally substituted heteroC$_{4-7}$alkynyl. In some embodiments, $R^L$ is optionally substituted heteroC$_{4-6}$alkynyl.

In some embodiments, $R^L$ is optionally substituted heteroC$_{6-50}$alkynyl. In some embodiments, $R^L$ is optionally substituted heteroC$_{6-40}$alkynyl. In some embodiments, $R^L$ is optionally substituted heteroC$_{6-30}$alkynyl. In some embodiments, $R^L$ is optionally substituted heteroC$_{6-20}$alkynyl. In some embodiments, $R^L$ is optionally substituted heteroC$_{6-19}$alkynyl. In some embodiments, $R^L$ is optionally substituted heteroC$_{6-18}$alkynyl. In some embodiments, $R^L$ is optionally substituted heteroC$_{6-17}$alkynyl. In some embodiments, $R^L$ is optionally substituted heteroC$_{6-16}$alkynyl. In some embodiments, $R^L$ is optionally substituted heteroC$_{6-15}$alkynyl. In some embodiments, $R^L$ is optionally substituted heteroC$_{6-14}$alkynyl. In some embodiments, $R^L$ is optionally substituted heteroC$_{6-13}$alkynyl. In some embodiments, $R^L$ is optionally substituted heteroC$_{6-12}$alkynyl. In some embodiments, $R^L$ is optionally substituted heteroC$_{6-11}$alkynyl. In some embodiments, $R^L$ is optionally substituted heteroC$_{6-10}$alkynyl. In some embodiments, $R^L$ is optionally substituted heteroC$_{6-9}$alkynyl. In some embodiments, $R^L$ is optionally substituted heteroC$_{6-8}$alkynyl. In some embodiments, $R^L$ is optionally substituted heteroC$_{6-7}$alkynyl.

In some embodiments, $R^L$ is optionally substituted heteroC$_{8-50}$alkynyl. In some embodiments, $R^L$ is optionally substituted heteroC$_{8-40}$alkynyl. In some embodiments, $R^L$ is optionally substituted heteroC$_{8-30}$alkynyl. In some embodiments, $R^L$ is optionally substituted heteroC$_{8-20}$alkynyl. In some embodiments, $R^L$ is optionally substituted heteroC$_{8-19}$alkynyl. In some embodiments, $R^L$ is optionally substituted heteroC$_{8-18}$alkynyl. In some embodiments, $R^L$ is optionally substituted heteroC$_{8-17}$alkynyl. In some embodiments, $R^L$ is optionally substituted heteroC$_{8-16}$alkynyl. In some embodiments, $R^L$ is optionally substituted heteroC$_{8-15}$alkynyl. In some embodiments, $R^L$ is optionally substituted heteroC$_{8-14}$alkynyl. In some embodiments, $R^L$ is optionally substituted heteroC$_{8-13}$alkynyl. In some embodiments, $R^L$ is optionally substituted heteroC$_{8-12}$alkynyl. In some embodiments, $R^L$ is optionally substituted heteroC$_{8-11}$alkynyl. In some embodiments, $R^L$ is optionally substituted heteroC$_{8-10}$alkynyl. In some embodiments, $R^L$ is optionally substituted heteroC$_{8-9}$alkynyl.

In some embodiments, $R^L$ is optionally substituted heteroC$_{9-50}$alkynyl. In some embodiments, $R^L$ is optionally substituted heteroC$_{9-40}$alkynyl. In some embodiments, $R^L$ is optionally substituted heteroC$_{9-30}$alkynyl. In some embodiments, $R^L$ is optionally substituted heteroC$_{9-20}$alkynyl. In some embodiments, $R^L$ is optionally substituted heteroC$_{9-19}$alkynyl. In some embodiments, $R^L$ is optionally substituted heteroC$_{9-18}$alkynyl. In some embodiments, $R^L$ is optionally substituted heteroC$_{9-17}$alkynyl. In some embodiments, $R^L$ is optionally substituted heteroC$_{9-16}$alkynyl. In some embodiments, $R^L$ is optionally substituted heteroC$_{9-15}$alkynyl. In some embodiments, $R^L$ is optionally substituted heteroC$_{9-14}$alkynyl. In some embodiments, $R^L$ is optionally substituted heteroC$_{9-13}$alkynyl. In some embodiments, $R^L$ is optionally substituted heteroC$_{9-12}$alkynyl. In some embodiments, $R^L$ is optionally substituted heteroC$_{9-11}$alkynyl. In some embodiments, $R^L$ is optionally substituted heteroC$_{9-10}$alkynyl.

In some embodiments, $R^L$ is optionally substituted heteroC$_{10-50}$alkynyl. In some embodiments, $R^L$ is optionally substituted heteroC$_{10-40}$alkynyl. In some embodiments, $R^L$ is optionally substituted heteroC$_{10-30}$alkynyl. In some embodiments, $R^L$ is optionally substituted heteroC$_{10-20}$alkynyl. In some embodiments, $R^L$ is optionally substituted heteroC$_{10-19}$alkynyl. In some embodiments, $R^L$ is optionally substituted heteroC$_{10-18}$alkynyl. In some embodiments, $R^L$ is optionally substituted heteroC$_{10-17}$alkynyl. In some embodiments, $R^L$ is optionally substituted heteroC$_{10-16}$alkynyl. In some embodiments, $R^L$ is optionally substituted heteroC$_{10-15}$alkynyl. In some embodiments, $R^L$ is optionally substituted heteroC$_{10-14}$alkynyl. In some embodiments, $R^L$ is optionally substituted heteroC$_{10-13}$alkynyl. In some embodiments, $R^L$ is optionally substituted heteroC$_{10-12}$alkynyl. In some embodiments, $R^L$ is optionally substituted heteroC$_{10-11}$alkynyl.

In some embodiments, $R^L$ is optionally substituted heteroC$_{11-50}$alkynyl. In some embodiments, $R^L$ is optionally substituted heteroC$_{11-40}$alkynyl. In some embodiments, $R^L$ is optionally substituted heteroC$_{11-30}$alkynyl. In some embodiments, $R^L$ is optionally substituted heteroC$_{11-20}$alkynyl. In some embodiments, $R^L$ is optionally substituted heteroC$_{11-19}$alkynyl. In some embodiments, $R^L$ is optionally substituted heteroC$_{11-18}$alkynyl. In some embodiments, $R^L$ is optionally substituted heteroC$_{11-17}$alkynyl. In some embodiments, $R^L$ is optionally substituted heteroC$_{11-16}$alkynyl. In some embodiments, $R^L$ is optionally substituted heteroC$_{11-15}$alkynyl. In some embodiments, $R^L$ is optionally substituted heteroC$_{11-14}$alkynyl. In some embodiments, $R^L$ is optionally substituted heteroC$_{11-13}$alkynyl. In some embodiments, $R^L$ is optionally substituted heteroC$_{11-12}$alkynyl.

In some embodiments, $R^L$ is optionally substituted heteroC$_{12-50}$alkynyl. In some embodiments, $R^L$ is optionally substituted heteroC$_{12-40}$alkynyl. In some embodiments, $R^L$ is optionally substituted heteroC$_{12-30}$alkynyl. In some embodiments, $R^L$ is optionally substituted heteroC$_{12-20}$alkynyl. In some embodiments, $R^L$ is optionally substituted heteroC$_{12-19}$alkynyl. In some embodiments, $R^L$ is optionally substituted heteroC$_{12-18}$alkynyl. In some embodiments, $R^L$ is optionally substituted heteroC$_{12-17}$alkynyl. In some embodiments, $R^L$ is optionally substituted heteroC$_{12-16}$alkynyl. In some embodiments, $R^L$ is optionally substituted heteroC$_{12-15}$alkynyl. In some embodiments, $R^L$ is optionally substituted heteroC$_{12-14}$alkynyl. In some embodiments, $R^L$ is optionally substituted heteroC$_{12-13}$alkynyl.

In some embodiments, $R^L$ is optionally substituted heteroC$_6$alkynyl. In some embodiments, $R^L$ is optionally substituted heteroC$_7$alkynyl. In some embodiments, $R^L$ is optionally substituted heteroC$_8$alkynyl. In some embodiments, $R^L$ is optionally substituted heteroC$_9$alkynyl. In some embodiments, $R^L$ is optionally substituted heteroC$_{10}$alkynyl. In some embodiments, $R^L$ is optionally substituted heteroC$_{11}$alkynyl. In some embodiments, $R^L$ is optionally substituted heteroC$_{12}$alkynyl. In some embodiments, $R^L$ is optionally substituted heteroC$_{13}$alkynyl. In some embodiments, $R^L$ is optionally substituted heteroC$_{14}$alkynyl. In some embodiments, $R^L$ is optionally substituted heteroC$_{15}$alkynyl. In some embodiments, $R^L$ is optionally substituted heteroC$_{16}$alkynyl. In some embodiments, $R^L$ is optionally substituted heteroC$_{17}$alkynyl. In some embodiments, $R^L$ is optionally substituted heteroC$_{18}$alkynyl. In some embodiments, $R^L$ is optionally substituted heteroC$_{19}$alkynyl. In some embodiments, $R^L$ is optionally substituted heteroC$_{20}$alkynyl.

In some embodiments, for example, in any of the above embodiments, $R^L$ is a substituted heteroalkynyl group. In some embodiments, $R^L$ is an unsubstituted heteroalkynyl group. In some embodiments, $R^L$ is an optionally substituted straight-chain heteroalkynyl group. In some embodiments, $R^L$ is a substituted straight-chain heteroalkynyl group. In some embodiments, $R^L$ is an unsubstituted straight-chain heteroalkynyl group. In some embodiments, $R^L$ is an optionally substituted branched heteroalkynyl group. In some embodiments, $R^L$ is a substituted branched heteroalkynyl group. In some embodiments, $R^L$ is an unsubstituted branched heteroalkynyl group.

In some embodiments, $R^L$ is a polymer. As used herein, a "polymer", in some embodiments, refers to a compound comprised of at least 3 (e.g., at least 10, 20, 30, 40, 50, 60, 70, 80, 90, 100, etc.) repeating covalently bound structural units. The polymer is in certain embodiments biocompatible (i.e., non-toxic). Exemplary polymers include, but are not limited to, cellulose polymers (e.g., hydroxyethylcellulose, ethylcellulose, carboxymethylcellulose, methylc cellulose, hydroxypropylmethylcellulose (HPMC)), dextran polymers, polymaleic acid polymers, poly(acrylic acid) polymers, poly(vinylalcohol) polymers, polyvinylpyrrolidone (PVP) polymers, and polyethyleneglycol (PEG) polymers, and combinations thereof.

In some embodiments, $R^L$ is a lipophilic, hydrophobic and/or non-polar group. In some embodiments, $R^L$ is a lipophilic group. In some embodiments, $R^L$ is a hydrophobic group. In some embodiments, $R^L$ is a non-polar group.

In some embodiments, when an $R^L$ group is depicted as bisecting a carbon-carbon bond, e.g., of the formula (i), it is understood that $R^L$ may be bonded to either carbon.

In some embodiments, at least one instance of $R^Q$, $R^2$, $R^6$, or $R^7$ is a group of the formula (i), (ii), or (iii). In some embodiments, at least one instance of $R^6$ or $R^7$ of $R^1$ is a group of formula (i), (ii) or (iii). In some embodiments, at least one instance of $R^6$ or $R^7$ of $R^1$ is a group of formula (i). In some embodiments, at least one instance of $R^6$ or $R^7$ of $R^1$ is a group of formula (i-a). In some embodiments, at least one instance of $R^6$ or $R^7$ of $R^1$ is a group of formula (i-al). In some embodiments, at least one instance of $R^6$ or $R^7$ of $R^1$ is a group of formula (i-b). In some embodiments, at least one instance of $R^6$ or $R^7$ of $R^1$ is a group of formula (ii). In some embodiments, at least one instance of $R^6$ or $R^7$ of $R^1$ is a group of formula (iii).

In some embodiments, the compound (i.e., cationic lipid) of formula I is a compound according to formula II:

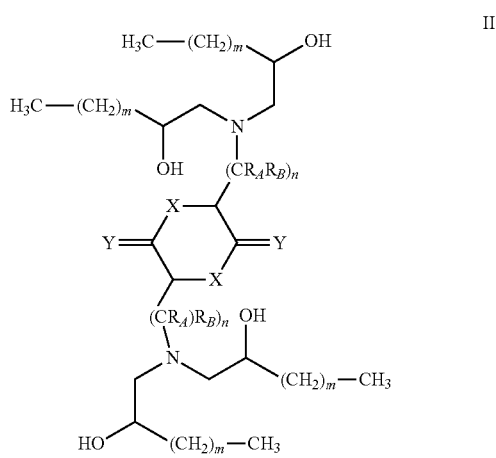

or a pharmaceutically acceptable salt thereof,
wherein:
each m independently is 1 to 19;
each n is independently is 1 to 6;
each X independently is O or S;
each Y independently is O or S;
each $R_A$ is independently hydrogen, optionally substituted C$_{1-50}$ alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen, wherein each alkyl, alkenyl, alkynyl, carbocyclyl, heterocyclyl, aryl, and heteroaryl is independently substituted with 0, 1, 2, 3, 4, or 5 Rdd groups, and each $R_B$ is independently hydrogen, optionally substituted C$_{1-50}$ alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen, wherein each alkyl, alkenyl, alkynyl, carbocyclyl, heterocyclyl, aryl, and heteroaryl is independently substituted with 0, 1, 2, 3, 4, or 5 Rdd groups.

In some embodiments, each n independently is 2 to 6. In some embodiments, each n independently is 3 to 5. In some embodiments, each n independently is 3 or 4. In some embodiments, each n is the same. In some embodiments, each n is 2. In some embodiments, each n is 3. In some embodiments, each n is 4. In some embodiments, each n is 5. In some embodiments, each n is 6.

In some embodiments, each m independently is 1 to 17. In some embodiments, each m independently is 3 to 15. In some embodiments, each m independently is 5 to 13. In some embodiments, each m independently is 7 to 11. In some embodiments, each m independently is 8 to 10. In some embodiments, each m is the same. In some embodiments, each m is 7. In some embodiments, each m is 8. In some embodiments, each m is 9. In some embodiments, each m is 10. In some embodiments, each m is 11.

In some embodiments, each X is the same. In some embodiments, each X is O. In some embodiments, each X is S. In some embodiments, one X is O and one X is S.

In some embodiments, each Y is the same. In some embodiments, each Y is O. In some embodiments, each Y is S. In some embodiments, one Y is O and one Y is S.

In some embodiments, each X is the same and each Y is the same. In some embodiments, each X is O and each Y is O. In some embodiments, each X is S and each Y is S.

In some embodiments, $R_A$ is hydrogen. In some embodiments, $R_A$ is optionally substituted C2-50 alkenyl. In some embodiments, $R_A$ is optionally substituted C2-50 alkynyl. In some embodiments, $R_A$ is optionally substituted C3-10 carbocyclyl. In some embodiments, $R_A$ is optionally substituted 3-14 membered heterocyclyl. In some embodiments, $R_A$ is optionally substituted C6-14 aryl. In some embodiments, $R_A$ is optionally substituted 5-14 membered heteroaryl. In some embodiments, $R_A$ is halogen.

In certain embodiments, $R_A$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl. In certain embodiments, at least one instance of $R_A$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl. In certain embodiments, $R_A$ is methyl.

In certain embodiments, $R_A$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl. In certain embodiments, at least one instance of $R_A$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl.

In certain embodiments, $R_A$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl. In certain embodiments, at least one instance of $R_A$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl.

In certain embodiments, $R_A$ is optionally substituted carbocyclyl, e.g., optionally substituted $C_{3-10}$ carbocyclyl, optionally substituted $C_{5-8}$ carbocyclyl, optionally substituted $C_{5-6}$ carbocyclyl, optionally substituted $C_5$ carbocyclyl, or optionally substituted $C_6$ carbocyclyl. In certain embodiments, at least one instance of $R_A$ is optionally substituted carbocyclyl, e.g., optionally substituted $C_{3-10}$ carbocyclyl, optionally substituted $C_{5-8}$ carbocyclyl, optionally substituted $C_{5-6}$ carbocyclyl, optionally substituted $C_5$ carbocyclyl, or optionally substituted $C_6$ carbocyclyl.

In some embodiments, $R_A$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5-membered heterocyclyl, or optionally substituted 6-membered heterocyclyl. In certain embodiments, at least one instance of $R_A$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5-membered heterocyclyl, or optionally substituted 6-membered heterocyclyl.

In some embodiments, $R_A$ is optionally substituted aryl. In some embodiments, $R_A$ is optionally substituted phenyl. In some embodiments, $R_A$ is phenyl. In some embodiments, $R_A$ is substituted phenyl. In certain embodiments, at least one instance of $R_A$ is optionally substituted aryl, e.g., optionally substituted phenyl.

In some embodiments, $R_A$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl. In certain embodiments, at least one instance of $R_A$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl.

In some embodiments, $R_A$ is halogen. In some embodiments, $R_A$ is —F. In some embodiments, $R_A$ is —Cl. In some embodiments, $R_A$ is —Br. In some embodiments, $R_A$ is —I.

In some embodiments, $R_B$ is hydrogen. In some embodiments, $R_B$ is optionally substituted $C_{1-50}$ alkyl. In some embodiments, $R_B$ is optionally substituted C2-50 alkenyl. In some embodiments, $R_B$ is optionally substituted C2-50 alkynyl. In some embodiments, $R_B$ is optionally substituted C3-10 carbocyclyl. In some embodiments, $R_B$ is optionally substituted 3-14 membered heterocyclyl. In some embodiments, $R_B$ is optionally substituted C6-14 aryl. In some embodiments, $R_B$ is optionally substituted 5-14 membered heteroaryl. In some embodiments, $R_B$ is halogen.

In certain embodiments, $R_B$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl. In certain embodiments, at least one instance of $R_B$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl. In certain embodiments, $R_B$ is methyl.

In certain embodiments, $R_B$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl. In certain embodiments, at least one instance of $R_B$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl.

In certain embodiments, $R_B$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl. In certain embodiments, at least one instance of $R_B$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl.

In certain embodiments, $R_B$ is optionally substituted carbocyclyl, e.g., optionally substituted $C_{3-10}$ carbocyclyl, optionally substituted $C_{5-8}$ carbocyclyl, optionally substituted $C_{5-6}$ carbocyclyl, optionally substituted $C_5$ carbocyclyl, or optionally substituted $C_6$ carbocyclyl. In certain embodiments, at least one instance of $R_B$ is optionally substituted carbocyclyl, e.g., optionally substituted $C_{3-10}$ carbocyclyl, optionally substituted $C_{5-8}$ carbocyclyl, optionally substituted $C_{5-6}$ carbocyclyl, optionally substituted $C_5$ carbocyclyl, or optionally substituted $C_6$ carbocyclyl.

In some embodiments, $R_B$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5-membered heterocyclyl, or optionally substituted 6-membered heterocyclyl. In certain embodiments, at least one instance of $R_B$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5-membered heterocyclyl, or optionally substituted 6-membered heterocyclyl.

In some embodiments, $R_B$ is optionally substituted aryl. In some embodiments, $R_B$ is optionally substituted phenyl. In some embodiments, $R_B$ is phenyl. In some embodiments, $R_B$ is substituted phenyl. In certain embodiments, at least one instance of $R_B$ is optionally substituted aryl, e.g., optionally substituted phenyl.

In some embodiments, $R_B$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl. In certain embodiments, at least one instance of $R_B$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl.

In some embodiments, $R_B$ is halogen. In some embodiments, $R_B$ is —F. In some embodiments, $R_B$ is —Cl. In some embodiments, $R_B$ is —Br. In some embodiments, $R_B$ is —I.

In some embodiments, at least one $R_A$ is optionally substituted $C_{1-50}$ alkyl. In some embodiments, at least one $R_A$ and one $R_B$ are optionally substituted $C_{1-50}$ alkyl. In some embodiments, at least one $R_A$ and one $R_B$ are optionally substituted $C_{1-50}$ alkyl, where the $R_A$ and $R_B$ are attached to the same carbon. In some embodiments, at least one $R_A$ is methyl. In some embodiments, at least one $R_A$ and one $R_B$ are methyl. In some embodiments, at least one $R_A$ and one $R_B$ are methyl, where the $R_A$ and $R_B$ are attached to the same carbon.

In some embodiments, a compound of formula II is a compound of formula II-a:

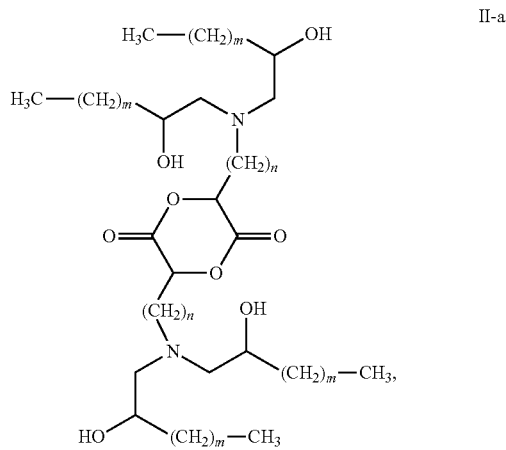

or a pharmaceutically acceptable salt thereof, wherein m and n are as defined above and described herein.

In some embodiments, a compound of formula II is a compound of formula II-a wherein each n independently is 2 to 6 and each m independently is 3 to 15. In some embodiments, a compound of formula II is a compound of formula II-a wherein each n independently is 3 to 5 and each m independently is 5 to 13. In some embodiments, a compound of formula II is a compound of formula II-a wherein each n independently is 3 or 4 and each m independently is 7 to 11. In some embodiments, a compound of formula II is a compound of formula II-a wherein each n is the same and is 3 or 4, and each m is the same and is 7 to 11.

In some embodiments, a compound of formula II is a compound of formula III:

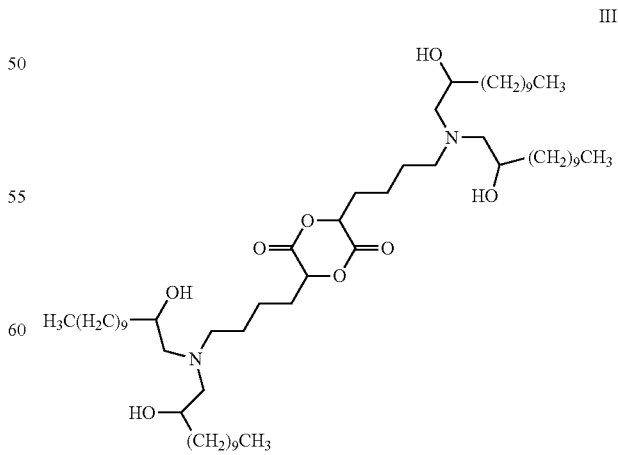

or a pharmaceutically acceptable salt thereof.

In some embodiments, a compound of formula II is a compound of formula IV:

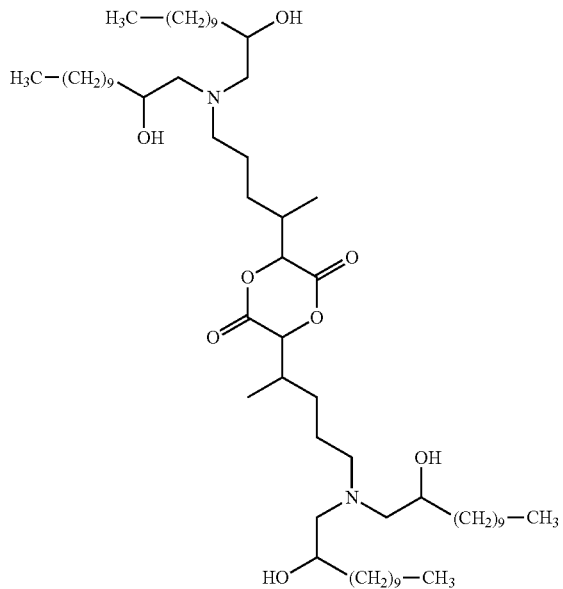

or a pharmaceutically acceptable salt thereof.

In some embodiments, a compound of formula II is a compound of formula V:

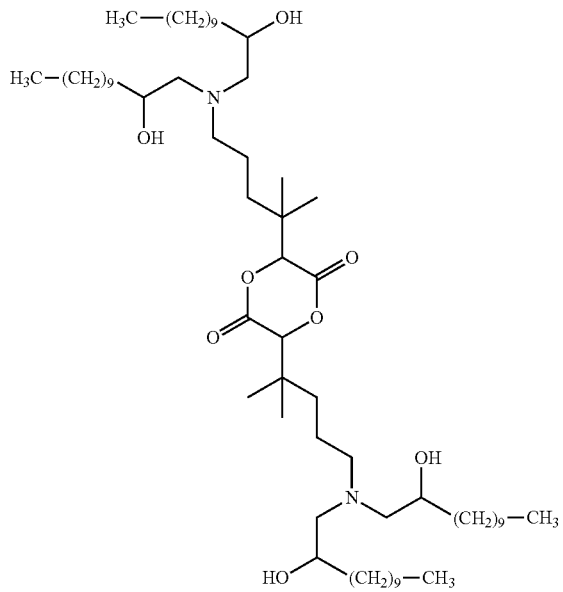

or a pharmaceutically acceptable salt thereof.

Liposomes for the Delivery of Agents, Such as mRNA

Among other things, the present invention provides composition comprising a biodegradable compound described herein for delivery of therapeutic agents. In some embodiments, a composition provided is a lipid based nanoparticle, such as a liposome. As used herein, the term "liposome" refers to any lamellar, multilamellar, or solid lipid nanoparticle vesicle. Typically, a liposome as used herein can be formed by mixing one or more lipids or by mixing one or more lipids and polymer(s). Thus, the term "liposome" as used herein encompasses both lipid and polymer based nanoparticles. In particular, a liposome according to the present invention incorporates a biodegradable compound described herein as a cationic lipid. As a non-limiting example, a liposome according to the present invention is a compound of formula III i.e., 3,6-bis(4-(bis(2-hydroxydodecyl)amino)butyl)-1,4-dioxane-2,5-dione. A suitable liposome may also contain second or additional cationic lipids, helper lipids (e.g., non-cationic lipids and/or cholesterol-based lipids), PEG-modified lipids, and/or polymers.

In some embodiments, cationic lipid(s) (e.g., the compound of formula III) constitute(s) about 30-50% (e.g., about 30-45%, about 30-40%, about 35-50%, about 35-45%, or about 35-40%) of the liposome by molar ratio. In some embodiments, the cationic lipid (e.g., the compound of formula III) constitutes about 30%, about 35%, about 40%, about 45%, or about 50% of the liposome by molar ratio. In some embodiments, the liposome comprises a second lipid or additional cationic lipids.

Second or Additional Cationic Lipids

In some embodiments, liposomes may comprise a second or additional cationic lipid. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, C12-200 described at paragraph [00225]), WO 2012/170930 and WO 2013063468 each of which is incorporated herein by reference in its entirety. In certain embodiments, the compositions and methods of the invention employ a lipid nanoparticles comprising an ionizable (titratable) cationic lipid described in International Patent Application No. PCT/US2013/034602, filed Mar. 29, 2013, Publ. No. WO 2013/149140 (incorporated herein by reference), such as, e.g, (15Z, 18Z)—N,N-dimethyl-6-(9Z, 12Z)-octadeca-9,12-dien-1-yl)tetracosa-15,18-dien-1-amine (HGT5000), (15Z, 18Z)—N,N-dimethyl-6-((9Z, 12Z)-octadeca-9,12-dien-1-yl)tetracosa-4,15,18-trien-1-amine (HGT5001), and (15Z, 18Z)—N,N-dimethyl-6-((9Z, 12Z)-octadeca-9,12-dien-1-yl)tetracosa-5, 15,18-trien-1-amine (HGT5002).

In some embodiments, the second or additional cationic lipid is cKK-E12 (3,6-bis(4-(bis(2-hydroxydodecyl)amino) butyl)piperazine-2,5-dione) or derivatives thereof, as described in international patent publications WO 2013/063468 incorporated herein by reference in its entirety.

In some embodiments, the second or additional cationic lipid N-[1-(2,3-dioleyloxy)propyl]-N,N,N-trimethylammonium chloride or "DOTMA" is used. (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido) ethyl]-N,N-dimethyl-l-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9', 1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, the second or additional cationic lipid may be chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)—N,N-dimethyl-2,2-di((9Z,12Z)-octadeca-9,12-dienyl)tetrahydro-3aH-cyclopenta[d][1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (international patent publication WO/2013/149140, the teachings of which are incorporated herein by reference in their entirety) or HGT5001 (cis or trans) (WO/2013/149140), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, The percentage of cholesterol-based lipid in the lipid nanoparticle may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

In some embodiments, particularly useful exchangeable lipids are PEG-ceramides having shorter acyl chains (e.g., $C_{14}$ or $C_{18}$). The PEG-modified phospholipid and derivatized lipids of the present invention may comprise a molar ratio from about 0% to about 15%, about 0.5% to about 15%, about 1% to about 15%, about 4% to about 10%, or about 2% of the total lipid present in the liposome.

According to various embodiments, the selection of second or additional cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly. In some embodiments, the percentage of PEG-modified lipid in a liposome may be greater than 1%, greater than 2%, greater than 5%, greater than 10%, or greater than 15%.

Polymers

In some embodiments, a suitable liposome according to the present invention further includes a polymer, in combination with one or more cationic lipids as described and, in some embodiments, other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDA, e.g., 25 kDa branched PEI (Sigma #408727).

Therapeutic Agents

The present invention may be used to delivery any therapeutic agents. Specifically, any therapeutic agents to be administered to a subject may be delivered using the complexes, picoparticles, nanoparticles, microparticles, micelles, or liposomes, described herein. The agent may be an organic molecule (e.g., a therapeutic agent, a drug), inorganic molecule, nucleic acid, protein, amino acid, peptide, polypeptide, polynucleotide, targeting agent, isotopically labeled organic or inorganic molecule, vaccine, immunological agent, etc. In certain embodiments of the present invention, the agent to be delivered may be a mixture of agents.

In certain embodiments, the therapeutic agents are organic molecules with pharmaceutical activity, e.g., a drug. In certain embodiments, the drug is an antibiotic, anti-viral agent, anesthetic, steroidal agent, anti-inflammatory agent, anti-neoplastic agent, anti-cancer agent, antigen, vaccine, antibody, decongestant, antihypertensive, sedative, birth control agent, progestational agent, anti-cholinergic, analgesic, anti-depressant, anti-psychotic, I3-adrenergic blocking agent, diuretic, cardiovascular active agent, vasoactive agent, non-steroidal anti-inflammatory agent, nutritional agent, etc.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine based materials.

Therapeutic and prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts.

Polynucleotides

The present invention may be used to deliver any polynucleotide. In certain embodiments, the polynucleotide is an interfering RNA (RNAi). The phenomenon of RNAi is discussed in greater detail, for example, in the following references: Elbashir et al., 2001, *Genes Dev.*, 15:188; Fire et al., 1998, *Nature*, 391:806; Tabara et al., 1999, *Cell*, 99:123; Hammond et al, *Nature*, 2000, 404:293; Zamore et al, 2000, *Cell*, 101:25; Chakraborty, 2007, *Curr. Drug Targets*, 8:469; and Morris and Rossi, 2006, *Gene Ther.*, 13:553. In certain embodiments, the polynucleotide is a dsRNA (double-stranded RNA). In certain embodiments, the polynucleotide is an siRNA (short interfering RNA). In certain embodiments, the polynucleotide is an shRNA (short hairpin RNA). In certain embodiments, the polynucleotide is an miRNA (micro RNA). Micro RNAs (miRNAs) are genomically encoded non-coding RNAs of about 21-23 nucleotides in length that help regulate gene expression, particularly during development. See, e.g., Bartel, 2004, *Cell*, 116:281; Novina and Sharp, 2004, *Nature*, 430:161; and U.S. Patent Publication 2005/0059005; also reviewed in Wang and Li, 2007, *Front. Biosci.*, 12:3975; and Zhao, 2007, *Trends Biochem. Sci.*, 32:189. In certain embodiments, the polynucleotide is an antisense RNA.

In certain embodiments, the polynucleotide may be provided as an antisense agent or RNA interference (RNAi). See, e.g., Fire et al., *Nature* 391:806-811, 1998. Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation. See, e.g., Crooke "Molecular mechanisms of action of antisense drugs" *Biochim. Biophys. Acta* 1489(1):31-44, 1999; Crooke "Evaluating the mechanism of action of antiproliferative antisense drugs" *Antisense Nucleic Acid Drug Dev.* 10(2): 123-126, discussion 127, 2000; Methods in Enzymology volumes 313-314, 1999. The binding may be by conventional base pair complementarity, or, for example, in the case of binding to DNA duplexes, through specific interactions in the major groove of the double helix (i.e., triple helix formation). See, e.g., Chan et al., *J. Mol. Med.* 75(4):267-282, 1997.

In some embodiments, dsRNA, siRNA, shRNA, miRNA, antisense RNA, and/or RNAi can be designed and/or predicted using one or more of a large number of available algorithms. To give but a few examples, the following resources can be utilized to design and/or predict polynucleotides: algorithms found at Alnylum Online, Dharmacon Online, OligoEngine Online, Molecula Online, Ambion Online, BioPredsi Online, RNAi Web Online, Chang Bioscience Online, Invitrogen Online, LentiWeb Online GenScript Online, Protocol Online; Reynolds et al., 2004, *Nat. Biotechnol.*, 22:326; Naito et al., 2006, *Nucleic Acids Res.*, 34:W448; Li et al., 2007, *RNA*, 13:1765; Yiu et al., 2005, *Bioinformatics*, 21:144; and Jia et al., 2006, *BMC Bioinformatics*, 7: 271.

The polynucleotides may be of any size or sequence, and they may be single- or double-stranded. In certain embodiments, the polynucleotide is greater than 100 base pairs long. In certain embodiments, the polynucleotide is greater than 1000 base pairs long and may be greater than 10,000 base pairs long. The polynucleotide may be provided by any means known in the art. In certain embodiments, the polynucleotide has been engineered using recombinant techniques. See, e.g., Ausubel et al., *Current Protocols in Molecular Biology* (John Wiley & Sons, Inc., New York, 1999); *Molecular Cloning: A Laboratory Manual,* 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry.

The polynucleotide may be modified by chemical or biological means. In certain embodiments, these modifications lead to increased stability of the polynucleotide. Modifications include methylation, phosphorylation, end-capping, etc.

mRNA

The present invention can be used to deliver any mRNA. mRNA is typically thought of as the type of RNA that carries information from DNA to the ribosome. The existence of mRNA is usually very brief and includes processing and translation, followed by degradation. Typically, in eukaryotic organisms, mRNA processing comprises the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA typically is translated by the ribosomes into a series of amino acids that make up a protein.

Any mRNA capable of being translated into one or more peptides (e.g., proteins) or peptide fragments is contemplated as within the scope of the present invention. In some embodiments, an mRNA encodes one or more naturally occurring peptides. In some embodiments, an mRNA encodes one or more modified or non-natural peptides.

In some embodiments an mRNA encodes an intracellular protein. In some embodiments, an mRNA encodes a cytosolic protein. In some embodiments, an mRNA encodes a protein associated with the actin cytoskeleton. In some embodiments, an mRNA encodes a protein associated with the plasma membrane. In some specific embodiments, an mRNA encodes a transmembrane protein. In some specific embodiments an mRNA encodes an ion channel protein. In some embodiments, an mRNA encodes a perinuclear protein. In some embodiments, an mRNA encodes a nuclear protein. In some specific embodiments, an mRNA encodes a transcription factor. In some embodiments, an mRNA encodes a chaperone protein. In some embodiments, an mRNA encodes an intracellular enzyme (e.g., mRNA encoding an enzyme associated with urea cycle or lysosomal storage metabolic disorders). In some embodiments, an mRNA encodes a protein involved in cellular metabolism, DNA repair, transcription and/or translation. In some embodiments, an mRNA encodes an extracellular protein. In some embodiments, an mRNA encodes a protein associated with the extracellular matrix. In some embodiments an mRNA encodes a secreted protein. In specific embodiments, an mRNA used in the composition and methods of the invention may be used to express functional proteins or enzymes that are excreted or secreted by one or more target cells into the surrounding extracellular fluid (e.g., mRNA encoding hormones and/or neurotransmitters).

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified mRNA

In some embodiments, mRNA according to the present invention may be synthesized as unmodified or modified mRNA. Typically, mRNAs are modified to enhance stability. Modifications of mRNA can include, for example, modifications of the nucleotides of the RNA. An modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylamino-methyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, wybutosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs (e.g., enzyme encoding mRNAs) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., enzyme encoding mRNAs) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-ara-cytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs (e.g., enzyme encoding mRNAs) may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallyl-cytidine 5'-triphosphate, 5-aminoallyl-uridine 5'-triphosphate, 5-bromocytidine 5'-triphosphate, 5-bromouridine 5'-triphosphate, 5-iodo-cytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Cap Structure

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., enzyme encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

In some embodiments, naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7GpppG$") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with $-OCH_3$.

Additional cap analogs include, but are not limited to, chemical structures selected from the group consisting of $m^7GpppG$, $m^7GpppA$, $m^7GpppC$; unmethylated cap analogs (e.g., GpppG); dimethylated cap analog (e.g., $m^{2,7}GpppG$), trimethylated cap analog (e.g., $m^{2,2,7}GpppG$), dimethylated symmetrical cap analogs (e.g., $m^7Gpppm^7G$), or anti reverse cap analogs (e.g., ARCA; $m^{7,2'Ome}GpppG$, $m^{72'd}GpppG$, $m^{7,3'Ome}GpppG$, $m^{7,3'd}GpppG$ and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("$m^7G$") linked via a triphosphate bridge to the 5'-end of the first transcribed nucleotide, resulting in $m^7G(5')ppp(5')N$, where N is any nucleoside. A preferred embodiment of a $m^7G$ cap utilized in embodiments of the invention is $m^7G(5')ppp(5')G$.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of $m^7G$ cap analogs are known in the art, many of which are commercially available. These include the $m^7GpppG$ described above, as well as the ARCA 3'-$OCH_3$ and 2'-$OCH_3$ cap analogs (Jemiclity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs (e.g., enzyme encoding mRNAs) include a 3' poly(A) tail structure. Typically, the length of the poly A tail can be at least about 10, 50, 100, 200, 300, 400 at least 500 nucleotides. In some embodiments, a poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

According to various embodiments, any size mRNA may be encapsulated by provided liposomes. In some embodiments, the provided liposomes may encapsulate mRNA of greater than about 0.5 kb, 1 kb, 1.5 kb, 2 kb, 2.5 kb, 3 kb, 3.5 kb, 4 kb, 4.5 kb, or 5 kb in length.

Liposomes

The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments, provided compositions comprise a liposome wherein an agent, such as a nucleic acid e.g., mRNA, is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more liposomes may have a different molar ratio of cationic lipid, neutral lipid, cholesterol and PEG-modified lipid used to create the liposome.

The process of incorporation of a desired therapeutic agent, such as a nucleic acid (e.g., mRNA), into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, a suitable liposome has a size of or less than about 500 nm, 450 nm, 400 nm, 350 nm, 300 nm, 250 nm, 200 nm, 150 nm, 125 nm, 110 nm, 100 nm, 95 nm, 90 nm, 85 nm, 80 nm, 75 nm, 70 nm, 65 nm, 60 nm, 55 nm, or 50 nm. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm).

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Pharmaceutical Compositions

To facilitate delivery of an agent, such as a nucleic acid e.g., mRNA, and/or expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated agents, such as a nucleic acid e.g., mRNA and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, and/or intranasal administration.

Alternately or additionally, liposomally encapsulated agents, such as a nucleic acid e.g., mRNA and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In some embodiments, provided liposomes and/or compositions are formulated such that they are suitable for extended-release of the agent, e.g., mRNA contained therein. Such extended-release compositions may be conveniently administered to a subject at extended dosing intervals. For example, in one embodiment, the compositions of the present invention are administered to a subject twice day, daily or every other day. In a preferred embodiment, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and liposomes which are formulated for depot administration (e.g., intramuscularly, subcutaneously, intravitreally) to either deliver or release a mRNA over extended periods of time. Preferably, the extended-release means employed are combined with modifications made to the mRNA to enhance stability.

Also contemplated herein are lyophilized pharmaceutical compositions comprising one or more of the liposomes disclosed herein and related methods for the use of such compositions as disclosed for example, in International Patent Application No. PCT/US2012/041663, filed Jun. 8, 2012, Publ. No. WO 2012/170889, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the agent, e.g., mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

According to various embodiments, the timing of expression of delivered agents, e.g., mRNAs, can be tuned to suit a particular medical need. In some embodiments, the expression of the protein encoded by delivered mRNA is detectable 1, 2, 3, 6, 12, 18, 24, 30, 36, 42, 48, 54, 60, 66, and/or 72 hours in serum or target tissues after a single administration of provided liposomes or compositions. In some embodiments, the expression of the protein encoded by the mRNA is detectable 1 day, 2 days, 3 days, 4 days, 5 days, 6 days, and/or 7 days in serum or target tissues after a single administration of provided liposomes or compositions. In some embodiments, the expression of the protein encoded by the mRNA is detectable 1 week, 2 weeks, 3 weeks, and/or 4 weeks in serum or target tissues after a single administration of provided liposomes or compositions. In some embodiments, the expression of the protein encoded by the mRNA is detectable after a month or longer after a single administration of provided liposomes or compositions.

EXAMPLES

While certain compounds, compositions and methods of the present invention have been described with specificity in accordance with certain embodiments, the following examples serve only to illustrate the compounds of the invention and are not intended to limit the same.

Example 1. Synthesis of Compounds of Formula I

A. Compounds of formula I, such as T23 (the compound of formula III), can be made according to the route shown in Scheme 1:

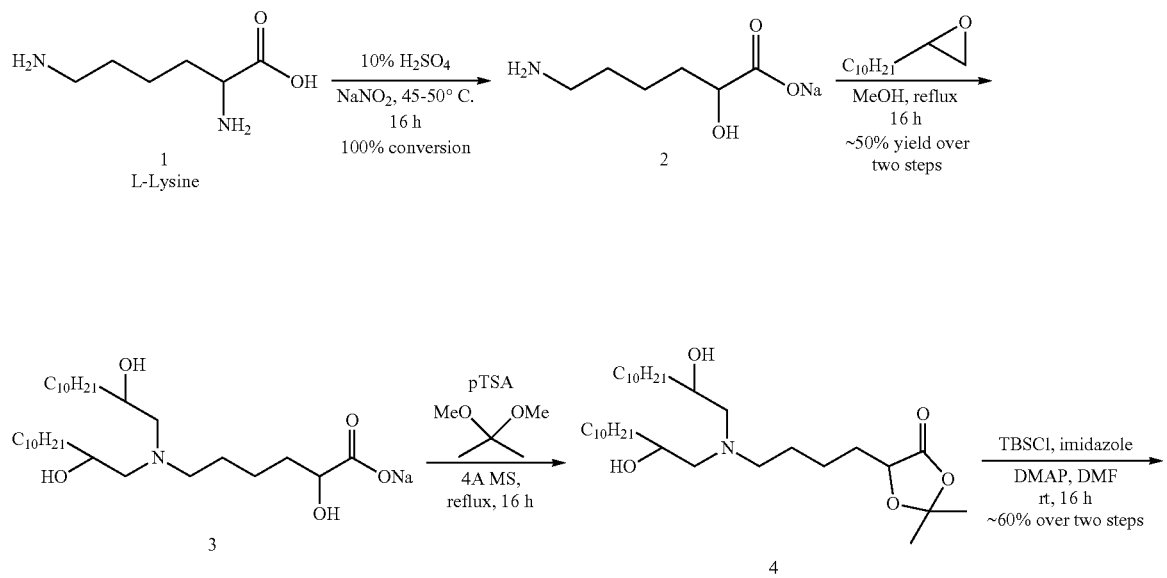

-continued
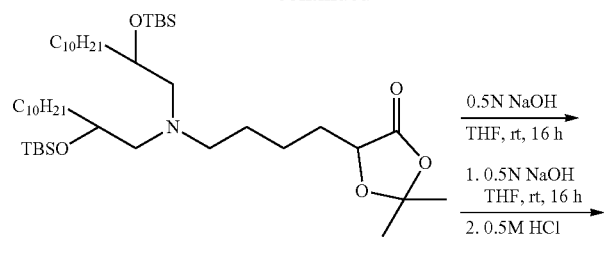
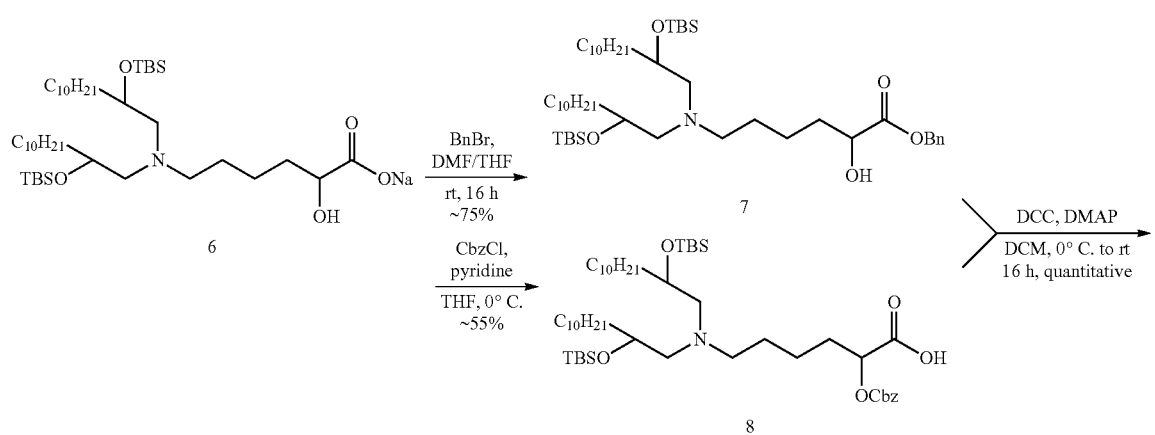
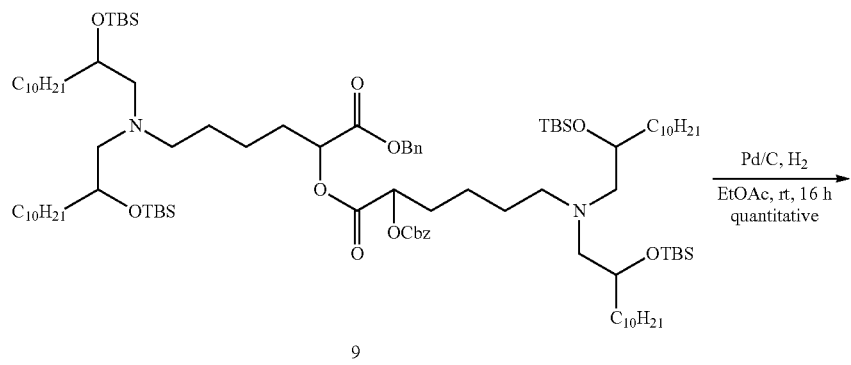
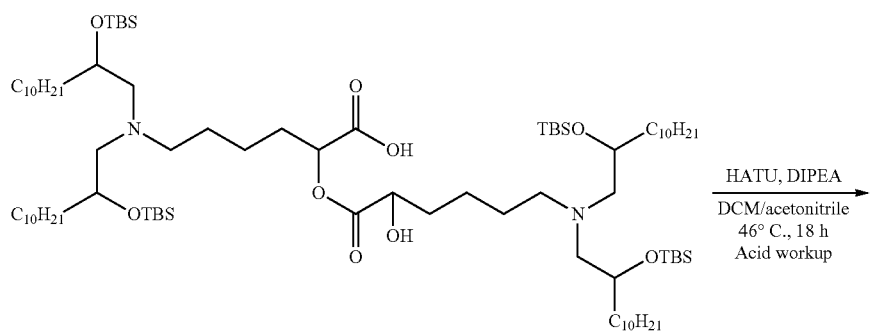

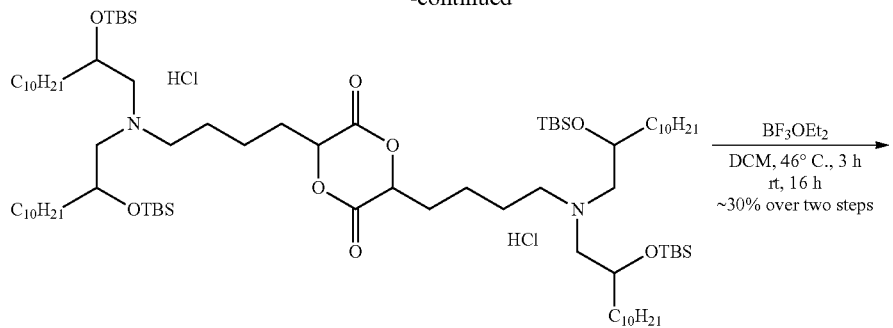

11

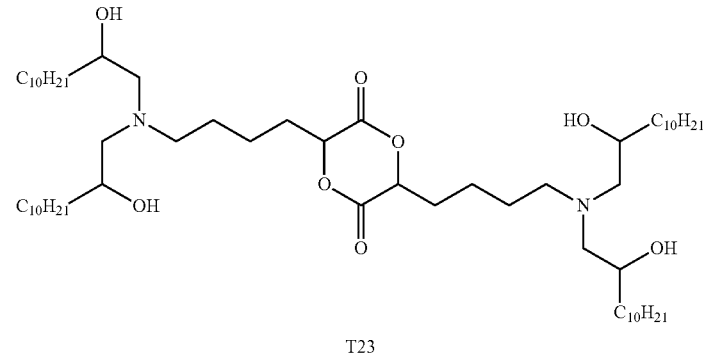

T23

As shown in Scheme 1, exemplary compounds of formula I are prepared from L-lysine 1. L-lysine is first converted, via sodium nitrite and sulfuric acid, to a 6-amino-2-hydroxyhexanoic acid intermediate, which is treated with two equivalents of 2-decyloxirane to provide 6-(bis(2-hydroxydodecyl)amino)-2-hydroxyhexanoic acid 3, the alpha-hydroxy acid functionality of which is protected with 2,2-dimethoxypropane to yield 2,2-dimethyl-1,3-dioxolan-4-one 4. Protection of the secondary alcohols and deprotection of the alpha-hydroxy acid functionality of 5 yields 2-hydroxyhexanoic acid 6. 2-Hydroxyhexanoic acid 6 is split into two equivalent portions, one of which is converted to benzyl-protected alcohol 7 and the other is converted to Cbz-protected acid 8. Alcohol 7 and acid 8 are esterified using standard coupling protocols to yield ester 9. Subsequent hydrogenation to removal protecting groups affords the free acid 10, which was coupled intramolecularly to provide the lactone precursor 11. The final step required boron-mediated removal of TBS protecting groups yields the final target compound T23 (Compound of Formula III).

B. Similarly, T23 (the compound of formula III) can be made according to the route shown in Scheme 2:

Scheme 2

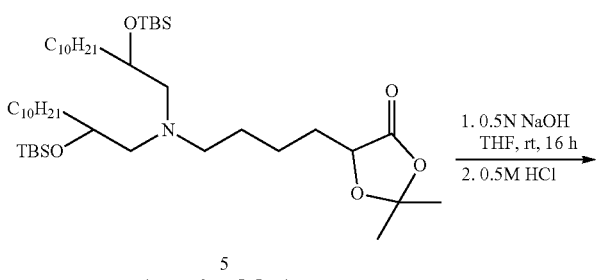

5
4 steps from L-Lysine

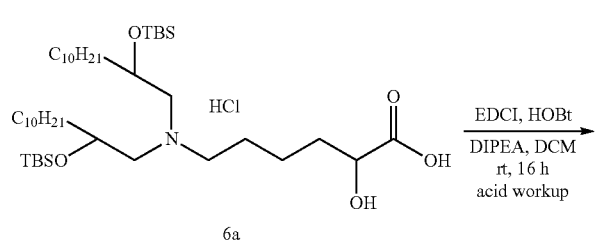

6a

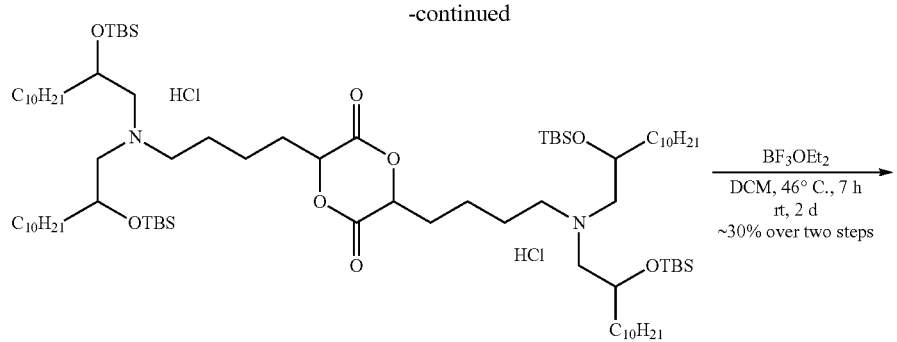
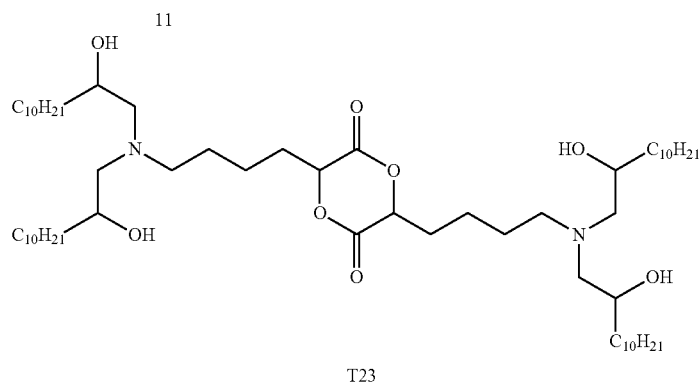
As shown in Scheme 2, a short route to achieving T23 was achieved by ' ' exploiting direct intermolecular cyclization of the free a-hydroxy acid 6a to form the lactone precursor 11. Upon completion, identical boron-mediated removal of the TBS groups afforded the compound of Formula III, T23.
C. T23 can be also made according to the route shown in Scheme 3:
Scheme 3
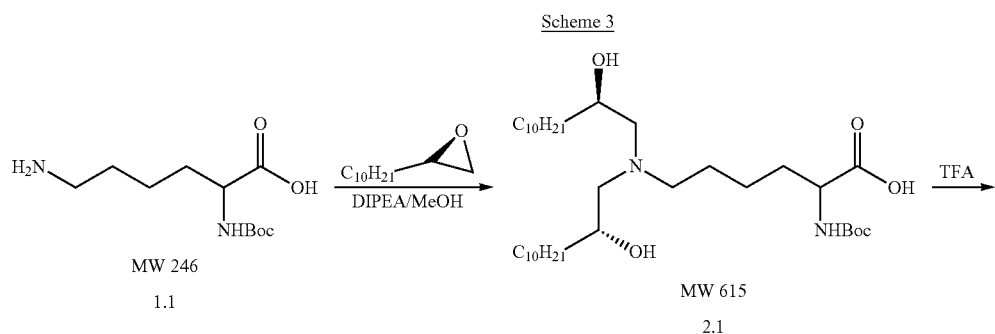
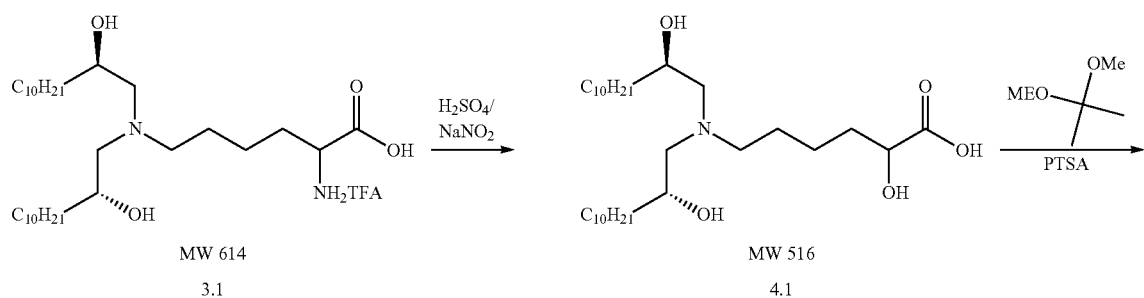

-continued
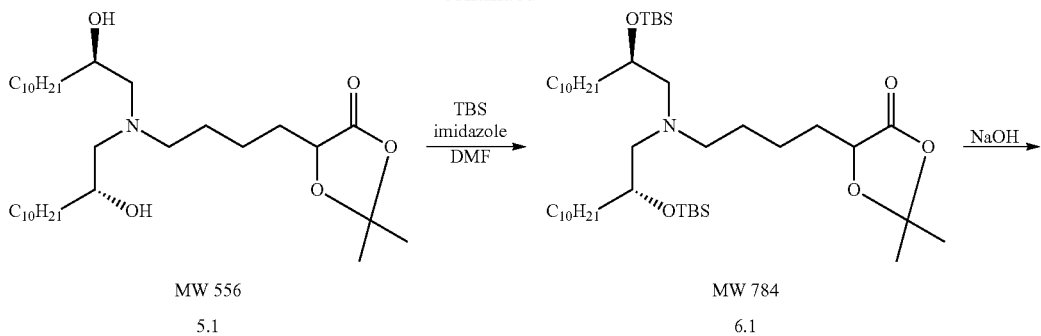
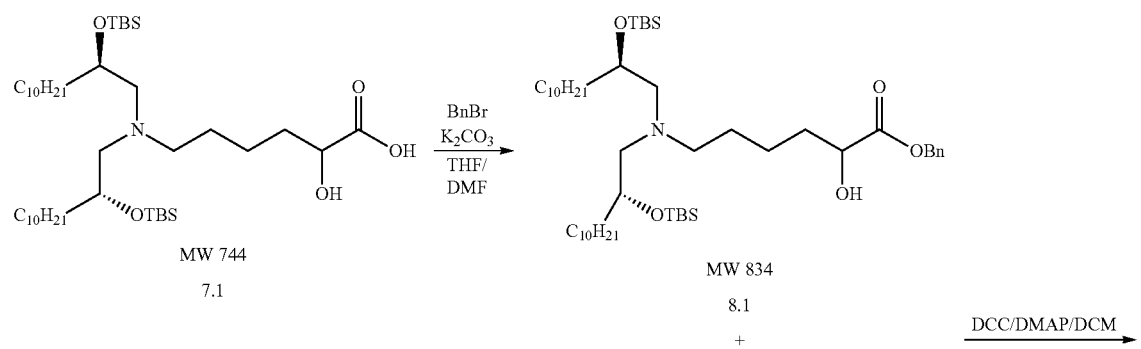
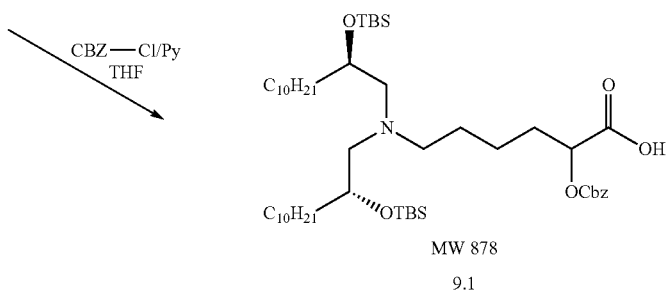
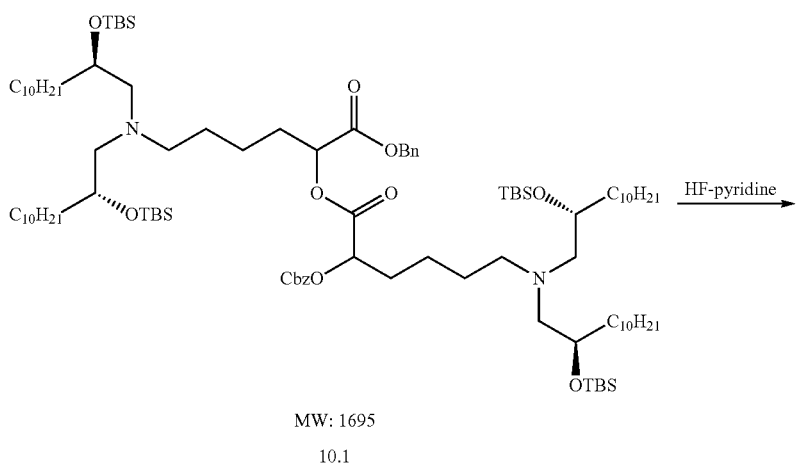

-continued
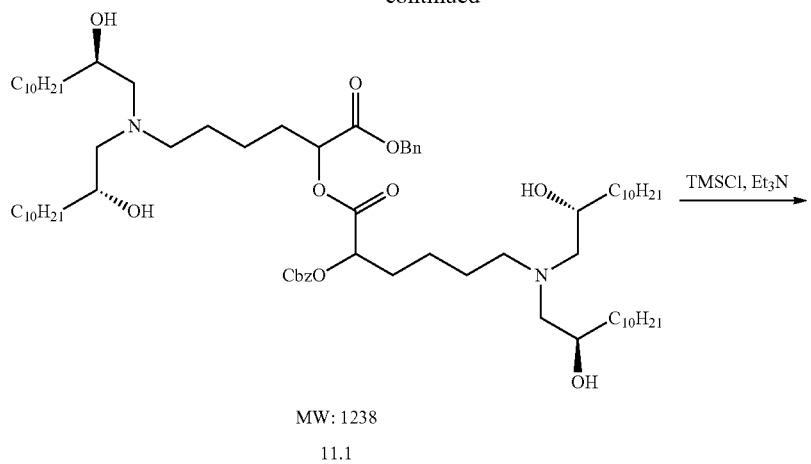
MW: 1238
11.1
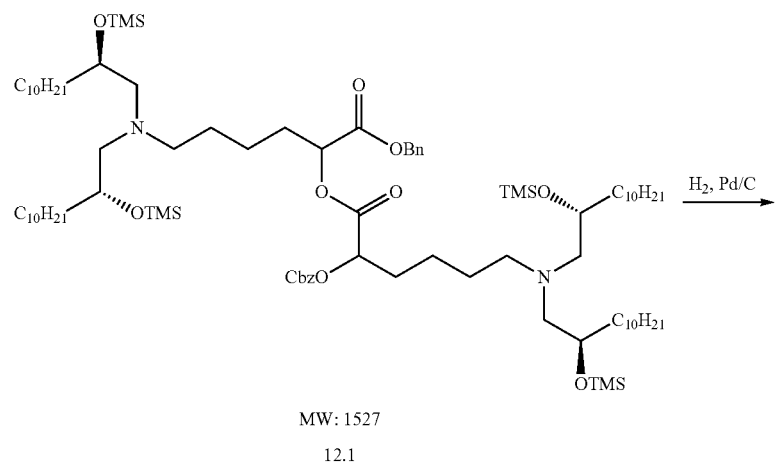
MW: 1527
12.1
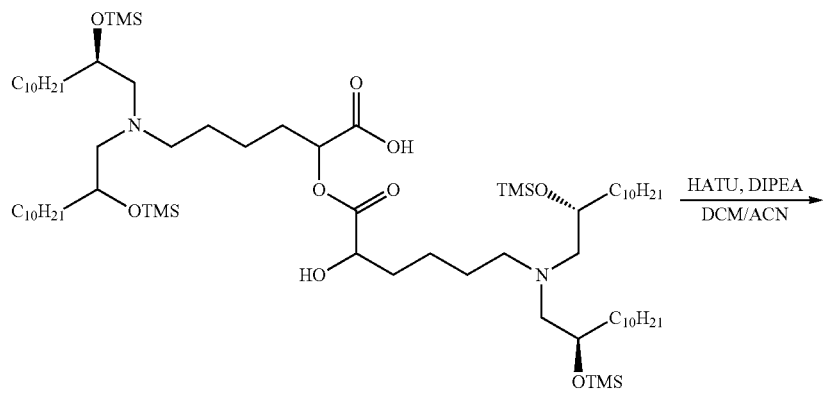
MW: 1302
13.1

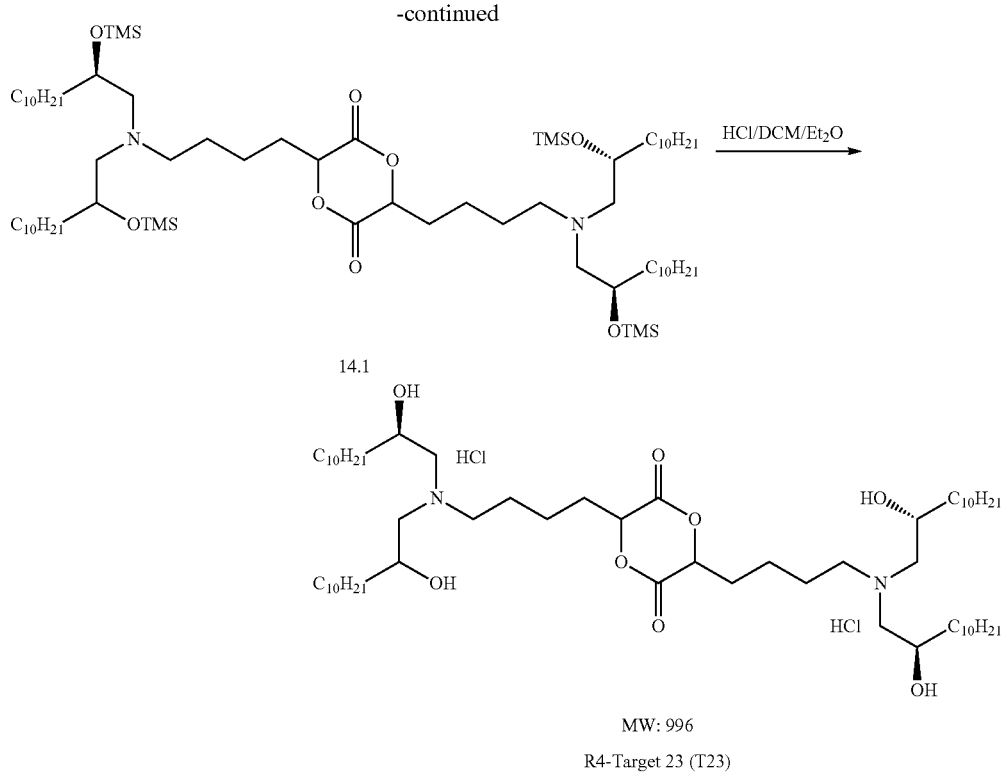

MW: 996
R4-Target 23 (T23)

Synthesis of Compound 2.1

To a mixture of Boc-Lys-OH (18 g, 73 mmol) and DIPEA (16 mL) in methanol (216 mL) at room temperature was added (2S)-1,2-epoxydodecane (40 g, 219 mmol). The reaction mixture was heated at reflux overnight. The light yellow clear solution was concentrated to give a yellow oil, which was mixed with THF (120 mL), water (100 mL) and lithium hydroxide (6 g, 250 mmol) and stirred at room temperature overnight. The reaction mixture was then extracted with dichloromethane/methanol (9:1, 500 mL×4). The combined organic layers were dried over $Na_2SO_4$. Filtration and concentration gave 82 g crude product which was purified by flash chromatography on silica gel (1 kg, 0-35% methanol in ethyl acetate) to yield 38.6 g (81%) of 2.1 as an off-white solid.

Synthesis of Compound 3.1

A solution of compound 2.1 (38.6 g, 62.9 mmol) in anhydrous dichloromethane (200 mL) and trifluoroacetic acid (200 mL) was stirred at room temperature for 1 h. The reaction mixture was concentrated under reduced pressure. The residue was dried under vacuum to give 39.5 g (100%) crude product 3.1 that was used directly for the next step without further purification.

Synthesis of Compound 4.1

To a mixture of compound 3.1 (39.5 g, 62.9 mmol) in 10% sulfuric acid (520 mL) at 0-5° C. (ice-water bath) with vigorously stirring, a solution of sodium nitrite (32 g, 464 mmol) in water (130 mL) was added dropwise in over 2 h while keeping the internal temperature below 5° C. After the addition was finished, the reaction mixture was allowed to warm up slowly to room temperature and stirred overnight. The reaction mixture was then extracted with dichloromethane/methanol (9:1, 800 mL×6). The combined organic layers were washed with saturated aqueous $Na_2S_2O_3$ solution and brine, then dried over $Na_2SO_4$. Filtration and concentration of the filtrate gave 38 g crude product which was purified using a Teledyne ISCO Combiflash automatic chromatography system (330 g Redisep silica gel column, 0-50% MeOH in $CH_2Cl_2$ gradient) to give 8.4 g of product 4.1 as light yellow foam (Yield: 73%, based on starting material consumed). 21 g of starting material 3.1 (free base) was also recovered.

Synthesis of Compound 5.1

Pyridinium p-toluenesulfonate (4.15 g, 16.5 mmol) was added to a solution of compound 4.1 (6.05 g, 11 mmol) in THF/2,2-dimethoxypropane (40 mL/40 mL). The resulting mixture was stirred at 55° C. for 5 h and 50° C. overnight. The solvents were removed under reduced pressure. The residue was dried under vacuum and used without purification.

Synthesis of Compound 6.1

The crude compound 5.1 was dissolved in DMF (30 mL). To this solution was added DMAP (269 mg, 2.2 mmol), imidazole (4.49 g, 66 mmol), and TBDMSCl (6.63 g, 44 mmol). The resulting solution was stirred at room temperature overnight. The solvents were removed under reduced pressure. The residue was partitioned between $Et_2O$ (150 mL) and water (50 mL). The organic layer was separated, washed with brine (2×25 mL), dried over $Na_2SO_4$, and filtered. The filtrate was evaporated in vacuo and the residue was purified by column chromatography on silica gel (0-20% EtOAc/hexane) to give 5.4 g (63%, over two steps) of the desired product as a colorless oil.

Synthesis of Compound 7.1 (HCl Salt)

To a solution of compound 6.1 (5.32 g, 6.8 mmol) in THF (65 mL) was added dropwise 0.5 N NaOH (16.3 mL, 8.2 mmol). The resulting mixture was stirred at room temperature overnight. EtOAc (150 mL) was added. The mixture was acidified with 0.5 M HCl (40 mL). Then brine (60 mL) was added. The organic layer was separated, washed with brine (2×50 mL), dried over $Na_2SO_4$, and filtered. The filtrate was evaporated in vacuo. The residue was dried under vacuum to give 5.26 g (98%) of the desired product as an off-white wax.

Synthesis of Compound 7.1 (Sodium Salt)

To a solution of compound 6.1 (6.5 g, 8.3 mmol) in THF (80 mL) was added dropwise 0.5 N NaOH (20 mL, 10 mmol). The resulting mixture was stirred at room temperature overnight. $Et_2O$ (200 mL) was added. The organic layer was washed with brine (3×50 mL), dried over $Na_2SO_4$, and filtered. The filtrate was evaporated in vacuo to give 6.5 g (99%) of the desired product as a colorless oil.

Synthesis of Compound 8.1

Benzyl bromide (1.08 mL, 9.1 mmol) was added dropwise to a solution of sodium salt of compound 7.1 (6.5 g, 8.3 mmol) in DMF/THF (30 mF/30 mL). The resulting solution was stirred at room temperature for 18 h. The solvents were removed under reduced pressure. The residue was taken up in EtOAc (150 mL). The organic layer was washed with water (25 mL), brine (2×25 mL), dried over $Na_2SO_4$, and filtered. The filtrate was evaporated in vacuo and the residue was purified by column chromatography on silica gel (0-20% EtOAc/hexane) to give 6.31 g (91%) of the desired product as a colorless oil.

Synthesis of Compound 9.1

To a cold (0° C.) solution of compound 7.1 HCl salt (5.26 g, 6.74 mmol) in THF/pyridine (15 mL/10 mL) was added dropwise benzyl chloroformate (1.15 mL, 8.1 mmol). The resulting mixture was allowed to warm to room temperature and stirred overnight. An aliquot of the reaction mixture was taken out for MS analysis. The result indicated the reaction did not go to completion. Benzyl chloro formate (1.15 mL, 8.1 mmol) was added. The reaction mixture was stirred at room temperature for another 1.5 h, then diluted with EtOAc (200 mL). The organic layer was washed with water (50 mL), 1.5 M HCl (2×50 mL), brine (3×40 mL), dried over $Na_2SO_4$, and filtered. The filtrate was evaporated in vacuo and the residue was purified by column chromatography on silica gel (0-70% EtOAc/hexane) to give 2.78 g (45%) of the desired product as light yellow oil.

Synthesis of Compound 10.1

To a cold (0° C.) solution of compound 8.1 (3.5 g, 4.2 mmol) and compound 9.1 (2.78 g, 3 mmol) in DCM (30 mL) was added DMAP (673 mg, 6 mmol) and DCC (2.48 g, 12 mmol). The resulting mixture was allowed to warm to room temperature and stirred overnight. DCM was removed under reduced pressure and the residue was taken up in $Et_2O$ and filtered. The filtrate was evaporated in vacuo. The residue was purified by column chromatography on silica gel (0-20% EtOAc/hexane) to give 4.87 g (95%, contaminated with dicyclohexyl urea) of the desired product as a colorless oil.

Synthesis of Compound 11.1

To a solution of 10.1 (4.0 g, 2.36 mmol) in THF (anhydrous, 15 mL) in a 100 ml Teflon flask at 0° C. was added dropwise a 70% wt/30% wt HF-pyridine solution (15 mL, 578 mmol). The resulting mixture was stirred at room temperature for 2.5 h. Mass spectrometry analysis indicated completion of the reaction. The reaction solution was diluted with DCM (50 mL). The DCM solution was added to a mixture of DCM (200 mL) and aqueous $Na_2CO_3$ solution (40 g in 180 mL of water) with rapid stirring. The DCM layer was separated. The aqueous layer was extracted with DCM (150 mL). The combined organic phase was dried over $Na_2SO_4$ and evaporated. The light yellow oily residue was purified by silica gel column (120 g) on an ISCO automatic chromatography system eluting with 0-100% EtOAc in hexanes to give 2.66 g of 11.1 (77%) as a light yellow oil.

Synthesis of Compound 12.1

To a solution of 11.1 (2.66 g, 2.15 mmol) in THF (anhydrous, 70 mL) was added $Et_3N$ (2.39 mL, 17.2 mmol), followed by TMSCl (1.49 mL, 11.8 mmol). The resulting mixture was stirred at room temperature overnight. Volatiles were removed. The residue was stirred with $Et_2O$ (anhydrous, 100 mL) for 20 min and filtered. The solid was rinsed with $Et_2O$ (anhydrous, 2×20 mL). The combined filtrate was evaporated and residue was dried under vacuum overnight to give 3.15 g of 12.1 (96%) as light yellow oil.

Synthesis of Compound 13.1

To a suspension of dry Pd/C (5%, 1.6 g) in EtOAc (15 mL) was added a solution of 12.1 (3.15 g, 2.1 mmol) in EtOAc (70 mL). The resulting mixture was stirred under a hydrogen balloon overnight. It was then filtered through Celite. The Celite was rinsed with EtOAc (25 mL×3). The combined filtrate was evaporated to give 2.09 g of 13.1 (78%) as a light yellow oil.

Synthesis of Target 23

To a solution of 13.1 (2.09 g, 1.6 mmol) in a mixture of DCM (anhydrous, 60 mL) and $CH_3CN$ (anhydrous, 30 mL) was added DIPEA (0.415 mL, 2.4 mmol), followed by HATU (0.912 g, 2.4 mmol). The resulting mixture was stirred at room temperature under $N_2$ for 16 h. Volatiles were removed. The residue was extracted with hexane (100 mL+25 mL×2). The hexane extracts were combined and washed with aqueous $NaHCO_3$ (2×60 mL) and aq. HCl (5 mL 1 M HCl in 60 mL of $H_2O$). It was dried over $Na_2SO_4$ and filtered. The filtrate was evaporated to give compound 14.1 as light yellow foam which was dissolved in DCM (anhydrous, 25 mL). HCl in diethyl ether (2M, 6 mL) was added dropwise and the resulting mixture was stirred at room temperature under $N_2$ for 3 h. Mass spectrometry analysis indicated completion of the reaction. Solvents were removed by purging with a nitrogen gas flow. The residue was washed with anhydrous diethyl ether (10 mL×3) and dried under high vacuum to give 1.61 g of Target 23 as off-white solid (94%, two steps).

D. The compound of Formula IV, Target 24 (T24), can be made according to the route shown in Scheme 4:
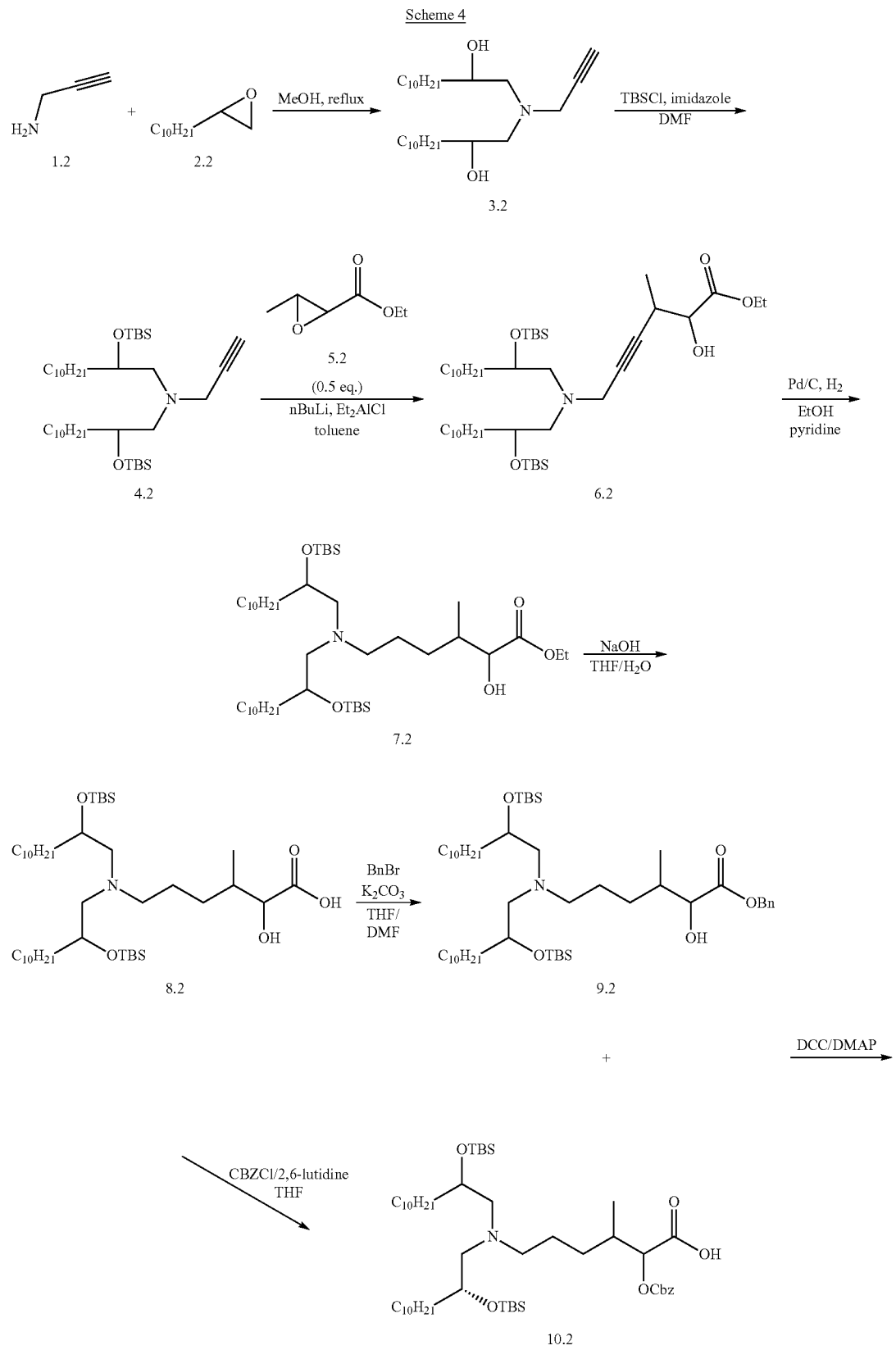
Scheme 4

-continued
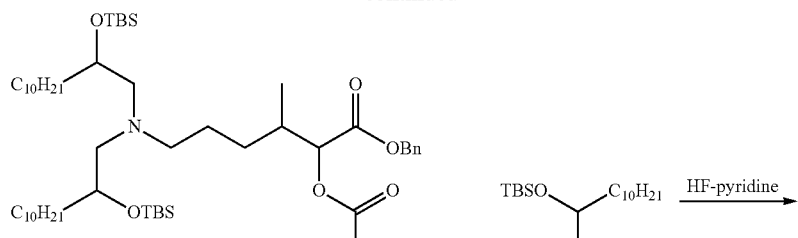
11.2 HF-pyridine →
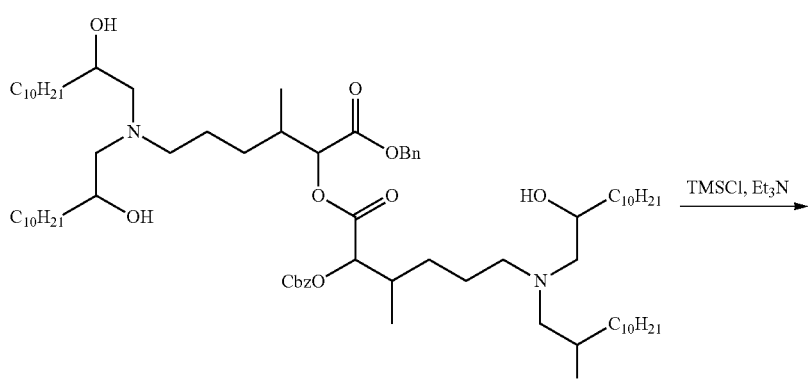
12.2 TMSCl, Et₃N →
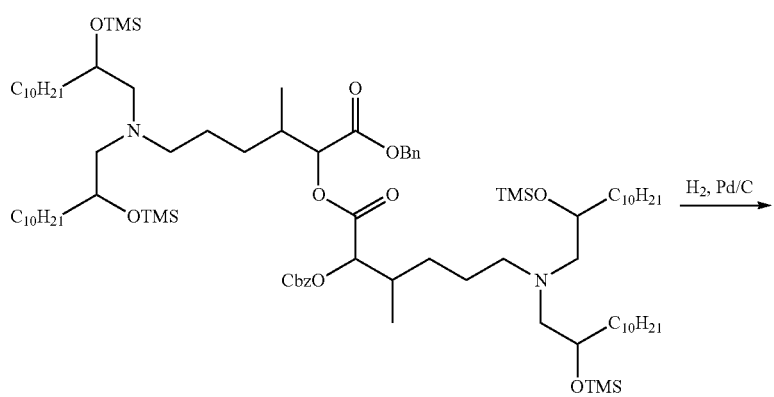
13.2 H₂, Pd/C →
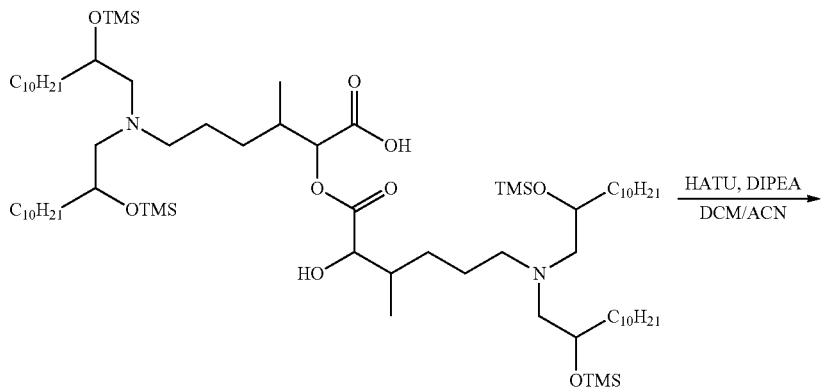
14.2 HATU, DIPEA / DCM/ACN →

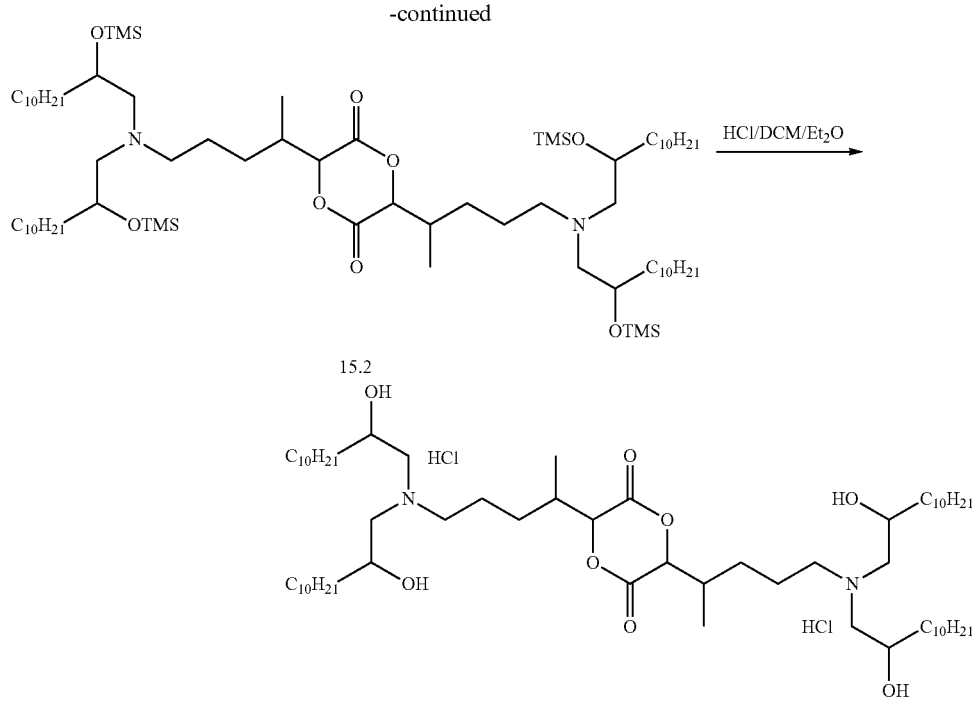

Target 24 (T24)

Synthesis of Compound 3.2

A solution of propargylamine (4.83 g, 87.7 mmol) and 1,2-epoxydodecane (40.8 g, 210.4 mmol) in EtOH (300 mL) was heated under reflux for 16 h. The solvent was removed under reduced pressure and the residue was purified by column chromatography on silica gel (0-30% EtOAc/hexane) to give 32.8 g (88%) of the desired product as a light yellow solid.

Synthesis of Compound 4.2

To a cold (0° C.) solution of 3.2 (10.16 g, 24 mmol) in DMF (48 mL) was added sequentially DMAP (587 mg, 4.8 mmol), imidazole (5.72 g, 84 mmol), and tert-butyldimethylsilyl chloride (9.04 g, 60 mmol). The resulting mixture was stirred at 0° C. for 20 min. The ice bath was then removed, and the reaction was allowed to warm to room temperature and stirred overnight. DMF was removed under reduced pressure. To the residue was added EtOAc (200 mL), water (50 mL), and brine (30 mL). The organic layer was separated, washed with brine (50 mL), dried over $Na_2SO_4$, and filtered. The filtrate was evaporated in vacuo and the residue was purified by column chromatography on silica gel (hexane) to give 14.55 g (93%) of the desired product as colorless oil.

Synthesis of Compound 6.2

To a cold (0° C.) solution of 4.2 (3.52 g, 5.4 mmol) in toluene (40 mL) was added dropwise 2.5 M n-BuLi (2.16 mL, 5.4 mmol). The resulting solution was stirred at 0° C. for 30 min, then 1 M $Et_2AlCl$ (5.4 mL, 5.4 mmol) was added dropwise. After addition, the cloudy solution was stirred at 0° C. for another 2 h, then a solution of 5.2 (375 mg, 2.88 mmol) in toluene (2 mL) was added dropwise. After stirring for 30 min, the ice bath was removed, and the reaction was allowed to warm up to room temperature and stirred overnight. The reaction was cooled with an ice bath then $Na_2SO_4 \cdot 10H_2O$ (8.3 g) was added in one portion. The resulting mixture was stirred vigorously for 2 h. The mixture was filtered and the filtrate was evaporated in vacuo. The residue was purified by column chromatography on silica gel (0-5% EtOAc/hexane) twice to give 1.12 g (53%) of the desired product as a yellow oil.

Synthesis of Compound 7.2

To a solution of 6.2 (2.0 g, 2.56 mmol) in EtOH (50 mL) was added pyridine (1.45 mL, 17.9 mmol) and 5 wt. % Pd/C (272 mg, 0.128 mmol). The resulting mixture was degassed with Ar three times and then stirred under 1 atm $H_2$ overnight. The mixture was filtered through a Celite plug which was washed with EtOH thoroughly. The combined filtrate and washes were evaporated in vacuo to give 2.0 g of light yellow oil as a mixture of the desired product and other inseparable byproducts. The crude was used in next step without further purification.

Synthesis of Compound 8.2

To a solution of crude 7.2 (2.0 g) in THF (31 mL) was added 0.5 N NaOH (6.14 mL, 3.07 mmol) and MeOH (1.5 mL). The resulting mixture was stirred vigorously at room temperature overnight. The solvent was removed under reduced pressure. The residue was taken up in $Et_2O$ (120 mL), and was washed with brine (3×30 mL), dried over $Na_2SO_4$, and filtered. The residue was purified by column chromatography on silica gel (0-50% EtOAc/hexane) to give 739 mg (37% over two steps) of the desired product as a light yellow oil.

Synthesis of Compound 9.2

To a solution of compound 8.2 (739 mg, 0.97 mmol) in DMF/THF (5 mL/10 mL) at room temperature was added $K_2CO_3$ (201 mg, 1.46 mmol). The resulting mixture was stirred for 20 min then benzyl bromide (127 µL, 1.07 mmol) was added. The resulting mixture was stirred at room temperature overnight. The solvents were removed under reduced pressure. The residue was taken up in EtOAc (70 mL) and washed with water (10 mL), brine (15 mL), dried over $Na_2SO_4$, and filtered. The filtrate was evaporated in vacuo and the residue was purified by column chromatography on silica gel (0-10% EtOAc/hexane) to give 796 mg (97%) of the desired product as colorless oil.

Synthesis of Compound 10.2

To a cold (0° C.) solution of 8.2 (795 mg, 1.05 mmol) in THF (10.5 mL) was added sequentially 2,6-lutidine (128 µL, 1.1 mmol) and benzyl chloroformate (157 µL, 1.1 mmol). After stirring for 15 min, the ice bath was removed. The reaction was allowed to warm to room temperature and stirred for 4 h. An aliquot of reaction mixture was taken out for MS analysis. The result indicated the reaction did not go to completion. Then benzyl chloroformate (157 µL, 1.1 mmol) was added. After stirring at room temperature for another 1 h, the reaction was quenched with saturated aqueous $NaHCO_3$ solution (25 mL). The mixture was stirred vigorously overnight. The mixture was diluted with EtOAc (70 mL). The organic layer was separated and the aqueous layer was extracted with EtOAc (20 mL). The combined organic layers were washed with 0.5 M HCl (20 mL), brine (2×15 mL), dried over $Na_2SO_4$, and filtered. The filtrate was evaporated in vacuo and the residue was purified by column chromatography on silica gel (0-50% EtOAc/hexane) to give 663 mg (67%) of the desired product as a yellow oil.

Synthesis of Compound 11.2

To a cold (0° C.) solution of compound 9.2 (800 mg, 0.94 mmol) and 10.2 (664 mg, 0.71 mmol) in $CH_2Cl_2$ (7.1 mL) was added DMAP (157 mg, 1.42 mmol) and DCC (293 mg, 1.42 mmol). After stirring for 15 min, the reaction was allowed to warm up to room temperature and stirred overnight. $CH_2Cl_2$ was removed under reduced pressure. The residue was taken up in $Et_2O$ (50 mL). The white solid was removed by filtration. The filtrate was evaporated in vacuo. The residue was purified by column chromatography on silica gel (0-10% EtOAc/hexane) twice to give 964 mg (79%) of product 11.2 as a colorless oil.

Synthesis of Compound 12.2

To a solution of 11.2 (5.04 g, 2.93 mmol) in THF (anhydrous, 15 mL) was added the 70% wt/30% wt HF-pyridine solution (20 mL, 770 mmol). The resulting mixture was stirred at room temperature. Mass spectrometry analysis after 2.5 h indicated complete reaction. THF was removed. The residual solution was diluted with DCM (50 mF). The DCM solution was added to a mixture of DCM (200 mF) and aqueous $Na_2CO_3$ solution (61 g in 300 mF of water) with rapid stirring. The DCM layer was separated. The aqueous layer was extracted with DCM (150 mF). The combined organic phase was dried over $Na_2SO_4$ and evaporated. The light yellow oily residue was purified by silica gel column (80 g) on an ISCO automatic chromatography system eluting with 0-100% EtOAc in hexane to give 2.85 g of 12.2 (77%) as a light yellow oil.

Synthesis of Compound 13.2

To a solution of 12.2 (2.85 g, 2.25 mmol) in THF (anhydrous, 70 mF) was added $Et_3N$ (2.5 mF, 18 mmol), followed by TMSCl (1.5 mF, 11.9 mmol). The resulting mixture was stirred at room temperature for 3 h. Volatiles were removed. The residue was stirred with $Et_2O$ (anhydrous, 100 mF) for 20 min and filtered. The solid was rinsed with $Et_2O$ (anhydrous, 2×20 mF). The combined filtrate was evaporated and residue was dried under vacuum overnight to give 3.29 g of 13.2 (94%) as a light yellow oil.

Synthesis of Compound 14.2

To a suspension of Pd/C (5%, 1.62 g, mmol) in EtOAc (10 mF) was added a solution of 13.2 (3.29 g, 2.11 mmol) in EtOAc (70 mF). The resulting mixture was stirred under a balloon of $H_2$ for 2 h. It was then filtered through Celite. The Celite was rinsed with EtOAc (3×20 mF). The combined filtrate was evaporated to give 2.78 g of 14.2 (99%) as a light yellow oil.

Synthesis of Compound 15.2

To a solution of 14.2 (2.78 g, 2.09 mmol) in a mixture of DCM (anhydrous, 40 mF) and $CH_3CN$ (anhydrous, 20 mF) was added DIPEA (0.55 mF, 3.14 mmol), followed by HATU (1.19 g, 3.14 mmol). The resulting mixture was stirred at room temperature under $N_2$ for 16 h. Volatiles were removed. The residue was extracted with hexane (150 mL). The hexane extract was washed with aqueous $NaHCO_3$ (2×60 mL) and HCl. It was dried over $Na_2SO_4$ and filtered. The filtrate was evaporated to give 2.36 g (86%) of 15.2 as a light yellow gum.

Synthesis of Target 24

To a solution of 15.2 (1.09 g, 0.83 mmol) in DCM (anhydrous, 15 mL), HCl in diethyl ether (2 M, 3 mL) was added dropwise and the resulting mixture was stirred at room temperature under $N_2$ for 3.5 h. Mass spectrometry analysis indicated completion of the reaction. Solvent was removed by purging with a nitrogen gas flow. The residue was washed with anhydrous diethyl ether (20 mL×3) and dried under high vacuum to give 875 mg of crude Target 24. 255 mg of crude Target 24 was washed with anhydrous acetonitrile (30 mL×3). The residue was dissolved in DCM (anhydrous, 2 mL) and added to a mixture of diethyl ether (anhydrous, 25 mL) and HCl in diethyl ether (2 M, 0.5 mL) with stirring. After continued stirring for 30 minutes, the gummy solid was separated from the solution and was washed with anhydrous diethyl ether (5 mL×2). It was dried under high vacuum to give 200 mg (69%) of Target 24 as an off-white foam.

Example 2. Exemplary Liposome Formulations for mRNA Delivery and Expression

This example provides exemplary liposome formulations incorporating the cationic lipids described in this application, for example, the compound of formula III, for effective delivery and expression of mRNA encoding therapeutic proteins in vivo.

Lipid Materials

In general, the formulations described herein are based on a multi-component lipid mixture of varying ratios employing one or more cationic lipids, one or more helper lipids (e.g., non-cationic lipids and/or cholesterol-based lipids), and one or more PEGylated lipids designed to encapsulate various nucleic acid-based materials. As a non-limiting example, the compound of Formula III (3,6-bis(4-(bis(2-hydroxydodecyl)amino)butyl)-1,4-dioxane-2,5-dione) is used in various formulations described herein. Exemplary helper lipids include one or more of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)), cholesterol, etc. Exemplary PEGylated lipids include a poly(ethylene) glycol chain of up to 5 kDa in length covalently attached to a lipid with alkyl chain(s) of $C_6$-$C_{20}$ length, for example, PEG-2K. As non-limiting examples, liposome formulations used in various examples described herein include the compound of Formula III, DOPE, cholesterol and DMG-PEG2K at various ratios. For example, in some cases, the ratio of the compound of Formula III:DOPE:cholesterol:DMG-PEG2K is approximately 40:30:20:10 by weight. In other cases, the ratio of the compound of Formula III:DOPE:cholesterol:DMG-PEG2K is approximately 40:32:25:3 by weight. Unless otherwise specified, the below Examples include a mixture in the ratio of the compound of Formula III:DOPE:cholesterol:DMG-PEG2K of approximately 40:30:25:5 by weight.

Messenger RNA Material

The formulations described herein may be used to deliver any mRNA, in particular, therapeutic mRNA. As used herein, a therapeutic mRNA refers to an mRNA that encodes a therapeutic protein. The formulations described herein can also be used to deliver any modified or unmodified mRNA, or mRNA with naturally occurring sequences or codon-optimized.

As non-limiting examples, human Factor IX (FIX), codon-optimized Firefly Luciferase (FFL), codon-optimized human argininosuccinate synthetase (ASS1) messenger RNA, codon-optimized human Spinal Motor Neuron 1 (SMN) mRNA were synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" *J. Gen. Virology* 2005, 86, 1239-1249) and a 3' poly(A) tail of, e.g., approximately 250 nucleotides in length as determined by gel electrophoresis. Typically, 5' and 3' untranslated regions (UTR) are present in each mRNA product and are represented as X and Y, respectively. Example 5' and 3' UTR sequences are described below. The exemplary sequences of FIX, ASS1, and FFL mRNA used in the examples herein are listed below. Also shown are the 5' and 3' UTR sequences.

```
Codon-Optimized Firefly Luciferase (FFL) mRNA:
                                         (SEQ ID NO.: 3)
XAUGGAAGAUGCCAAAAACAUUAAGAAGGGCCCAGCGCCAUUCUACCC
ACUCGAAGACGGGACCGCCGGCGAGCAGCUGCACAAAGCCAUGAAGCG
CUACGCCCUGGUGCCCGGCACCAUCGCCUUUACCGACGCACAUAUCGA
GGUGGACAUUACCUACGCCGAGUACUUCGAGAUGAGCGUUCGGCUGGC
AGAAGCUAUGAAGCGCUAUGGGCUGAAUACAAACCAUCGGAUCGUGGU
GUGCAGCGAGAAUAGCUUGCAGUUCUUCAUGCCCGUGUUGGGUGCCCU
GUUCAUCGGUGUGGCUGUGGCCCCAGCUAACGACAUCUACAACGAGCG
CGAGCUGCUGAACAGCAUGGGCAUCAGCCAGCCCACCGUCGUAUUCGU
GAGCAAGAAAGGGCUGCAAAAGAUCCUCAACGUGCAAAAGAAGCUACC
GAUCAUACAAAAGAUCAUCAUCAUGGAUAGCAAGACCGACUACCAGGG
CUUCCAAAGCAUGUACACCUUCGUGACUUCCCAUUUGCCACCCGGCUU
CAACGAGUACGACUUCGUGCCCGAGAGCUUCGACCGGGACAAAACCAU
CGCCCUGAUCAUGAACAGUAGUGGCAGUACCGGAUUGCCCAAGGGCGU
AGCCCUACCGCACCGCACCGCUUGUGUCCGAUUCAGUCAUGCCCGCGA
CCCCAUCUUCGGCAACCAGAUCAUCCCCGACACCGCUAUCCUCAGCGU
GGUGCCAUUUCACCACGGCUUCGGCAUGUUCACCACGCUGGGCUACUU
GAUCUGCGGCUUUCGGGUCGUGCUCAUGUACCGCUUCGAGGAGGAGCU
AUUCUUGCGCAGCUUGCAAGACUAUAAGAUUCAAUCUGCCCUGCUGGU
GCCCACACUAUUUAGCUUCUUCGCUAAGAGCACUCUCAUCGACAAGUA
CGACCUAAGCAACUUGCACGAGAUCGCCAGCGGCGGGGCGCCGCUCAG
CAAGGAGGUAGGUGAGGCCGUGGCCAAACGCUUCCACCUACCAGGCAU
CCGCCAGGGCUACGGCCUGACAGAAACAACCAGCGCCAUUCUGAUCAC
CCCCGAAGGGGACGACAAGCCUGGCGCAGUAGGCAAGGUGGUGCCCUU
CUUCGAGGCUAAGGUGGUGGACUUGGACACCGGUAAGACACUGGGUGU
GAACCAGCGCGGCGAGCUGUGCGUCCGUGGCCCCAUGAUCAUGAGCGG
CUACGUUAACAACCCCGAGGCUACAAACGCUCUCAUCGACAAGGACGG
CUGGCUGCACAGCGGCGACAUCGCCUACUGGGACGAGGACGAGCACUU
CUUCAUCGUGGACCGGCUGAAGAGCCUGAUCAAAUACAAGGGCUACCA
GGUAGCCCCAGCCGAACUGGAGAGCAUCCUGCUGCAACACCCCAACAU
CUUCGACGCCGGGGUCGCCGGCCUGCCCGACGACGAUGCCGGCGAGCU
GCCCGCCGCAGUCGUCGUGCUGGAACACGGUAAAACCAUGACCGAGAA
GGAGAUCGUGGACUAUGUGGCCAGCCAGGUUACAACCGCCAAGAAGCU
GCGCGGUGGUGUUGUGUUCGUGGACGAGGUGCCUAAAGGACUGACCGG
CAAGUUGGACGCCCGCAAGAUCCGCGAGAUUCUCAUUAAGGCCAAGAA
GGGCGGCAAGAUCGCCGUGUAAY 5' and 3' UTR Sequences
X (5' UTR Sequence) =
                                         (SEQ ID NO.: 5)
GGACAGAUCGCCUGGAGACGCCAUCCACGCUGUUUUGACCUCCAUAGA
AGACACCGGGACCGAUCCAGCCUCCGCGGCCGGGAACGGUGCAUUGGA
ACGCGGAUUCCCCGUGCCAAGAGUGACUCACCGUCCUUGACACG
```

-continued

Y (3' UTR Sequence) =

(SEQ ID NO.: 6)
CGGGUGGCAUCCCUGUGACCCCUCCCCAGUGCCUCUCCUGGCCCUGGA

AGUUGCCACUCCAGUGCCCACCAGCCUUGUCCUAAUAAAAUUAAGUUG

CAUCAAGCU or (SEQ ID NO.: 7)
GGGUGGCAUCCCUGUGACCCCUCCCCAGUGCCUCUCCUGGCCCUGGAA

GUUGCCACUCCAGUGCCCACCAGCCUUGUCCUAAUAAAAUUAAGUUGC

AUCAAGCU

Aliquots of 50 mg/mL ethanolic solutions of the compound of Formula III, DOPE, Choi and DMG-PEG2K are mixed in a molar ratio of 40:30:25:5 and diluted with ethanol to 3 mL final volume. Separately, an aqueous buffered solution (10 mM citrate/150 mM NaCl, pH 4.5) of FIX, ASS1, or FFL mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration of FIX mRNA is typically diluted to approximately 0.20 mg/mL FIX mRNA (encapsulated), $Z_{ave}$=76 nm, PDI=0.08. The final concentration of ASS1 mRNA is typically diluted to approximately 0.20 mg/mL ASS1 mRNA (encapsulated), $Z_{ave}$=78 nm (Dv(50)=46 nm; Dv(90)=96 nm). The final concentration of FFL mRNA is typically diluted to approximately 0.20 mg/mL FFL mRNA (encapsulated), $Z_{ave}$=75 nm, PDI—0.11. The final concentration of SMN mRNA is typically diluted to approximately 0.20 mg/mL SMN mRNA (encapsulated). Average particle size $(Z_{ave})$=71 nm, (particle size for 50% of particles was 44 nm or less (Dv(50))=44 nm; and the particle size for 90% of the particles was 93n or less (Dv(90)=93 nm)).

Exemplary Formulation Comprising T23

Aliquots of 50 mg/mL ethanolic solutions of the compound of Target 23, DOPE, Choi and DMG-PEG2K were mixed in a molar ratio of 40:30:25:5 and diluted with ethanol to 3 mL final volume. Separately, an aqueous buffered solution (10 mM citrate/150 mM NaCl, pH 4.5) of EPO mRNA was prepared from a 1 mg/mL stock. The lipid solution was injected rapidly into the aqueous mRNA solution and shaken to yield a final suspension in 20% ethanol. The resulting nanoparticle suspension was diafiltrated with 1×PBS (pH 7.4), concentrated and stored at 2-8° C. The final concentration of EPO mRNA is typically diluted to approximately 0.20 mg/mL EPO mRNA (encapsulated). $Z_{ave}$=80 nm, PDI=0.11.

Exemplary Formulation Comprising T24

Aliquots of 50 mg/mL ethanolic solutions of the compound of Target 24, DOPE, Chol and DMG-PEG2K were mixed in a molar ratio of 40:30:25:5 and diluted with ethanol to 3 mL final volume. Separately, an aqueous buffered solution (10 mM citrate/150 mM NaCl, pH 4.5) of EPO mRNA was prepared from a 1 mg/mL stock. The lipid solution was injected rapidly into the aqueous mRNA solution and shaken to yield a final suspension in 20% ethanol. The resulting nanoparticle suspension was diafiltrated with 1×PBS (pH 7.4), concentrated and stored at 2-8° C. The final concentration of EPO mRNA is typically diluted to approximately 0.20 mg/mL EPO mRNA (encapsulated). $Z_{ave}$=78 nm, PDI=0.14.

Example 3. In Vivo Results

CD-1 Mice (N=4 per group) were injected with a 0.20 mg/mL formulation of either Target 23-based LNPs or Target 24-based LNPs loaded with hEPO mRNA (1.0 mg/kg). Serum levels of hEPO were monitored at 6 hr and 24 hr post-dose. See FIG. 1. Liver enzymes (ALT/AST) were measured 24 hr post-administration. See Table 1.

TABLE 1

Liver enzymes levels in wild type mouse sera after treatment via hEPO mRNA loaded LNPs.

| Formulation | ALT Levels | AST Levels |
| --- | --- | --- |
| Target 23 LNP | 107 ± 37 | 92 ± 17 |
| Target 24 LNP | 77 ± 16 | 73 ± 11 |

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A lipid nanoparticle comprising:

messenger RNA (mRNA) encoding a protein;

one or more non-cationic lipids, one or more cholesterol-based lipids and/or one or more PEG-modified lipids; and a compound of formula III:

[Structure III shown]

or a pharmaceutically acceptable salt thereof.

2. A lipid nanoparticle comprising:

messenger RNA (mRNA) encoding a protein;

one or more non-cationic lipids, one or more cholesterol-based lipids and/or one or more PEG-modified lipids; and a compound of formula IV:

[Structure IV shown]

or a pharmaceutically acceptable salt thereof.

3. A lipid nanoparticle comprising:

messenger RNA (mRNA) encoding a protein;

one or more non-cationic lipids, one or more cholesterol-based lipids and/or one or more PEG-modified lipids; and a compound of formula V:

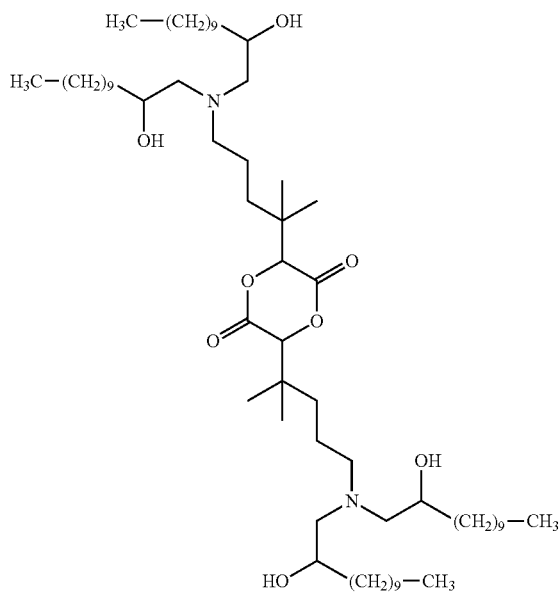

or a pharmaceutically acceptable salt thereof.

4. The lipid nanoparticle of claim 1, wherein the lipid nanoparticle is a liposome.

5. The lipid nanoparticle of claim 1, wherein the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine), DPPE (1,2-dipalmitoyl-sn-glycero-3-phospho-ethanolamine), DMPE (1,2-dimyristoyl-sn-glycero-3-phosphoethanolamine), DOPG (1,2-dioleoyl-sn-glycero-3-phospho-(1'-rac-glycerol)).

6. The lipid nanoparticle of claim 1, wherein the one or more PEG-modified lipids comprise a poly(ethylene) glycol chain of up to 5 kDa in length covalently attached to a lipid with alkyl chain(s) of $C_6$-$C_{20}$ length.

7. The lipid nanoparticle of claim 4, wherein the liposome has a size less than about 250 nm, 200 nm, 150 nm, 100 nm, 75 nm, or 50 nm.

8. The lipid nanoparticle of claim 1, wherein the protein encoded by the mRNA is a cytosolic protein, a secreted protein, or an enzyme.

9. The lipid nanoparticle of claim 1, wherein the mRNA comprises one or more modified nucleotides.

10. The lipid nanoparticle of claim 9, wherein the one or more modified nucleotides comprise pseudouridine, N-1-methyl-pseudouridine, 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine.

11. The lipid nanoparticle of claim 1, wherein the mRNA is unmodified.

12. The lipid nanoparticle of claim 2, wherein the lipid nanoparticle is a liposome.

13. The lipid nanoparticle of claim 2, wherein the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine), DPPE (1,2-dipalmitoyl-sn-glycero-3-phospho-ethanolamine), DMPE (1,2-dimyristoyl-sn-glycero-3-phosphoethanolamine), DOPG (1,2-dioleoyl-sn-glycero-3-phospho-(1'-rac-glycerol)).

14. The lipid nanoparticle of claim 2, wherein the one or more PEG-modified lipids comprise a poly(ethylene) glycol chain of up to 5 kDa in length covalently attached to a lipid with alkyl chain(s) of $C_6$-$C_{20}$ length.

15. The lipid nanoparticle of claim 12, wherein the liposome has a size less than about 250 nm, 200 nm, 150 nm, 100 nm, 75 nm, or 50 nm.

16. The lipid nanoparticle of claim 2, wherein the protein encoded by the mRNA is a cytosolic protein, a secreted protein, or an enzyme.

17. The lipid nanoparticle of claim 2, wherein the mRNA comprises one or more modified nucleotides.

18. The lipid nanoparticle of claim 17, wherein the one or more modified nucleotides comprise pseudouridine, N-1-methyl-pseudouridine, 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine.

19. The lipid nanoparticle of claim 2, wherein the mRNA is unmodified.

20. The lipid nanoparticle of claim 3, wherein the lipid nanoparticle is a liposome.

21. The lipid nanoparticle of claim 3, wherein the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine), DPPE (1,2-dipalmitoyl-sn-glycero-3-phospho-ethanolamine), DMPE (1,2-dimyristoyl-sn-glycero-3-phosphoethanolamine), DOPG (1,2-dioleoyl-sn-glycero-3-phospho-(1'-rac-glycerol)).

22. The lipid nanoparticle of claim 3, wherein the one or more PEG-modified lipids comprise a poly(ethylene) glycol chain of up to 5 kDa in length covalently attached to a lipid with alkyl chain(s) of $C_6$-$C_{20}$ length.

23. The lipid nanoparticle of claim 20, wherein the liposome has a size less than about 250 nm, 200 nm, 150 nm, 100 nm, 75 nm, or 50 nm.

24. The lipid nanoparticle of claim 3, wherein the protein encoded by the mRNA is a cytosolic protein, a secreted protein, or an enzyme.

25. The lipid nanoparticle of claim 3, wherein the mRNA comprises one or more modified nucleotides.

26. The lipid nanoparticle of claim 25, wherein the one or more modified nucleotides comprise pseudouridine, N-1-methyl-pseudouridine, 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine.

27. The lipid nanoparticle of claim 3, wherein the mRNA is unmodified.

* * * * *